(12) United States Patent
Turner et al.

(10) Patent No.: US 6,890,492 B1
(45) Date of Patent: May 10, 2005

(54) PARALLEL REACTOR WITH INTERNAL SENSING AND METHOD OF USING SAME

(75) Inventors: Howard Turner, Campbell, CA (US); G. Cameron Dales, Palo Alto, CA (US); Lynn VanErden, Livermore, CA (US); Johannes A. M. Van Beek, New Orleans, LA (US); Damian A. Hajduk, San Jose, CA (US); Ralph B. Nielsen, San Jose, CA (US); Paul Mansky, San Francisco, CA (US); Leonid Matsiev, Cupertino, CA (US); Pei Wang, San Jose, CA (US); Eric McFarland, Santa Barbara, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 100 days.

(21) Appl. No.: 09/724,276

(22) Filed: Nov. 28, 2000

Related U.S. Application Data

(60) Division of application No. 09/548,848, filed on Apr. 13, 2000, now Pat. No. 6,455,316, which is a continuation-in-part of application No. 09/239,223, filed on Jan. 29, 1999, now Pat. No. 6,489,168, and a continuation-in-part of application No. 09/211,982, filed on Dec. 14, 1998, now Pat. No. 6,306,658, which is a continuation-in-part of application No. 09/177,170, filed on Oct. 22, 1998, now Pat. No. 6,548,026.
(60) Provisional application No. 60/096,603, filed on Aug. 13, 1998.

(51) Int. Cl.[7] ............................. B01J 19/00; B01F 7/00
(52) U.S. Cl. ....................... 422/130; 366/244; 366/249; 366/251; 366/252; 366/273; 366/279; 422/131; 422/135; 422/138; 436/37
(58) Field of Search ............................. 422/62, 65, 93, 422/102, 104, 130–131, 135, 138, 196–197; 436/37, 147, 159, 161, 164, 183, 172–173; 366/244, 249, 251–252, 273, 279

(56) References Cited

U.S. PATENT DOCUMENTS

| 94,830 A | 9/1869 | King |
|---|---|---|
| 1,111,374 A | 9/1914 | Goddard et al. |

(Continued)

FOREIGN PATENT DOCUMENTS

| CS | 266759 | 6/1990 |
|---|---|---|
| CZ | 280 902 | 2/1988 |

(Continued)

OTHER PUBLICATIONS

Salzman. R. N. et al, Proceedings of the European Conference on Mixing 1988, 6th 79–84.*
Erismann, N. de M. et al, Bioresource Technology 1994, 27, 247–256.*

(Continued)

*Primary Examiner*—Arlen Soderquist
(74) *Attorney, Agent, or Firm*—Senniger Powers

(57) ABSTRACT

Devices and methods for controlling and monitoring the progress and properties of multiple reactions are disclosed. The method and apparatus are especially useful for synthesizing, screening, and characterizing combinatorial libraries, but also offer significant advantages over conventional experimental reactors as well. The apparatus generally includes multiple vessels for containing reaction mixtures, and systems for controlling the stirring rate and temperature of individual reaction mixtures or groups of reaction mixtures. In addition, the apparatus may include provisions for independently controlling pressure in each vessel, and a system for injecting liquids into the vessels at a pressure different than ambient pressure. In situ monitoring of individual reaction mixtures provides feedback for process controllers, and also provides data for determining reaction rates, product yields, and various properties of the reaction products, including viscosity and molecular weight. Computer-based methods are disclosed for process monitoring and control, and for data display and analysis.

29 Claims, 41 Drawing Sheets

U.S. PATENT DOCUMENTS

| | | | |
|---|---|---|---|
| 1,281,610 A | 10/1918 | Lundahl | |
| 1,841,434 A | 1/1932 | Gibson | |
| 2,025,379 A | 12/1935 | Croasdale, Jr. | |
| 2,202,860 A | 6/1940 | McPhee et al. | |
| 2,484,391 A | 10/1949 | Treiss, Jr. | |
| 2,556,854 A | * 6/1951 | Spears et al. | 310/104 |
| 2,637,537 A | 5/1953 | Ernst | |
| 2,766,022 A | 10/1956 | Bender | |
| 2,809,021 A | * 10/1957 | Laden et al. | 366/142 |
| 2,833,576 A | 5/1958 | Cirone | |
| 2,991,161 A | 7/1961 | Gasche | |
| 2,996,363 A | 8/1961 | Ruyak | |
| 3,143,167 A | 8/1964 | Vieth | |
| 3,243,165 A | 3/1966 | Woody et al. | |
| 3,319,940 A | 5/1967 | Mentnech | |
| 3,326,610 A | 6/1967 | Baermann et al. | |
| 3,455,540 A | 7/1969 | Marcmann | |
| 3,456,923 A | 7/1969 | Zeuzem | |
| 3,539,117 A | * 11/1970 | Sjogren | 241/172 |
| 3,603,564 A | 9/1971 | Price et al. | |
| 3,622,968 A | 11/1971 | Silverman | |
| 3,643,695 A | * 2/1972 | Strah et al. | 137/614.04 |
| 3,676,653 A | 7/1972 | Phillips | |
| 3,680,843 A | 8/1972 | Lu et al. | |
| 3,693,941 A | 9/1972 | Suchy | |
| 3,697,053 A | 10/1972 | Will | |
| 3,718,032 A | 2/1973 | Gray | |
| 3,778,757 A | 12/1973 | Houston | |
| 3,909,647 A | 9/1975 | Peterson | |
| 4,037,826 A | 7/1977 | Hulslander et al. | |
| 4,065,107 A | 12/1977 | Van Horbek | |
| 4,106,825 A | 8/1978 | Ruyak | |
| 4,151,400 A | 4/1979 | Smith et al. | |
| 4,175,875 A | 11/1979 | Van Horbek | |
| 4,195,131 A | 3/1980 | Papas | |
| 4,199,265 A | 4/1980 | Sanderson et al. | |
| 4,229,110 A | 10/1980 | Lücke | |
| 4,235,592 A | 11/1980 | Smith et al. | |
| 4,247,792 A | * 1/1981 | Klicks et al. | 310/104 |
| 4,325,914 A | 4/1982 | Ruyak | |
| 4,355,906 A | 10/1982 | Ono | |
| 4,370,662 A | 1/1983 | Hou et al. | |
| 4,391,338 A | 7/1983 | Patashnick et al. | |
| 4,438,074 A | 3/1984 | Wilt | |
| 4,469,445 A | 9/1984 | Wurtz | |
| 4,506,982 A | 3/1985 | Smithers et al. | |
| 4,517,338 A | 5/1985 | Urdea et al. | |
| 4,568,195 A | 2/1986 | Herz et al. | |
| 4,594,228 A | 6/1986 | Lambert, Jr. et al. | |
| 4,598,049 A | 7/1986 | Zelinka et al. | |
| 4,640,023 A | 2/1987 | Mori et al. | |
| 4,671,941 A | 6/1987 | Niina et al. | |
| 4,675,026 A | 6/1987 | Riemer et al. | |
| 4,721,874 A | 1/1988 | Emmert | |
| 4,741,200 A | 5/1988 | Hammerle | |
| 4,746,490 A | 5/1988 | Saneii | |
| 4,748,002 A | 5/1988 | Neimark et al. | |
| 4,779,451 A | 10/1988 | Ezawa et al. | |
| 4,799,862 A | 1/1989 | Davidson et al. | |
| 4,810,099 A | 3/1989 | Langsetmo et al. | |
| 4,837,296 A | * 6/1989 | Heinz et al. | 528/125 |
| 4,858,637 A | 8/1989 | Rempel et al. | |
| 4,865,986 A | 9/1989 | Coy et al. | |
| 4,901,221 A | 2/1990 | Kodosky et al. | |
| 4,910,523 A | 3/1990 | Huguenin et al. | |
| 4,924,444 A | 5/1990 | Castellanos | |
| 4,924,716 A | 5/1990 | Schneider | |
| 4,983,046 A | 1/1991 | Murata et al. | |
| 4,985,190 A | * 1/1991 | Ishikawa et al. | 264/122 |
| 5,061,630 A | 10/1991 | Knopf et al. | |
| 5,074,671 A | 12/1991 | Roueche et al. | |
| 5,098,669 A | 3/1992 | Kawanami et al. | |
| 5,108,839 A | * 4/1992 | Lucke et al. | 428/408 |
| 5,117,550 A | 6/1992 | Nadeau et al. | |
| 5,143,854 A | 9/1992 | Pirrung et al. | |
| 5,145,255 A | 9/1992 | Shimada et al. | |
| 5,152,488 A | 10/1992 | Richardson | |
| 5,154,891 A | 10/1992 | Brenner | |
| 5,191,791 A | 3/1993 | Gerardi et al. | |
| 5,201,215 A | 4/1993 | Granstaff et al. | |
| 5,217,695 A | 6/1993 | Augustine et al. | |
| 5,224,174 A | 6/1993 | Schneider et al. | |
| RE34,386 E | 9/1993 | Davidson et al. | |
| 5,252,296 A | 10/1993 | Zuckermann et al. | |
| 5,291,587 A | 3/1994 | Kodosky et al. | |
| 5,297,867 A | 3/1994 | Holman | |
| 5,304,355 A | 4/1994 | Yant et al. | |
| 5,316,728 A | 5/1994 | Hayashi et al. | |
| 5,324,483 A | 6/1994 | Cody et al. | |
| 5,356,756 A | 10/1994 | Cavicchi et al. | |
| 5,357,964 A | 10/1994 | Spivey et al. | |
| 5,367,879 A | 11/1994 | Doke et al. | |
| 5,375,470 A | 12/1994 | Matsushima et al. | |
| 5,380,485 A | 1/1995 | Takahashi et al. | |
| 5,380,495 A | 1/1995 | Chang et al. | |
| 5,395,594 A | 3/1995 | Nokihara et al. | |
| 5,399,014 A | 3/1995 | Takata et al. | |
| 5,407,270 A | 4/1995 | Barile et al. | |
| 5,437,838 A | 8/1995 | DeMoranville et al. | |
| 5,439,236 A | 8/1995 | Musil | |
| 5,443,791 A | 8/1995 | Cathcart et al. | |
| 5,469,369 A | 11/1995 | Rose-Pehrsson et al. | |
| 5,472,278 A | 12/1995 | Kawaoka et al. | |
| 5,499,193 A | 3/1996 | Sugawara et al. | |
| 5,503,805 A | 4/1996 | Sugarman et al. | |
| 5,515,683 A | 5/1996 | Kessler | |
| 5,524,636 A | 6/1996 | Sarvazyan et al. | |
| 5,538,694 A | 7/1996 | Delius | |
| 5,541,314 A | 7/1996 | McGraw et al. | |
| 5,544,489 A | 8/1996 | Moren | |
| 5,546,301 A | 8/1996 | Agrawal et al. | |
| 5,576,946 A | 11/1996 | Bender et al. | |
| 5,593,642 A | 1/1997 | DeWitt et al. | |
| 5,593,839 A | 1/1997 | Hubbell et al. | |
| 5,601,141 A | 2/1997 | Gordon et al. | |
| 5,602,756 A | 2/1997 | Atwood et al. | |
| 5,609,826 A | 3/1997 | Cargill et al. | |
| 5,611,059 A | 3/1997 | Benton et al. | |
| 5,639,974 A | 6/1997 | Hanson et al. | |
| 5,670,269 A | * 9/1997 | Hamada et al. | |
| 5,698,163 A | 12/1997 | Mandel | |
| 5,714,127 A | 2/1998 | DeWitt et al. | |
| 5,716,584 A | 2/1998 | Baker et al. | |
| 5,732,277 A | 3/1998 | Kodosky et al. | |
| 5,734,098 A | 3/1998 | Kraus et al. | |
| 5,738,439 A | 4/1998 | Flower | |
| 5,746,982 A | 5/1998 | Saneii et al. | |
| 5,762,881 A | 6/1998 | Harness et al. | |
| 5,789,258 A | 8/1998 | Drinkwine et al. | |
| 5,802,856 A | 9/1998 | Schaper et al. | |
| 5,812,394 A | 9/1998 | Lewis et al. | |
| 5,819,842 A | 10/1998 | Potter et al. | |
| 5,841,959 A | 11/1998 | Guiremand | |
| 5,856,101 A | 1/1999 | Hubbell et al. | |
| 5,862,052 A | 1/1999 | Nixon et al. | |
| 5,866,342 A | 2/1999 | Antonenko et al. | |
| 5,871,278 A | 2/1999 | Harry et al. | |
| 5,882,601 A | 3/1999 | Kath et al. | |
| 5,888,830 A | 3/1999 | Mohan et al. | |
| 5,961,925 A | 10/1999 | Ruediger et al. | |
| 5,985,356 A | 11/1999 | Schultz et al. | |

| | | | |
|---|---|---|---|
| 6,030,917 A | | 2/2000 | Weinberg et al. |
| 6,045,755 A | * | 4/2000 | Lebl et al. ................... 422/65 |
| 6,063,633 A | | 5/2000 | Willson, III |
| 6,086,831 A | | 7/2000 | Harness et al. |
| 6,109,780 A | | 8/2000 | Lesniak |
| 6,132,686 A | | 10/2000 | Gallup et al. |
| 6,306,658 B1 | * | 10/2001 | Turner et al. ................ 436/37 |
| 6,455,316 B1 | * | 9/2002 | Turner et al. ................ 436/37 |

FOREIGN PATENT DOCUMENTS

| | | |
|---|---|---|
| EP | 0 529 504 A2 | 3/1993 |
| EP | 0 635 713 A1 | 1/1995 |
| EP | 0 783 922 A1 | 7/1997 |
| EP | 0 796 654 A2 | 9/1997 |
| EP | 0 963 791 A2 | 12/1999 |
| FR | 1418757 | 10/1965 |
| FR | 2630927 | 11/1989 |
| GB | 989424 | 4/1965 |
| GB | 1 408 199 | 10/1975 |
| GB | 1408199 | 10/1975 |
| JP | 61-69906 * | 4/1986 |
| JP | 2-16452 * | 1/1990 |
| JP | 4-18424 | 1/1992 |
| JP | 6-42302 * | 2/1994 |
| JP | 10182501 | 7/1998 |
| JP | 10-182501 | 7/1998 |
| WO | WO 95/23329 | 8/1995 |
| WO | WO 96/14930 | 5/1996 |
| WO | WO 97/09353 | 3/1997 |
| WO | WO98/07026 | 2/1998 |
| WO | WP 98/13137 | 4/1998 |
| WO | WO 98/15501 A2 | 4/1998 |
| WO | WO 98/15813 A1 | 4/1998 |
| WO | WO 98/39099 | 9/1998 |
| WO | WO 98/57740 | 12/1998 |
| WO | WO 9/30817 | 6/1999 |

OTHER PUBLICATIONS

Plazl, I. et al, Chemical Engineering Journal (Lausanne) 1995, 59, 253–257.*

Shellman, V. R. et al. Analytical Chemistry 1953, 25, 1285.*

Conrad, R. H. Analytical Chemistry 1967, 39, 1039.*

Rutkowski, W. et al, Chemia Analityczna (Warsaw, Poland) 1975, 20, 383–388.*

Mullin, J. W. et al, Chemistry & Industry (London, United Kingdom) 1978, 226–228.*

Salzman, R. N. et al, Chemical Engineering Progress 1991, 876, 39–44.*

Cole–Parmer Instrument Company Catalog, 1993–1994, p. 660.*

Aldrich Chemical Catalog 1988, pp. 2099–2110.*

Nelles, et al., For Development of Test Reactors for Heterogenic Solid–Liquid–Processes, Chem. Tech. 1975, pp. 714–716, vol. 27.

Salszman, et al., Structural Composite Mixers, Chemical Engineering Progress, Nov. 1988, pp. 50–55.

S. Vignes et al, Com. Rend. Congr. Indust. 1961, 405–411.

l. Kiezel et al, Chem. Stosow. 1968, 12, 407–415.

J. Nelles et al, Chem. Tech. 1975, 27, 714–716.

J. F. Cargill et al, Lab. Rob. Autom. 1996, 8, 139–148.

M. Salvet et al, Chem. Abstr. 1997, 126, abstract 20993h.

Takamatsu, T., et al., "Optimal Scheduling and Minimum Storage Tank Capacities in a Process System with Parallel Batch Units," Comput. Chem. Eng. 1979, 3, 185–195.

Gehrer, E., et al., "A Fully Programmable System for the Study of Catalytic Gas Reactions," J. Phys. E: Sci. Instrum. 1985, 18, 10, 836–838.

McFarlane, R.C., et al., "Adaptive Optimizing Control of Multivariable Constrained Chemical Processes. 2. Application Studies," Ind. Eng. Chem. Res. 1989, 28, 1834–1845.

Josses, P., et al., "Carrying Out Multiple Reactions in Organic Synthesis with a Robot," Adv. Lab. Autom. Rob. 1990, 6, 463–475.

Corkan, A., et al., "Design Concepts for Synthetic Chemistry Workstations," Adv. Lab. Autom. Rob. 1990, 6, 477–497.

Li, K.T., et al., Mixing and Control of a CSTR with Series–Parallel Reactions, J. Chin. Inst. Chem. Eng. 1991, 22, 61–69.

Lindsey, J.S., A Retrospective on the Automation of Laboratory Synthetic Chemistry, Chemom. Intell. Lab. Syst. 1992, 17, 15–45.

Plouvier, J.C., et al., "Experiment Planner for Strategic Experimentation with an Automated Chemistry Workstation," Chemom. Intell. Lab. Syst. 1992, 17–75–94.

Corkan, L.A., et al., "Application of an Automated Chemistry Workstation to Problems in Synthetic Chemistry," Chemom. Intell. Lab. Syst. 1992, 17 95–105.

Buhlmann, R., et al., "An Open Software Environment to Optimize the Productivity of Robotized Laboratories," J. Chromatogr. Sci. 1994, 32, 243–248.

Tietze, A., et al., "Temperature Oscillation Calorimetry in Stirred Tank Polymerization Reactors," Dechema Monogr. 1995, 131, 673–680.

Ahrweiler, P. et al., "Automation of Parallel Synthesis From Reagent Preparation Through Sample Workup," Am. Lab. 1997, 29, 12–14.

"Applications of the Piezoelectric Crystal Detector in Analytical Chemistry," J. Hlavay and G.G. Gullbault, Analytical Chemistry, vol. 49, No. 13, Nov. 1977.

"Electrolytic Determination of Nanomolar Concentrations of Silver in Solution with a Piezoelectric Quartz Crystal," T. Nomura and M. Iijima, Analytica Chemica Acta, vol. 131, pp. 97–102, 1981.

"The Oscillation Frequency of a Quartz Resonator in Contact with a Liquid," K. Keiji Kanazawa and Joseph G. Gordon, II, Analytica Chemica Acta, vol. 175, pp. 99–105, 1985.

"Computation of Equivalent Circuit Parameters of Quartz Crystals in Contact with Liquids and Study of Liquid Properties, Hiroshi Muramatsu," Eiichi Tamiya and Isao Karube, Analytical Chemistry, vol. 60, pp. 2142–2146, 1988.

"Netwrok Analysis Method Applied to Liquid–Phase Acoustic Wave Sensors," Analytical Chemistry, A.L. Kipling, M. Thomson, pp. 1514–1519, vol. 62, 1990.

"A Quartz Crystal Viscosity Sensor for Monitoring Coagulation Reaction and its Application to a Multichannel Coagulation Detector," H. Muramatsu, K. Kumura, T. Ataka, R. Homma, Y. Miura and I. Karube, Biosensors & Bioelectronics, vol. 6, pp. 353–358, 1991.

"Experiment Manager Software for an Automated Chemistry Workstation, Including a Scheduler for Parallel Experimentation," Corkan, et al., Chemometrics and Intelligent Laboratory Systems: Laboratory Information Management, 17 (1992) Oct., No. 1,47–74.

1 MHz quartz length extension resonator as a probe for scanning near–field acoustic microscopy, Thin Solid Films, A. Michels, F. Meinen, T. Mudfield, W. Gohde, U.C. Fischer, E. Beckmann and H. Fusch, vol. 264, pp. 172–195, 1995.

"Heated Reacto—Stations," Eastern Corporation, Oct. 1997.

"Microreactor Technology: Focusing the German Activities in this Novel and Promising Field of Chemical Process Engineering," J.P. Baselt, A. Forster. J. Herrmann, and D. Tiebes, pp. 13–17, 1997.

World Wide Web brinkmann.com 1997 "Brinkmann Horizon Stirrers and Hotplace Stirrers" information.

World Wide Web calbay.com Mar. 31, 1998 "Viscoliner" information.

World Wide Web argotech.com/quest May 18, 1998 "Nautilus 2400" information.

World Wide Web argotech.com/quest May 18, 1998 "Quest 210" information.

World Wide Web tecan.ch Jul. 14, 1998 "Cavro RSP 9000 Robotic Sample Processor" information.

World Wide Web thermometric.com/calorimetry Jul. 27, 1998 "Caliometry" information.

World Wide Web mettler.com Aug. 10, 1998 "Automatic Laboratory Reactors, Reaction Calorimeters and On–line Analysis" information.

World Wide Web calscorp.com/about_csc Feb. 8, 1999 "About Calorimetry Sciences Corp." information.

"MultiReactor—Reactor Block," RoboSynthon, Inc.

J–KEM ® Scientific, Inc. "Reaction Blocks" information.

Hazard Evaluation Laboratory Inc., *Affordable Reaction Calorimetry: Efficient Process Development and Hazard Assessment*, undated, 4 pages, Herts., England.

Hazard Evaluation Laboratory Inc., *Hel Auto–Lab: An Automated Reactor and General Purpose Control System*, undatd, 4 pages, Monmouth Junction, New Jersey, USA.

Hazard Evaluation Laboratory Inc., *Automated Batch Reactors: Bench Scale with Selected Features*, undated, 4 pages, Monmouth Junction, New Jersey, USA.

Hazard Evaluation Laboratory Inc., *HEL Newsletter*, Summer/Autumn 1993, 4 pages, Herts., England.

Hazard Evaluation Laboratory Inc., *HEL Newsletter*, Autumn/Winter 1999, 4 pages, Issue 7, Monmouth Junction, New Jersey, USA.

Hazard Evaluation Laboratory Inc., *HEL Newsletter*, Spring/Summer 2000, 4 pages, Issue 8, Monmouth Junction, New Jersey, USA.

Hazard Evaluation Laboratory Inc., *HEL Newsletter*, Autumn 2000, 4 pages, Issue 9, Lawrenceville, New Jersey, USA.

Hazard Evaluation Laboratory Inc., *High Pressure Chem–Scan for Rapid Chemical Reaction Scanning*, undated, 2 pages, Lawrenceville, New Jersey, USA.

Hazard Evaluation Laboratory Inc., *Process Development and Safety*, undated, 5 pages, New Jersey, USA.

Hazard Evaluation Laboratory Inc., *Process Development and Safety: Using Computer Controlled Reactors and Calorimeters*, undated, 2 pages, Monmouth Junction, New Jersey, USA.

Hazard Evaluation Laboratory Inc., *Reaction Calorimetry & Laboratory Automation*, undated, 1 page, Herts., England.

Hazard Evaluation Laboratory Inc., *Reaction Calorimetry*, undated, 3 pages.

Hazard Evaluation Laboratory Inc., *Reaction Calorimetry: Simular*, undated, 2 pages, Monmouth Junction, New Jersey, USA.

Hazard Evaluation Laboratory Inc., *Research Scale Reactor Automation: Auto–MATE*, undated, 4 pages, Monmouth Junction, New Jersey, USA.

Hazard Evaluation Laboratory Inc., *Introducing Tips: Tools for Integration of Process Systems*, undated, 1 page, New Jersey, USA.

Hazard Evaluation Laboratory Inc., *Miniature Multiple Reactor System: auto–MATE*, undated, 8 pages, Monmouth Junction, New Jersey, USA.

Hazard Evaluation Laboratory Inc., *Specify SIMULAR Around Your Chemistry*, undated, 5 pages, Lawrenceville, New Jersey, USA.

Hazard Evaluation Laboratory Inc., *First Amended Complaint with Jury Demand*, Jul. 31, 2002, 5 pages, New Jersey, USA.

Hazard Evaluation Laboratory Inc., *Answer to Counterclaim*, Sep. 9, 2002, 3 pages, New Jersey, USA.

Singh, Jasbir, *Thermal Analysis and Reaction Calorimetry*, undated, 3 pages.

Scientific Update, *The Evolution of a Revolution: Laboratory Automation in Chemical Process R& D*, Sep. 5, 1997, 3 pages, East Sussex, United Kingdom.

Singh, Jasbir, *Assessing Semi–Batch Reaction Hazards*, The Chemical Engineer, Feb. 25, 1993, 4 pages.

Singh, Jasbir, *Reation Calorimetry for Process Development: Recent Advances*, Process Safety Progress, Spring 1997, 7 pages.

Singh, Jasbir, *Automation of Reaction Research—An Alternative to Robotics*, European Pharmaceutical Contractor, Nov. 1997, 4 pages.

Singh, Jasbir, *Safe Scaleup of Exothermic Reactions*, Chemical Engineering, May 1997, 4 pages.

Singh, Jasbir, *Scaleable Automated Reactors*, undated ("Scaleable Automated Laboratory Reactors" title listed in reference 227 noted above), 13 pages, East.Sussex, United Kingdom.

Parr Instrument Company, *Stirred Reactors: Series 4520 Options*, undated, 3 pages.

SYMYX Technologies, Inc., Answer and Counterclaim, Aug. 30, 2002, 8 pages, New Jersey, USA.

SYMYX Technologies, Inc., First Amended Answer and Counterclaim, Oct. 30, 2002, 9 pages, New Jersey, USA.

Hazard Evaluation Laboratory Inc., Untitled Drawings, undated, 4 pages.

Waldram, Simon, et al., *Increasing the Scale of Process Operations: How to Identify Exothermic Reaction Hazards*, undated, 3 pages.

* cited by examiner

SECTION 1106

SECTION 1108

SECTION 1472

PARALLEL REACTOR WITH INTERNAL SENSING AND METHOD OF USING SAME

CROSS REFERENCE TO RELATED APPLICATIONS

This application is a divisional of U.S. application Ser. No. 09/548,848, filed Apr. 13, 2000 (now issued as U.S. Pat. No. 6,455,316), which is a continuation-in-part of U.S. application Ser. No. 09/239,223, filed Jan. 29, 1999 (now issued as U.S. Pat. No. 6,489,168), and a continuation-in-part of U.S. application Ser. No. 09/211,982, filed Dec. 14, 1998 (now issued as U.S. Pat. No. 6,306,658), which is a continuation in part of U.S. application Ser. No. 09/177,170, filed Oct. 22, 1998 (now issued as U.S. Pat. No. 6,548,026), which claims the benefit of U.S. Provisional Application No. 60/096,603, filed Aug. 13, 1998. All five of the foregoing applications are incorporated herein by reference in their entirety.

BACKGROUND OF THE INVENTION

1. Technical Field

The present invention relates to methods, devices, and computer programs for rapidly making, screening, and characterizing an array of materials in which process conditions are controlled and monitored.

2. Discussion

In combinatorial chemistry, a large number of candidate materials are created from a relatively small set of precursors and subsequently evaluated for suitability for a particular application. As currently practiced, combinatorial chemistry permits scientists to systematically explore the influence of structural variations in candidates by dramatically accelerating the rates at which they are created and evaluated. Compared to traditional discovery methods, combinatorial methods sharply reduce the costs associated with preparing and screening each candidate.

Combinatorial chemistry has revolutionized the process of drug discovery. One can view drug discovery as a two-step process: acquiring candidate compounds through laboratory synthesis or through natural products collection, followed by evaluation or screening for efficacy. Pharmaceutical researchers have long used high-throughput screening (HTS) protocols to rapidly evaluate the therapeutic value of natural products and libraries of compounds synthesized and cataloged over many years. However, compared to HTS protocols, chemical synthesis has historically been a slow, arduous process. With the advent of combinatorial methods, scientists can now create large libraries of organic molecules at a pace on par with HTS protocols.

Recently, combinatorial approaches have been used for discovery programs unrelated to drugs. For example, some researchers have recognized that combinatorial strategies also offer promise for the discovery of inorganic compounds such as high-temperature superconductors, magnetoresistive materials, luminescent materials, and catalytic materials. See, for example, co-pending U.S. patent application Ser. No. 08/327,513 "The Combinatorial Synthesis of Novel Materials" (published as WO 96/11878) and co-pending U.S. patent application Ser. No. 08/898,715 "Combinatorial Synthesis and Analysis of Organometallic Compounds and Catalysts" (published, in part, as WO 98/03251), which are all herein incorporated by reference.

Because of its success in eliminating the synthesis bottleneck in drug discovery, many researchers have come to narrowly view combinatorial methods as tools for creating structural diversity. Few researchers have emphasized that, during synthesis, variations in temperature, pressure, ionic strength, and other process conditions can strongly influence the properties of library members. For instance, reaction conditions are particularly important in formulation chemistry, where one combines a set of components under different reaction conditions or concentrations to determine their influence on product properties.

Moreover, because the performance criteria in materials science is often different than in pharmaceutical research, many workers have failed to realize that process variables often can be used to distinguish among library members both during and after synthesis. For example, the viscosity of reaction mixtures can be used to distinguish library members based on their ability to catalyze a solution-phase polymerization—at constant polymer concentration, the higher the viscosity of the solution, the greater the molecular weight of the polymer formed. Furthermore, total heat liberated and/or peak temperature observed during an exothermic reaction can be used to rank catalysts.

Therefore, a need exists for an apparatus to prepare and screen combinatorial libraries in which one can monitor and control process conditions during synthesis and screening.

SUMMARY OF THE INVENTION

The present invention generally provides an apparatus for parallel processing of reaction mixtures. The apparatus includes vessels for containing the reaction mixtures, a stirring system, and a temperature control system that is adapted to maintain individual vessels or groups of vessels at different temperatures. The apparatus may consist of a monolithic reactor block, which contains the vessels, or an assemblage of reactor block modules. A robotic material handling system can be used to automatically load the vessels with starting materials. In addition to heating or cooling individual vessels, the entire reactor block can be maintained at a nearly uniform temperature by circulating a temperature-controlled thermal fluid through channels formed in the reactor block. The stirring system generally includes stirring members—blades, bars, and the like— placed in each of the vessels, and a mechanical or magnetic drive mechanism. Torque and rotation rate can be controlled and monitored through strain gages, phase lag measurements, and speed sensors.

The apparatus may optionally include a system for evaluating material properties of the reaction mixtures. The system includes mechanical oscillators located within the vessels. When stimulated with a variable-frequency signal, the mechanical oscillators generate response signals that depend on properties of the reaction mixture. Through calibration, mechanical oscillators can be used to monitor molecular weight, specific gravity, elasticity, dielectric constant, conductivity, and other material properties of the reaction mixtures.

The present invention also provides an apparatus for monitoring rates of production or consumption of a gas-phase component of a reaction mixture. The apparatus generally comprises a closed vessel for containing the reaction mixture, a stirring system, a temperature control system and a pressure control system. The pressure control system includes a pressure sensor that communicates with the vessel, as well as a valve that provides venting of a gaseous product from the vessel. In addition, in cases where a gas-phase reactant is consumed during reaction, the valve provides access to a source of the reactant. Pressure monitoring of the vessel, coupled with venting of product or filling with reactant allows the investigator to determine rates of production or consumption, respectively.

One aspect of the present invention provides an apparatus for monitoring rates of consumption of a gas-phase reactant. The apparatus generally comprises a closed vessel for containing the reaction mixture, a stirring system, a temperature control system and a pressure control system. The pressure control system includes a pressure sensor that communicates with the vessel, as well as a flow sensor that monitors the flow rate of reactant entering the vessel. Rates of consumption of the reactant can be determined from the reactant flow rate and filling time.

The present invention also provides a method of making and characterizing a plurality of materials. The method includes the steps of providing vessels with starting materials to form reaction mixtures, confining the reaction mixtures in the vessels to allow the reaction to occur, and stirring the reaction mixtures for at least a portion of the confining step. The method further includes the step of evaluating the reaction mixtures by tracking at least one characteristic of the reaction mixtures for at least a portion of the confining step. Various characteristics or properties can be monitored during the evaluating step, including temperature, rate of heat transfer, conversion of starting materials, rate of conversion, torque at a given stirring rate, stall frequency, viscosity, molecular weight, specific gravity, elasticity, dielectric constant, and conductivity.

One aspect of the present invention provides a method of monitoring the rate of consumption of a gas-phase reactant. The method comprises the steps of providing a vessel with starting materials to form the reaction mixture, confining the reaction mixtures in the vessel to allow reaction to occur, and stirring the reaction mixture for at least a portion of the confining step. The method further includes filling the vessel with the gas-phase reactant until gas pressure in the vessel exceeds an upper-pressure limit, $P_H$, and allowing gas pressure in the vessel to decay below a lower-pressure limit, $P_L$. Gas pressure in the vessel is monitored and recorded during the addition and consumption of the reactant. This process is repeated at least once, and rates of consumption of the gas-phase reactant in the reaction mixture are determined from the pressure versus time record.

Another aspect of the present invention provides a method of monitoring the rate of production of a gas-phase product. The method comprises the steps of providing a vessel with starting materials to form the reaction mixture, confining the reaction mixtures in the vessel to allow reaction to occur, and stirring the reaction mixture for at least a portion of the confining step. The method also comprises the steps of allowing gas pressure in the vessel to rise above an upper-pressure limit, $P_H$, and venting the vessel until gas pressure in the vessel falls below a lower-pressure limit, $P_L$. The gas pressure in the vessel is monitored and recorded during the production of the gas-phase component and subsequent venting of the vessel. The process is repeated at least once, so rates of production of the gas-phase product can be calculated from the pressure versus time record.

The present invention provides an apparatus for parallel processing of reaction mixtures comprising vessels for containing the reaction mixtures, a stirring system for agitating the reaction mixtures, a temperature control system for regulating the temperature of the reaction mixtures, and a fluid injection system. The vessels are sealed to minimize unintentional gas flow into or out of the vessels, and the fluid injection system allows introduction of a liquid into the vessels at a pressure different than ambient pressure. The fluid injection system includes fill ports that are adapted to receive a liquid delivery probe, such as a syringe or pipette, and also includes conduits, valves, and tubular injectors. The conduits provide fluid communication between the fill ports and the valves and between the valves and the injectors. The injectors are located in the vessels, and can have varying lengths, depending on whether fluid injection is to occur in the reaction mixtures or in the vessel headspace above the reaction mixtures. Generally, a robotic material handling system manipulates the fluid delivery probe and controls the valves. The injection system can be used to deliver gases, liquids, and slurries, e.g., catalysts on solid supports.

One aspect of the present invention provides an apparatus for parallel processing of reaction mixtures comprising sealed vessels, a temperature control system, and a stirring system having a magnetic feed through device for coupling an external drive mechanism with a spindle that is completely contained within one of the vessels. The magnetic feed through device includes a rigid pressure barrier having a cylindrical interior surface that is open along the base of the pressure barrier. The base of the pressure barrier is attached to the vessel so that the interior surface of the pressure barrier and the vessel define a closed chamber. The magnetic feed through device further includes a magnetic driver that is rotatably mounted on the rigid pressure barrier and a magnetic follower that is rotatably mounted within the pressure barrier. The drive mechanism is mechanically coupled to the magnetic driver, and one end of the spindle is attached to a leg portion of the magnetic follower that extends into the vessel headspace. Since the magnetic driver and follower are magnetically coupled, rotation of the magnetic driver induces rotation of the magnetic follower and spindle.

Another aspect of the present invention provides an apparatus for parallel processing of reaction mixtures comprising sealed vessels, a temperature control system, and a stirring system that includes multi-piece spindles that are partially contained in the vessels. Each of the spindles includes an upper spindle portion that is mechanically coupled to a drive mechanism, a removable stirrer contained in one of the vessels, and a coupler for reversibly attaching the removable stirrer to the upper spindle portion. The removable stirrer is made of a chemically resistant plastic material, such as polyethylethylketone or polytetrafluoroethylene, and is typically discarded after use.

The exact combination of parallel processing features depends on the embodiment of the invention being practiced. In some aspects, the present invention provides an apparatus for parallel processing of reaction mixtures comprising sealed vessels and an injection system. The present invention also provides an apparatus for parallel processing of reaction mixtures comprising sealed vessels, an injection system and a stirring system. The present invention also provides an apparatus for parallel processing of reaction mixtures comprising vessels having a temperature control system and a stirring system. The present invention also provides an apparatus for parallel processing of reaction mixtures comprising sealed vessels and a pressure control system. The present invention also provides an apparatus for parallel processing of reaction mixtures comprising sealed vessels, an injection system and a system for property or characteristic monitoring.

The present invention also provides computer programs and computer-implemented methods for monitoring the progress and properties of parallel chemical reactions. In one aspect, the invention features a method of monitoring a combinatorial chemical reaction. The method includes (a)

receiving a measured value associated with the contents of each of a plurality of reactor vessels; (b) displaying the measured values; and (c) repeating steps (a) and (b) multiple times over the course of the combinatorial chemical reaction.

Implementations of the invention can include one or more of the following advantageous features. The measured values include a set of values for a number of reaction conditions associated with each of the reactor vessels. Step (c) is performed at a predetermined sampling rate. The method also includes changing a reaction parameter associated with one of the reactor vessels in response to the measured value to maintain the reactor vessel at a predetermined set point. Reaction parameters include temperature, pressure, and motor (stirring) speed. The method also includes quenching a reaction in one of the reactor vessels in response to the measured value associated with the contents of the reactor vessel. The method also includes using the measured value to calculate an experimental variable or value for one of the reactor vessels. Examples of experimental variables include rates of change of temperature or pressure, percent conversion of a starting material, and viscosity. The method also includes displaying the experimental variable.

In general, in another aspect, the invention features a method for controlling a combinatorial chemical reactor including multiple reactor vessels, each containing a reaction environment. The method includes receiving a set point for a property associated with each vessel's reaction environment; measuring a set of experimental values for the property for each vessel; displaying the set of experimental values; and changing the reaction environment in one or more of the plurality of reactor vessels in response to the set point and a change in one or more of the set of experimental values. For example, the method may terminate a reaction (change the reaction environment) in response to reactant conversion (experimental value) indicating that a target conversion (set point) has been reached. During reaction, a graphical representation of the set of experimental values is displayed, often as a histogram.

In general, in another aspect, the invention features a computer program on a computer-readable medium for monitoring a combinatorial chemical reaction. The program includes instructions to (a) receive a measured value associated with the contents of each of a plurality of reactor vessels, instructions to (b) display the measured values, and instructions to (c) repeat steps (a) and (b) multiple times during the course of the combinatorial chemical reaction. The computer program includes instructions to change a reaction parameter associated with one of the reactor vessels in response to the measured value to maintain the reactor vessel at a predetermined set point.

In general, in another aspect, the invention features a reactor control system for monitoring and controlling parallel chemical reactions. The reactor system includes a system control module for providing control signals to a parallel chemical reactor including multiple reactor vessels, a mixing monitoring and control system, a temperature monitoring and control system, and a pressure monitoring and control system. The reactor system also includes a data analysis module for receiving a set of measured values from the parallel chemical reactor and for calculating one or more calculated values for each of the reactor vessels. In addition, the reactor control system includes a user interface module for receiving reaction parameters and for displaying the set of measured values and calculated values.

Advantages that can be seen in implementations of the invention include one or more of the following. Process variables can be monitored and controlled for multiple elements in a combinatorial library as a chemical reaction progresses. Data can be extracted for each library element repeatedly and in parallel over the course of the reaction, instead of extracting only a limited number of data points for selected library elements. Calculations and corrections can be applied automatically to every available data point for every library element over the course of the reaction. A single experimental value can be calculated from the entire data set for each library element.

A further understanding of the nature and advantages of the present invention may be realized by reference to the remaining portions of the specification, drawings, and claims.

DETAILED DESCRIPTION OF THE PREFERRED EMBODIMENTS

Figure 1:
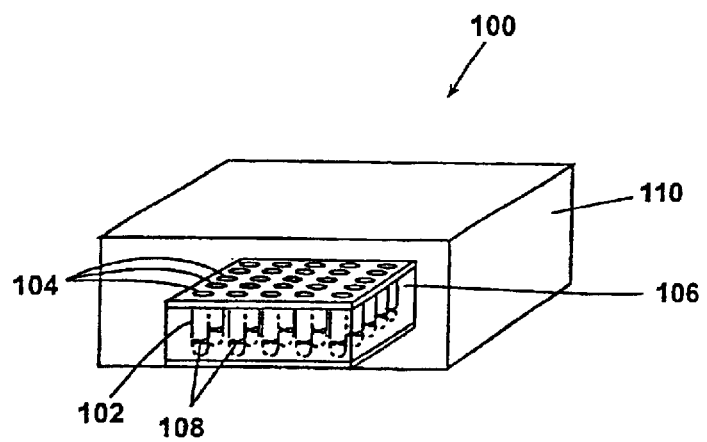
FIG. 1 illustrates a parallel reactor system in accordance with the present invention.

The present invention provides an apparatus, methods, and computer programs for carrying out and monitoring the progress and properties of multiple reactions in situ. It is especially useful for synthesizing, screening, and characterizing combinatorial libraries, but offers significant advantages over conventional experimental reactors as well. For example, in situ monitoring of individual reaction mixtures not only provides feedback for process controllers, but also provides data for determining reaction rates, product yields, and various properties of the reaction products, including viscosity and molecular weight during an experiment. Moreover, in situ monitoring coupled with tight process control can improve product selectivity, provide opportunities for process and product optimization, allow processing of temperature-sensitive materials, and decrease experimental variability.

Other advantages result from using small mixture volumes. In addition to conserving valuable reactants, decreasing sample size increases surface area relative to volume within individual reactor vessels. This improves the uniformity of reaction mixtures, aids gas-liquid exchange in multiphase reactions, and increases heat transfer between the samples and the reactor vessels. Because large samples respond much slower to changes in system conditions, the use of small samples, along with in situ monitoring and process control, also allows for time-dependent processing and characterization.

The parallel reactor of this invention is useful for the research and development of chemical reactions, catalysts and processes. The same type of reaction may be preformed in each vessel or different reactions may be performed in each vessel. Thus, each reaction vessel may vary with regard to its contents during an experiment. Each reaction vessel can vary by a process condition, including catalyst amounts (volume, moles or mass), ratios of starting components, time for reaction, reaction temperature, reaction pressure, rate of reactant addition to the reaction, reaction atmosphere, reaction stir rate, injection of a catalyst or reactant or other component (e.g., a reaction quencher) and other conditions that those of skill in the art will recognize. Each reaction vessel can also vary by the chemicals present, such as by using different reactants or catalysts in two or more vessels.

For example, the parallel reactor of this invention may have reaction vessels that are of different volume. The reactor vessel volume may vary from about 0.1 milliliter (ml) to about 500 ml, more particularly from about 1 ml to about 100 ml and even more particularly from about 5 ml to about 20 ml. These reactor vessel sizes allow for reactant volumes in a range that functionally allow for proper stirring (e.g., a 15 ml reactor vessel allows for reactant volumes of between about 2–10 ml). Also, the parallel reactor of this invention allows the reactor pressure to vary from vessel to vessel or module to module or cell to cell, with each vessel being at a pressure in the range of from about atmospheric pressure to about 500 psi and more particularly in the range of from atmospheric to about 300 psi. In still other embodiments, the reactor temperature may vary from vessel to vessel or module to module or cell to cell, with each vessel being at a temperature in the range of from about −150° C. to about 250° C. and more particularly in the range of from −100° C. to about 200° C. The stirring rates may also vary from vessel to vessel or module to module or cell to cell, with each vessel being stirred by mechanical stirring at a rate of from about 0 to about 3000 revolutions per minute (rpm) and more particularly at a rate of from about 10 to about 2000 rpm and even more particularly at a rate of from about 100 to about 1000 rpm. In other embodiments, the parallel reactor of this invention allows for the injection of reactants or other components (such as catalysts) while a reactor vessel is at reaction pressure (as discussed in detail below). Generally, the injection of reactants or components allows for the reaction conditions to be varied from vessel to vessel, such as by adding a reaction quencher at a timed frequency or a conversion frequency. Reaction times can vary depending on the experiment being performed, but may be in the range from less than one minute to about 48 hours, more particularly in the range of from about one minute to about 24 hours and even more particularly in the range of from about 5 minutes to about 12 hours.

Overview of Parallel Reactor

The parallel reactor system of the present invention is an integrated platform for effecting combinatorial research in chemistry and materials science applications. An integrated parallel reactor system comprises a plurality of reactors that can be operated in parallel on a scale suitable for research applications—typically bench scale or smaller scale (e.g., mini-reactors and micro-reactors). The reactors of such an integrated system can typically, but not necessarily, be formed in, be integral with or be linked by a common substrate, be arranged in a common plane, preferably with spatial uniformity, and/or can share a common support structure or housing. The integrated parallel reactor system can also include one or more control and monitoring systems that are fully or partially integral therewith.

FIG. 1 shows one embodiment of a parallel reactor system 100. The reactor system 100 includes removable vessels 102 for receiving reactants. Wells 104 formed into a reactor block 106 contain the vessels 102. Although the wells 104 can serve as reactor vessels, removable vessels 102 or liners provide several advantages. For example, following reaction and preliminary testing (screening), one can remove a subset of vessels 102 from the reactor block 106 for further in-depth characterization. When using removable vessels 102, one can also select vessels 102 made of material appropriate for a given set of reactants, products, and reaction conditions. Unlike the reactor block 106, which represents a significant investment, the vessels 102 can be discarded if damaged after use. Finally, one can lower system 100 costs and ensure compatibility with standardized sample preparation and testing equipment by designing the reactor block 106 to accommodate commercially available vessels.

As shown in FIG. 1, each of the vessels 102 contains a stirring blade 108. In one embodiment, each stirring blade 108 rotates at about the same speed, so that each of the reaction mixtures within the vessels 102 experience similar mixing. Because reaction products can be influenced by mixing intensity, a uniform rotation rate ensures that any differences in products does not result from mixing variations. In another embodiment, the rotation rate of each stirring blade 108 can be varied independently, which as discussed below, can be used to characterize the viscosity and molecular weight of the reaction products or can be used to study the influence of mixing speed on reaction.

Depending on the nature of the starting materials, the types of reactions, and the method used to characterize reaction products and rates of reaction, it may be desirable to enclose the reactor block 106 in a chamber 110. The chamber 110 may be evacuated or filled with a suitable gas. In some cases, the chamber 110 may be used only during the loading of starting materials into the vessels 102 to minimize contamination during sample preparation, for example, to prevent poisoning of oxygen sensitive catalysts. In other cases, the chamber 110 may be used during the reaction process or the characterization phase, providing a convenient method of supplying one or more gases to all of the vessels 102 simultaneously. In this way, a gaseous reactant can be added to all of the vessels 102 at one time. Note, however, it is often necessary to monitor the rate of disappearance of a gaseous reactant—for example, when determining rates of conversion—and in such cases the vessels 102 are each sealed and individually connected to a gas source, as discussed below.

Figure 2:
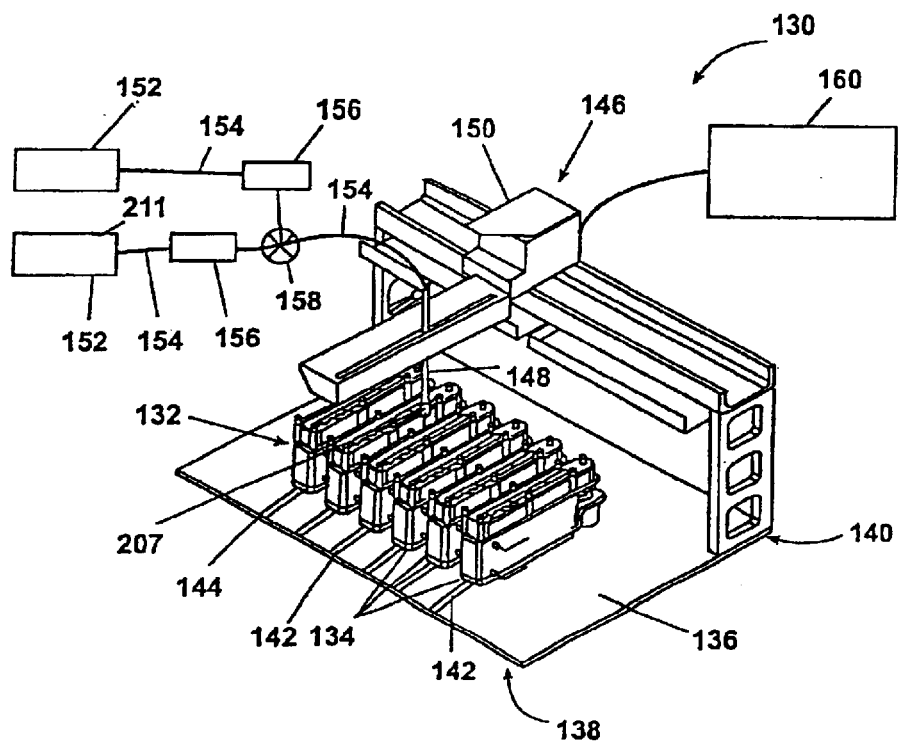
FIG. 2 shows a perspective view of a modular reactor block with a robotic liquid handling system.

FIG. 2 shows a perspective view of a parallel reactor system 130 comprised of a modular reactor block 132. The modular reactor block 132 shown in FIG. 2 consists of six modules 134, and each module 134 contains eight vessels (not shown). Note, however, the number of modules 134 and the number of vessels within each of the modules 134 can vary. In some embodiments, a module 134 may be broken down into component cells (not shown), for example with each cell containing one well 104 holding a reaction vessel 102. Thus, if a module is to contain eight reaction vessels, there may be eight cells, which facilitates lower cost manufacturing as well as replacement of damaged or worn cells. There may any number of cells per module, such as cell that contains two reaction vessels per cell, etc.

The use of modules 134 offers several advantages over a monolithic reactor block. For example, the size of the reactor block 132 can be easily adjusted depending on the number of reactants or the size of the combinatorial library. Also, relatively small modules 134 are easier to handle, transport, and fabricate than a single, large reactor block. A damaged module can be quickly replaced by a spare module, which minimizes repair costs and downtime. Finally, the use of modules 134 improves control over reaction parameters. For instance, stirring speed, temperature, and pressure of each of the vessels can be varied between modules.

In the embodiment shown in FIG. 2, each of the modules 134 is mounted on a base plate 136 having a front 138 and a rear 140. The modules 134 are coupled to the base plate 136 using guides (not shown) that mate with channels 142 located on the surface of the base plate 136. The guides prevent lateral movement of the modules 134, but allow linear travel along the channels 142 that extend from the front 138 toward the rear 140 of the base plate 136. Stops 144 located in the channels 142 near the front 138 of the base plate 136 limit the travel of the modules 134. Thus, one or more of the modules 134 can be moved towards the front 138 of the base plate 136 to gain access to individual vessels while the other modules 134 undergo robotic filling. In another embodiment, the modules 134 are rigidly mounted to the base plate 136 using bolts, clips, or other fasteners.

As illustrated in FIG. 2, a conventional robotic material handling system 146 is ordinarily used to load vessels with starting materials. The robotic system 146 includes a pipette or probe 148 that dispenses measured amounts of liquids into each of the vessels. The robotic system 146 manipulates the probe 148 using a 3-axis translation system 150. The probe 148 is connected to sources 152 of liquid reagents through flexible tubing 154. Pumps 156, which are located along the flexible tubing 154, are used to transfer liquid reagents from the sources 152 to the probe 148. Suitable pumps 156 include peristaltic pumps and syringe pumps. A multi-port valve 158 located downstream of the pumps 156 selects which liquid reagent from the sources 152 is sent to the probe 148 for dispensing in the vessels.

The robotic fluid handling system 146 is controlled by a processor 160. In the embodiment shown in FIG. 2, the user first supplies the processor 160 with operating parameters using a software interface. Typical operating parameters include the coordinates of each of the vessels and the initial compositions of the reaction mixtures in individual vessels. The initial compositions can be specified as lists of liquid reagents from each of the sources 152, or as incremental additions of various liquid reagents relative to particular vessels.

Temperature Control and Monitoring

The ability to monitor and control the temperature of individual reactor vessels is an important aspect of the present invention. During synthesis, temperature can have a profound effect on structure and properties of reaction products. For example, in the synthesis of organic molecules, yield and selectivity often depend strongly on temperature. Similarly, in polymerization reactions, polymer structure and properties—molecular weight, particle size, monomer conversion, microstructure—can be influenced by reaction temperature. During screening or characterization of combinatorial libraries, temperature control and monitoring of library members is often essential to making meaningful comparisons among members. Finally, temperature can be used as a screening criteria or can be used to calculate useful process and product variables. For instance, catalysts of exothermic reactions can be ranked based on peak reaction temperature and/or total heat released over the course of reaction, and temperature measurements can be used to compute rates of reaction and conversion.

Figure 3:
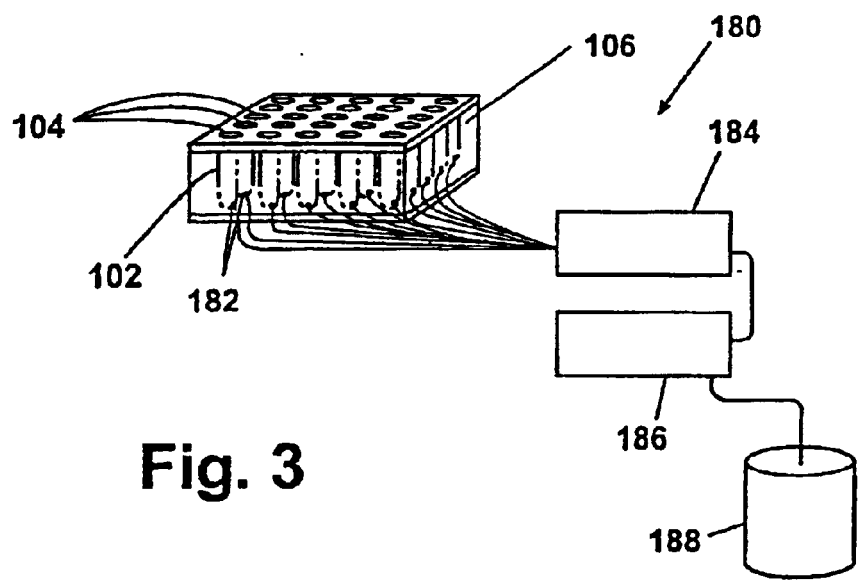
FIG. 3 shows a temperature monitoring system.

FIG. 3 illustrates one embodiment of a temperature monitoring system 180, which includes temperature sensors 182 that are in thermal contact with individual vessels 102. For clarity, we describe the temperature monitoring system 180 with reference to the monolithic reactor block 106 of FIG. 1, but this disclosure applies equally well to the modular reactor block 132 of FIG. 2. Suitable temperature sensors 182 include jacketed or non-jacketed thermocouples (TC), resistance thermometric devices (RTD), and thermistors. The temperature sensors 182 communicate with a temperature monitor 184, which converts signals received from the temperature sensors 182 to a standard temperature scale. An optional processor 186 receives temperature data from the temperature monitor 184. The processor 186 performs calculations on the data, which may include wall corrections and simple comparisons between different vessels 102, as well as more involved processing such as calorimetry calculations discussed below. During an experimental run, temperature data is typically sent to storage 188 so that it can be retrieved at a later time for analysis.

Figure 4:
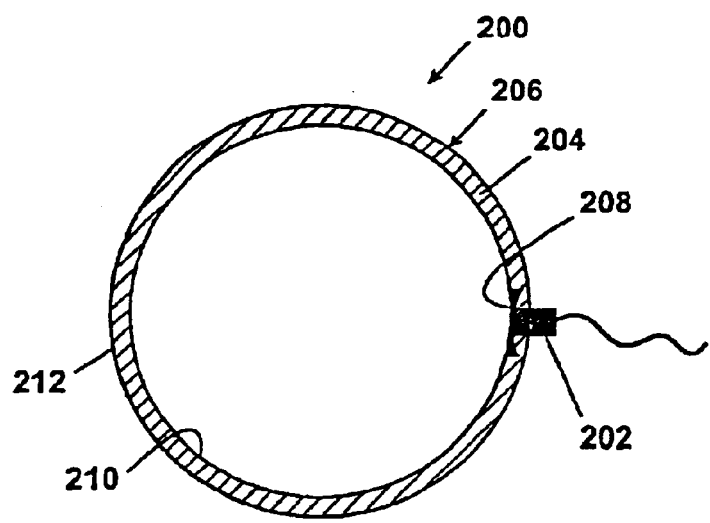
FIG. 4 shows a cross-sectional view of an integral temperature sensor-vessel assembly.

FIG. 4 shows a cross-sectional view of an integral temperature sensor-vessel assembly 200. The temperature sensor 202 is embedded in the wall 204 of a reactor vessel 206. The surface 208 of the temperature sensor 202 is located adjacent to the inner wall 210 of the vessel to ensure good thermal contact between the contents of the vessel 206 and the temperature sensor 202. The sensor arrangement shown in FIG. 3 is useful when it is necessary to keep the contents of the reactor vessel 206 free of obstructions. Such a need might arise, for example, when using a freestanding mixing device, such as a magnetic stirring bar. Note, however, that fabricating an integral temperature sensor such as the one shown in FIG. 4 can be expensive and time consuming, especially when using glass reactor vessels.

Thus, in another embodiment, the temperature sensor is immersed in the reaction mixture. Because the reaction environment within the vessel may rapidly damage the temperature sensor, it is usually jacketed with an inert material, such as a fluorinated thermoplastic. In addition to low cost, direct immersion offers other advantages, including rapid response and improved accuracy. In still another embodiment, the temperature sensor is placed on the outer surface 212 of the reactor vessel of FIG. 4. As long as the thermal conductivity of the reactor vessel is known, relatively accurate and rapid temperature measurements can be made.

Figure 5:
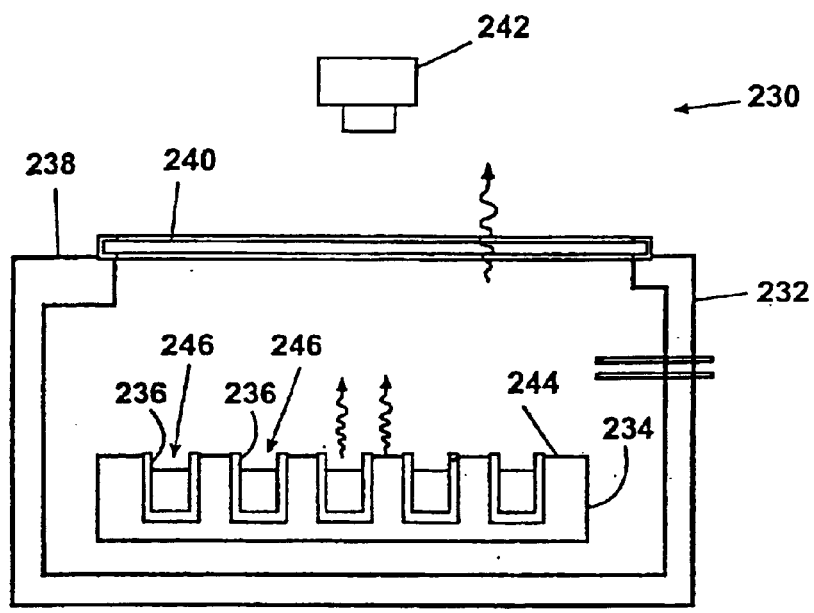
FIG. 5 shows a side view of an infrared temperature measurement system.

One can also remotely monitor temperature using an infrared system illustrated in FIG. 5. The infrared monitoring system 230 comprises an optional isolation chamber 232, which contains the reactor block 234 and vessels 236. The top 238 of the chamber 232 is fitted with a window 240 that is transparent to infrared radiation. An infrared-sensitive camera 242 positioned outside the isolation chamber 232, detects and records the intensity of infrared radiation passing through the window 240. Since infrared emission intensity depends on source temperature, it can be used to distinguish high temperature vessels from low temperature vessels. With suitable calibration, infrared intensity can be converted to temperature, so that at any given time, the camera 242 provides "snapshots" of temperature along the surface 244 of the reactor block 234. In the embodiment shown in FIG. 5, the tops 246 of the vessels 236 are open. In an alternate embodiment, the tops 246 of the vessels 236 are fitted with infrared transparent caps (not shown). Note that, with stirring, the temperature is uniform within a particular vessel, and therefore the surface temperature of the vessel measured by infrared emission will agree with the bulk temperature measured by a TC or RTD immersed in the vessel.

The temperature of the reactor vessels and block can be controlled as well as monitored. Depending on the application, each of the vessels can be maintained at the same temperature or at different temperatures during an experiment. For example, one may screen compounds for catalytic activity by first combining, in separate vessels, each of the compounds with common starting materials; these mixtures are then allowed to react at uniform temperature. One may then further characterize a promising catalyst by combining it in numerous vessels with the same starting materials used in the screening step. The mixtures then react at different temperatures to gauge the influence of temperature on catalyst performance (speed, selectivity). In many instances, it may be necessary to change the temperature of the vessels during processing. For example, one may decrease the temperature of a mixture undergoing a reversible exothermic reaction to maximize conversion. Or, during a characterization step, one may ramp the temperature of a reaction product to detect phase transitions (melting range, glass transition temperature). Finally, one may maintain the reactor block at a constant temperature, while monitoring temperature changes in the vessels during reaction to obtain calorimetric data as described below.

Figure 6:
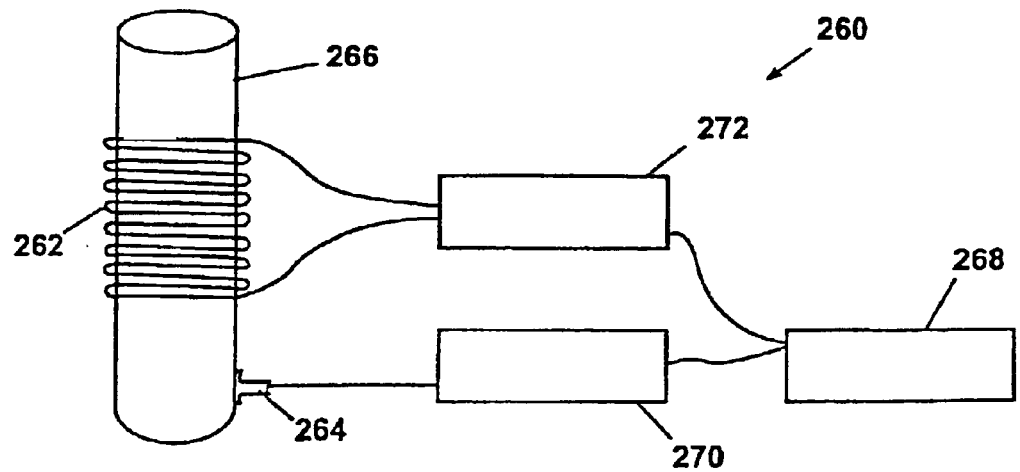
FIG. 6 shows a temperature monitoring and control system for a reactor vessel.

FIG. 6 shows a useful temperature control system 260, which comprises separate heating 262 and temperature sensing 264 elements. The heating element 262 shown in FIG. 6 is a conventional thin filament resistance heater whose heat output is proportional to the product of the filament resistance and the square of the current passing through the filament. The heating element 262 is shown coiled around a reactor vessel 266 to ensure uniform radial and axial heating of the vessel 266 contents. The temperature sensing element 264 can be a TC, RTD, and the like. The heating element 262 communicates with a processor 268, which based on information received from the temperature sensor 264 through a temperature monitoring system 270, increases or decreases heat output of the heating element 262. A heater control system 272, located in the communication path between the heating element 262 and the processor 268, converts a processor 268 signal for an increase (decrease) in heating into an increase (decrease) in electrical current through the heating element 262. Generally, each of the vessels 104 of the parallel reactor system 100 shown in FIG. 1 or FIG. 3 are equipped with a heating element 262 and one or more temperature sensors 264, which communicate with a central heater control system 272, temperature monitoring system 270, and processor 268, so that the temperature of the vessels 104 can be controlled independently.

Other embodiments include placing the heating element 262 and temperature sensor 264 within the vessel 266, which results in more accurate temperature monitoring and control of the vessel 266 contents, and combining the temperature sensor and heating element in a single package. A thermistor is an example of a combined temperature sensor and heater, which can be used for both temperature monitoring and control because its resistance depends on temperature.

Figure 7:
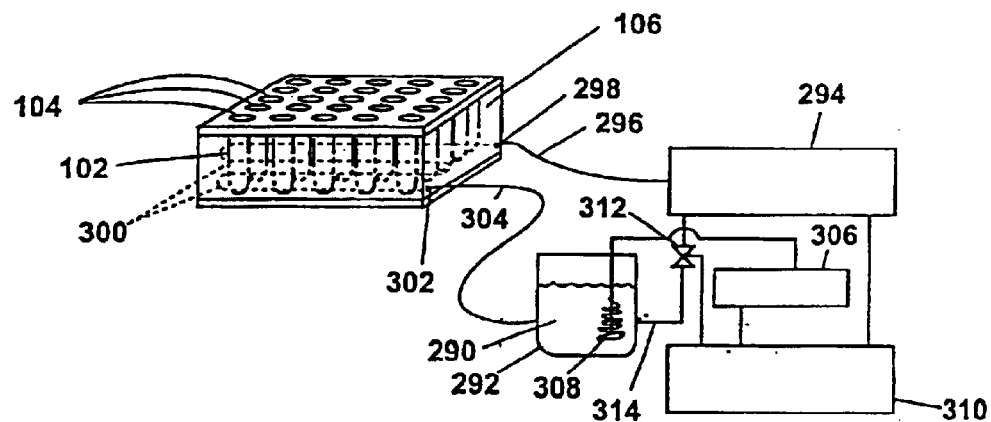
FIG. 7 illustrates another temperature control system, which includes liquid cooling and heating of the reactor block.
Figure 8:
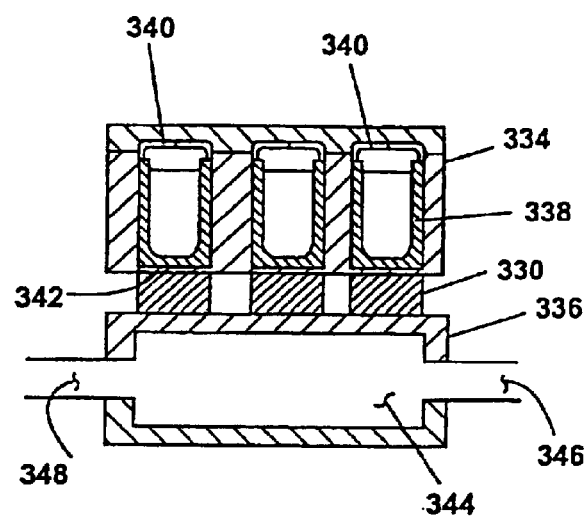
FIG. 8 is a cross-sectional view of thermoelectric devices sandwiched between a reactor block and heat transfer plate.

FIG. 7 illustrates another temperature control system, which includes liquid cooling and heating of the reactor block 106. Regulating the temperature of the reactor block 106 provides many advantages. For example, it is a simple way of maintaining nearly uniform temperature in all of the reactor vessels 102. Because of the large surface area of the vessels 102 relative to the volume of the reaction mixture, cooling the reactor block 106 also allows one to carryout highly exothermic reactions. When accompanied by temperature control of individual vessels 102, active cooling of the reactor block 106 allows for processing at sub-ambient temperatures. Moreover, active heating or cooling of the reactor block 106 combined with temperature control of individual vessels 102 or groups of vessels 102 also decreases response time of the temperature control feedback. One may control the temperature of individual vessels 102 or groups of vessels 102 using compact heat transfer devices, which include electric resistance heating elements or thermoelectric devices, as shown in FIG. 6 and FIG. 8, respectively. Although we describe reactor block cooling with reference to the monolithic reactor block 106, one may, in a like manner, independently heat or cool individual modules 134 of the modular reactor block 132 shown in FIG. 2.

Returning to FIG. 7, a thermal fluid 290, such as water, steam, a silicone fluid, a fluorocarbon, and the like, is transported from a uniform temperature reservoir 292 to the reactor block 106 using a constant or variable speed pump 294. The thermal fluid 290 enters the reactor block 106 from a pump outlet conduit 296 through an inlet port 298. From the inlet port 298, the thermal fluid 290 flows through a passageway 300 formed in the reactor block 106. The passageway may comprise single or multiple channels. The passageway 300 shown in FIG. 7, consists of a single channel that winds its way between rows of vessels 102, eventually exiting the reactor block 106 at an outlet port 302. The thermal fluid 290 returns to the reservoir 292 through a reactor block outlet conduit 304. A heat pump 306 regulates the temperature of the thermal fluid 290 in the reservoir 292 by adding or removing heat through a heat transfer coil 308. In response to signals from temperature sensors (not shown) located in the reactor block 106 and the reservoir 292, a processor 310 adjusts the amount of heat added to or removed from the thermal fluid 290 through the coil 308. To adjust the flow rate of thermal fluid 290 through the passageway 300, the processor 310 communicates with a valve 312 located in a reservoir outlet conduit 314. The reactor block 106, reservoir 292, pump 294, and conduits 296, 304, 314 can be insulated to improve temperature control in the reactor block 106.

Because the reactor block 106 is typically made of a metal or other material possessing high thermal conductivity, the single channel passageway 300 is usually sufficient for maintaining the temperature of the block 106 a few degrees above or below room temperature. To improve temperature uniformity within the reactor block 106, the passageway can be split into parallel channels (not shown) immediately downstream of the inlet port 298. In contrast to the single channel passageway 300 depicted in FIG. 7, each of the parallel channels passes between a single row of vessels 102 before exiting the reactor block 106. This parallel flow arrangement decreases the temperature gradient between the inlet 298 and outlet 302 ports. To further improve temperature uniformity and heat exchange between the vessels 102 and the block 106, the passageway 300 can be enlarged so that the wells 104 essentially project into a cavity containing the thermal fluid 290. Additionally, one may eliminate the reactor block 106 entirely, and suspend or immerse the vessels 102 in a bath containing the thermal fluid 290.

FIG. 8 illustrates the use of thermoelectric devices for heating and cooling individual vessels. Thermoelectric devices can function as both heaters and coolers by reversing the current flow through the device. Unlike resistive heaters, which convert electric power to heat, thermoelectric devices are heat pumps that exploit the Peltier effect to transfer heat from one face of the device to the other. A typical thermoelectric assembly has the appearance of a sandwich, in which the front face of the thermoelectric device is in thermal contact with the object to be cooled (heated), and the back face of the device is in thermal contact with a heat sink (source). When the heat sink or source is ambient air, the back face of the device typically has an array of thermally conductive fins to increase the heat transfer area Preferably, the heat sink or source is a liquid. Compared to air, liquids have higher thermal conductivity and heat capacity, and therefore should provide better heat transfer through the back face of the device. But, because thermoelectric devices are usually made with bare metal connections, they often must be physically isolated from the liquid heat sink or source.

For example, FIG. 8 illustrates one way of using thermoelectric devices 330 to heat and cool reactor vessels 338 using a liquid heat sink or source. In the configuration shown in FIG. 8, thermoelectric devices 330 are sandwiched between a reactor block 334 and a heat transfer plate 336. Reactor vessels 338 sit within wells 340 formed in the reactor block 334. Thin walls 342 at the bottom of the wells 340, separate the vessels 338 from the thermoelectric devices 330, ensuring good thermal contact. As shown in FIG. 8, each of the vessels 338 thermally contacts a single thermoelectric device 330, although in general, a thermoelectric device can heat or cool more than one of the vessels 338. The thermoelectric devices 330 either obtain heat from, or dump heat into, a thermal fluid that circulates through an interior cavity 344 of the heat transfer plate 336. The thermal fluid enters and leaves the heat transfer plate 336 through inlet 346 and outlet 348 ports, and its temperature is controlled in a manner similar to that shown in FIG. 7. During an experiment, the temperature of the thermal fluid is typically held constant, while the temperature of the vessels 338 is controlled by adjusting the electrical current, and hence, the heat transport through the thermoelectric devices 330. Though not shown in FIG. 8, the temperature of the vessels 338 are controlled in a manner similar to the scheme depicted in FIG. 6. Temperature sensors located adjacent to the vessels 338 and within the heat transfer plate cavity 344 communicate with a processor via a temperature monitor. In response to temperature data from the temperature monitor, the processor increases or decrease heat flow to or from the thermoelectric devices 330. A thermoelectric device control system, located in the communication path between the thermoelectric devices 330 and the processor, adjusts the magnitude and direction of the flow of electrical current through each of the thermoelectric devices 330 in response to signals from the processor.

Calorimetric Data Measurement and Use

Temperature measurements often provide a qualitative picture of reaction kinetics and conversion and therefore can be used to screen library members. For example, rates of change of temperature with respect to time, as well as peak temperatures reached within each of the vessels can be used to rank catalysts. Typically, the best catalysts of an exothermic reaction are those that, when combined with a set of reactants, result in the greatest heat production in the shortest amount of time.

In addition to its use as a screening tool, temperature measurement-combined with proper thermal management and design of the reactor system-can also be used to obtain quantitative calorimetric data. From such data, scientists can, for example, compute instantaneous conversion and reaction rate, locate phase transitions (melting point, glass transition temperature) of reaction products, or measure latent heats to deduce structural information of polymeric materials, including degree of crystallinity and branching.

Figure 9:
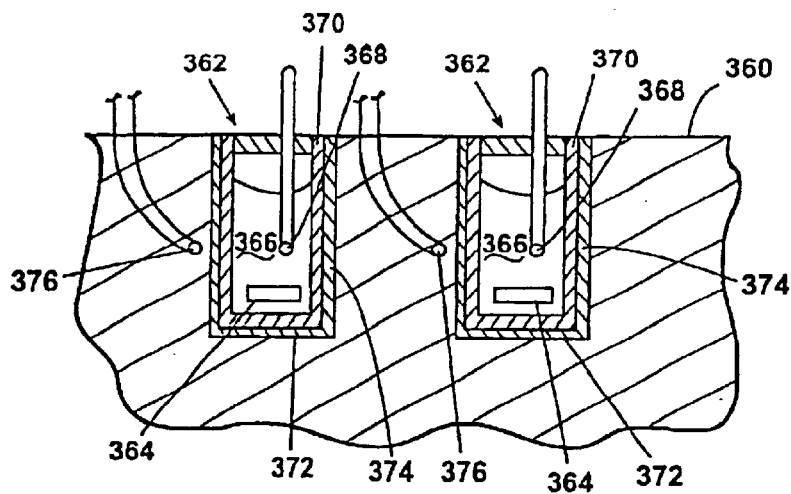
FIG. 9 is a cross-sectional view of a portion of a reactor block useful for obtaining calorimetric data.

FIG. 9 shows a cross-sectional view of a portion of a reactor block 360 that can be used to obtain accurate calorimetric data. Each of the vessels 362 contain stirring blades 364 to ensure that the contents 366 of the vessels 362 are well mixed and that the temperature within any one of the vessels 362, $T_j$, is uniform. Each of the vessels 362 contains a thermistor 368, which measures $T_j$ and heats the vessel contents 366. The walls 370 of the vessels 362 are made of glass, although one may use any material having relatively low thermal conductivity, and similar mechanical strength and chemical resistance. The vessels 362 are held within wells 372 formed in the reactor block 360, and each of the wells 372 is lined with an insulating material 374 to further decrease heat transfer to or from the vessels 362. Useful insulating materials 374 include glass wool, silicone rubber, and the like. The insulating material 374 can be eliminated or replaced by a thermal paste when better thermal contact between that reactor block 360 and the vessels 362 is desired-good thermal contact is needed, for example, when investigating exothermic reactions under isothermal conditions. The reactor block 360 is made of a material having high thermal conductivity, such as aluminum, stainless steel, brass, and so on. High thermal conductivity, accompanied by active heating or cooling using any of the methods described above, help maintain uniform temperature, $T_j$, throughout the reactor block 360. One can account for non-uniform temperatures within the reactor block 360 by measuring $T_{oj}$, the temperature of the block 360 in the vicinity of each of the vessels 362, using block temperature sensors 376. In such cases, $T_{oj}$, instead of $T_o$, is used in the calorimetric calculations described next.

An energy balance around the contents 366 of one of the vessels 362 (jth vessel) yields an expression for fractional conversion, $X_j$, of a key reactant at any time, t, assuming that the heat of reaction, $\Delta H_{r,j}$, and the specific heat of the vessel contents 366, $C_{P,j}$, are known and are constant over the temperature range of interest:

$$M_j c_{P,j} \frac{dT_j}{dt} = m_{o,j} \Delta H_{r,j} \frac{dX_j}{dt} + Q_{in,j} - Q_{out,j}. \qquad \text{I}$$

In expression I, MA is the mass of the contents 366 of the jth vessel; $m_{o,j}$ is the initial mass of the key reactant; $Q_{in,j}$ is the rate of heat transfer into the jth vessel by processes other than reaction, as for example, by resistance heating of the thermistor 368. $Q_{out,j}$ is the rate of heat transfer out of the jth vessel, which can be determined from the expression:

$$Q_{out,j} = U_j A_j (T_j - T_o) = U_j A_j \Delta T_j \qquad \text{II}$$

where $A_j$ is the heat transfer area—the surface area of the jth vessel—and $U_j$ is the heat transfer coefficient, which depends on the properties of the vessel 362 and its contents 366, as well as the stirring rate. $U_j$ can be determined by measuring the temperature rise, $\Delta T_j$, in response to a known heat input.

Equations I and II can be used to determine conversion from calorimetric data in at least two ways. In a first method, the temperature of the reactor block 360 is held constant, and sufficient heat is added to each of the vessels 362 through the thermistor 368 to maintain a constant value of $\Delta T_j$. Under such conditions, and after combining equations I and II, the conversion can be calculated from the expression $$X_j = \frac{1}{m_{o,j}\Delta H_{r,j}}\left(U_j A_j t_f \Delta T_j - \int_0^{t_f} Q_{in,j} dt\right),\quad \text{III}$$

where the integral can be determined by numerically integrating the power consumption of the thermistor 368 over the length of the experiment, $t_j$. This method can be used to measure the heat output of a reaction under isothermal conditions.

In a second method, the temperature of the reactor block 360 is again held constant, but $T_j$ increases or decreases in response to heat produced or consumed in the reaction. Equation I and II become under such circumstances $$X_j = \frac{1}{m_{o,j}\Delta H_{r,j}}\left(M_j c_{P,j}(T_{f,j} - T_{i,j}) + U_j A_j \int_0^{t_f} \Delta T_j dt\right).\quad \text{IV}$$

In equation IV, the integral can be determined numerically, and $T_{f,j}$ and $T_{i,j}$ are temperatures of the reaction mixture within the jth vessel at the beginning and end of reaction, respectively.

Thus, if $T_{f,j}$ equals $T_{i,j}$, the total heat liberated is proportional to $$\int_0^{t_f} \Delta T_j dt.$$

This method is simpler to implement than the isothermal method since it does not require temperature control of individual vessels. But, it can be used only when the temperature change in each of the reaction vessels 362 due to reaction does not significantly influence the reaction under study.

One may also calculate the instantaneous rate of disappearance of the key reactant in the jth vessel, $-r_j$, using equation I, III or IV since $-r_j$ is related to conversion through the relationship $$-r_j = C_{o,j}\frac{dX_j}{dt},\quad \text{V}$$

which is valid for constant volume reactions. The constant $C_{o,j}$ is the initial concentration of the key reactant.

Stirring Systems

Mixing variables such as stirring blade torque, rotation rate, and geometry, may influence the course of a reaction and therefore affect the properties of the reaction products. For example, the overall heat transfer coefficient and the rate of viscous dissipation within the reaction mixture may depend on the stirring blade rate of rotation. Thus, in many instances it is important that one monitor and control the rate of stirring of each reaction mixture to ensure uniform mixing. Alternatively, the applied torque may be monitored in order to measure the viscosity of the reaction mixture. As described in the next section, measurements of solution viscosity can be used to calculate the average molecular weight of polymeric reaction products.

Figure 10:
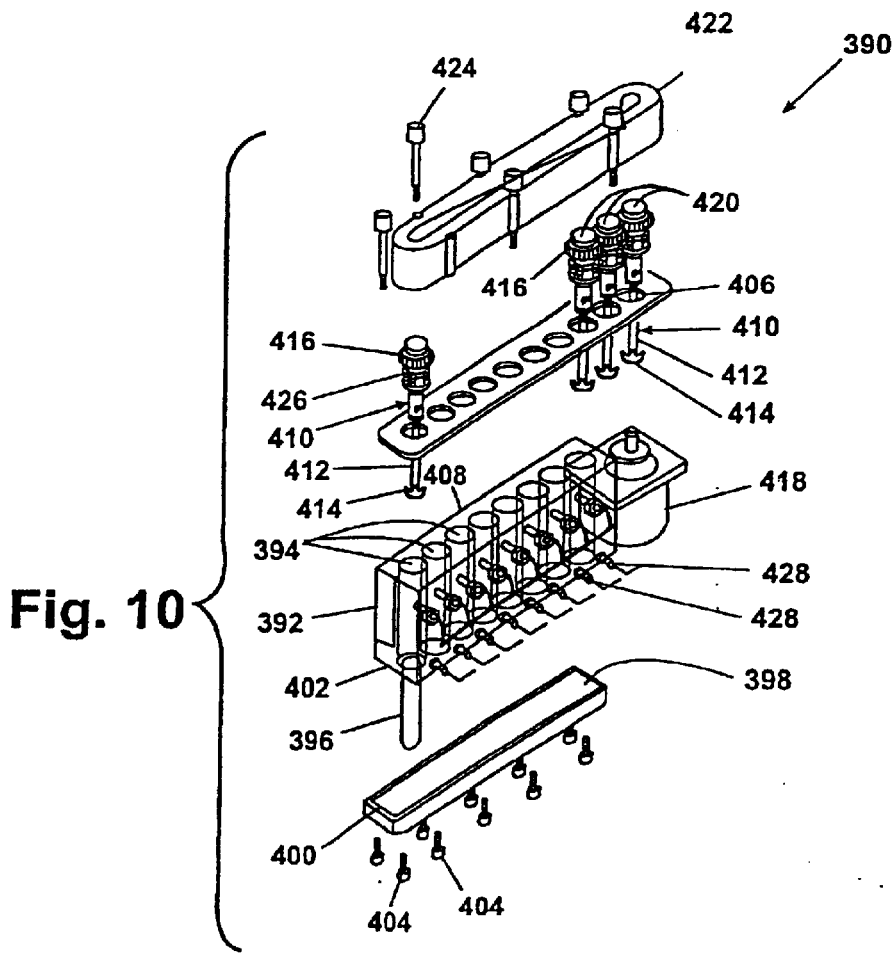
FIG. 10 is an exploded perspective view of a stirring system for a single module of a modular reactor block of the type shown in FIG. 2.

FIG. 10 shows an exploded, perspective view of a stirring system for a single module 390 of a modular reactor block of the type shown in FIG. 2. The module 390 comprises a block 392 having eight wells 394 for containing removable reaction vessels 396. The number of wells 394 and reaction vessels 396 can vary. The top surface 398 of a removable lower plate 400 serves as the base for each of the wells 394 and permits removal of the reaction vessels 396 through the bottom 402 of the block 392. Screws 404 secure the lower plate 400 to the bottom 402 of the block 392. An upper plate 406, which rests on the top 408 of the block 392, supports and directs elongated stirrers 410 into the interior of the vessels 396. Each of the stirrers 410 comprises a spindle 412 and a rotatable stirring member or stirring blade 414 which is attached to the lower end of each spindle 412. A gear 416 is attached to the upper end of each of each spindle 412. When assembled, each gear 416 meshes with an adjacent gear 416 forming a gear train (not shown) so that each stirrer 410 rotates at the same speed. A DC stepper motor 418 provides torque for rotating the stirrers 410, although an air-driven motor, a constant-speed AC motor, or a variable-speed AC motor can be used instead.

A pair of driver gears 420 couple the motor 418 to the gear train. A removable cover 422 provides access to the gear train, which is secured to the block 392 using threaded fasteners 424. In addition to the gear train, one may employ belts, chains and sprockets, or other drive mechanisms. In alternate embodiments, each of the stirrers 410 are coupled to separate motors so that the speed or torque of each of the stirrers 410 can be independently varied and monitored. Furthermore, the drive mechanism—whether employing a single motor and gear train or individual motors—can be mounted below the vessels 362. In such cases, magnetic stirring blades placed in the vessels 362 are coupled to the drive mechanism using permanent magnets attached to gear train spindles or motor shafts.

In addition to the stirring system, other elements shown in FIG. 10 merit discussion. For example, the upper plate 406 may contain vessel seals 426 that allow processing at pressures different than atmospheric pressure. Moreover, the seals 426 permit one to monitor pressure in the vessels 396 over time. As discussed below, such information can be used to calculate conversion of a gaseous reactant to a condensed species. Note that each spindle 412 may penetrate the seals 426, or may be magnetically coupled to an upper spindle member (not shown) attached to the gear 416. FIG. 10 also shows temperature sensors 428 embedded in the block 392 adjacent to each of the wells 394. The sensors 428 are part of the temperature monitoring and control system described previously.

In another embodiment, an array of electromagnets rotate freestanding stirring members or magnetic stirring bars, which obviates the need for the mechanical drive system shown in FIG. 10. Electromagnets are electrical conductors that produce a magnetic field when an electric current passes through them. Typically, the electrical conductor is a wire coil wrapped around a solid core made of material having relatively high permeability, such as soft iron or mild steel.

Figure 11:
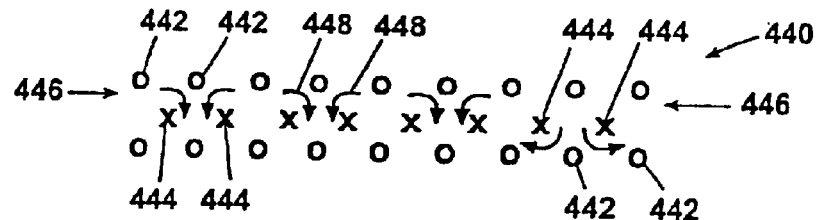
FIG. 11 is a schematic representation of an electromagnetic stirring system.

FIG. 11 is a schematic representation of one embodiment of an electromagnet stirring array 440. The electromagnets 442 or coils belonging to the array 440 are mounted in the lower plate 400 of the reactor module 390 of FIG. 10 so that their axes are about parallel to the centerlines of the vessels 396. Although greater magnetic field strength can be achieved by mounting the electromagnets with their axes perpendicular to the centerlines of the vessels 396, such a design is more difficult to implement since it requires placing electromagnets between the vessels 396. The eight crosses or vessel sites 444 in FIG. 11 mark the approximate locations of the respective centers of each of the vessels 396 of FIG. 10 and denote the approximate position of the rotation axes of the magnetic stirring bars (not shown). In the array 440 shown in FIG. 11, four electromagnets 442 surround each vessel site 444, though one may use fewer or greater numbers of electromagnets 442. The minimum number of electromagnets per vessel site is two, but in such a system it is difficult to initiate stirring, and it is common to stall the stirring bar. Electromagnet size and available packing density primarily limit the maximum number of electromagnets.

Figure 12:
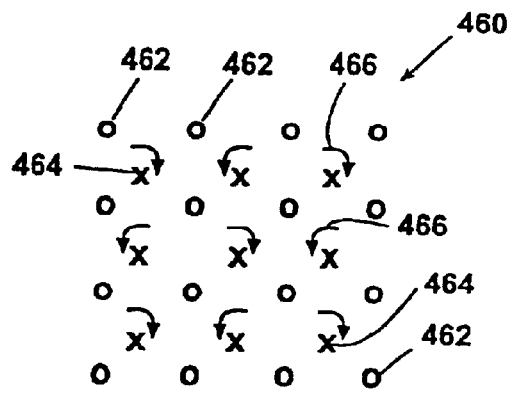
FIGS. 12–13 are schematic representations of portions of electromagnet stirring arrays in which the ratios of electromagnets to vessel sites approach 1:1 and 2:1, respectively, as the number of vessel sites becomes large.
Figure 13:
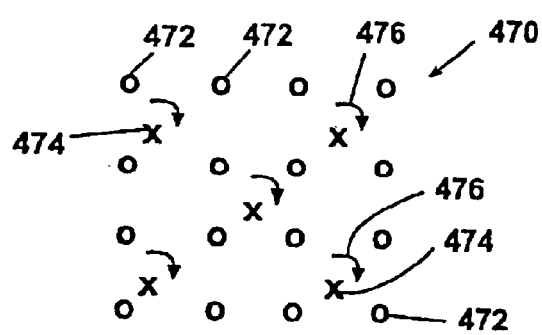
Figure 14:
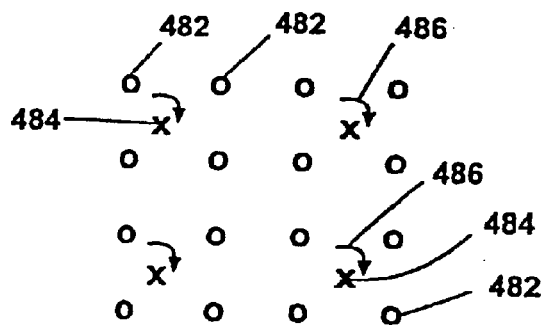
FIG. 14 is a schematic representation of an electromagnet stirring array in which the ratio of electromagnets to vessel sites is 4:1.

As illustrated in FIG. 11, each vessel site 444, except those at the ends 446 of the array 440, shares its four electromagnets 442 with two adjacent vessel sites. Because of this sharing, magnetic stirring bars at adjacent vessel sites rotate in opposite directions, as indicated by the curved arrows 448 in FIG. 11, which may lead to stalling. Other array configurations are possible. For example, FIG. 12 shows a portion of an array 460 in which the ratio of electromagnets 462 to vessel sites 464 approaches 1:1 as the number of vessel sites 464 becomes large. Because each of the vessel sites 464 shares its electromagnets 462 with its neighbors, magnetic stirring bars at adjacent vessel sites rotate in opposite directions, as shown by curved arrows 466. In contrast, FIG. 13 shows a portion of an array 470 in which the ratio of electromagnets 472 to vessel sites 474 approaches 2:1 as the number of vessel sites becomes large. Because of the comparatively large number of electromagnets 472 to vessel sites 474, all of the magnetic stirring bars can be made to rotate in the same direction 476, which minimizes stalling. Similarly, FIG. 14 shows an array 480 in which the number of electromagnets 482 to vessel sites 484 is 4:1. Each magnetic stirring bar rotates in the same direction 486.

Figure 15:
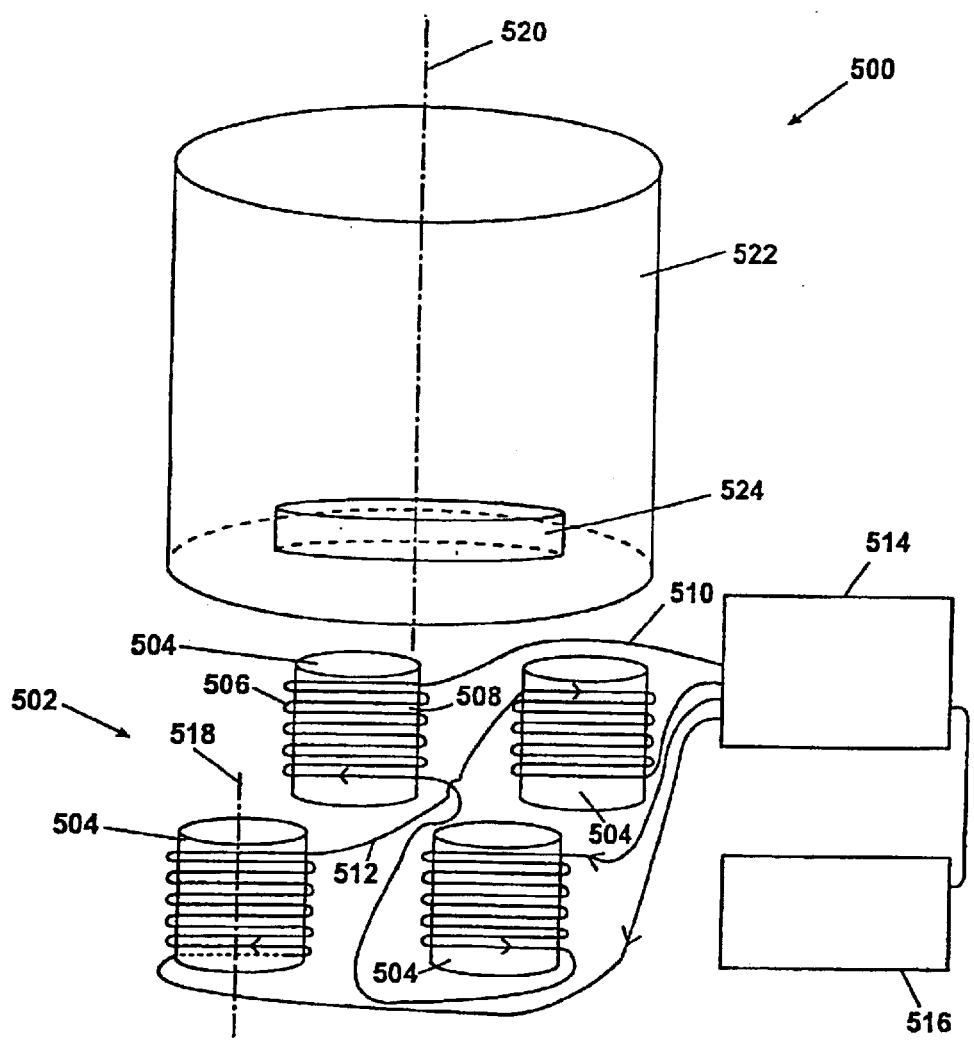
FIG. 15 shows additional elements of an electromagnetic stirring system, including drive circuit and processor.

FIG. 15 illustrates additional elements of an electromagnetic stirring system 500. For clarity, FIG. 15 shows a square electromagnet array 502 comprised of four electromagnets 504, although larger arrays, such as those shown in FIGS. 12–14, can be used. Each of the electromagnets 504 comprises a wire 506 wrapped around a high permeability solid core 508. The pairs of electromagnets 504 located on the two diagonals of the square array 502 are connected in series to form a first circuit 510 and a second circuit 512. The first 510 and second 512 circuits are connected to a drive circuit 514, which is controlled by a processor 516. Electrical current, whether pulsed or sinusoidal, can be varied independently in the two circuits 510, 512 by the drive circuit 514 and processor 516. Note that within each circuit 510, 512, the current flows in opposite directions in the wire 506 around the core 508. In this way, each of the electromagnets 504 within a particular circuit 510, 512 have opposite magnetic polarities. The axes 518 of the electromagnets 504 are about parallel to the centerline 520 of the reactor vessel 522. A magnetic stirring bar 524 rests on the bottom of the vessel 522 prior to operation. Although the electromagnets 504 can also be oriented with their axes 518 perpendicular to the vessel centerline 520, the parallel alignment provides higher packing density.

Figure 16:
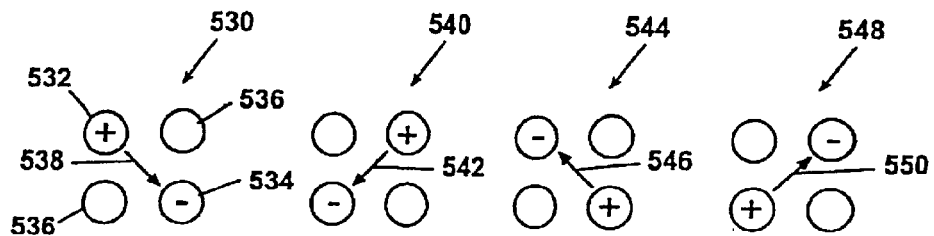
FIG. 16 illustrates the magnetic field direction of a 2×2 electromagnet array at four different times during one rotation of a magnetic stirring bar.

FIG. 16 shows the magnetic field direction of a 2×2 electromagnet array at four different times during one full rotation of the magnetic stirring bar 524 of FIG. 15, which is rotating at a steady frequency of $\omega$ radians s$^{-1}$. In FIG. 16, a circle with a plus sign 532 indicates that the electromagnet produces a magnetic field in a first direction; a circle with a minus sign 534 indicates that the electromagnet produces a magnetic field in a direction opposite to the first direction; and a circle with no sign 536 indicates that the electromagnet produces no magnetic field. At time t=0, the electromagnets 530 produce an overall magnetic field with a direction represented by a first arrow 538 at the vessel site. At time $$t = \frac{\pi}{2\omega},$$

the electromagnets 540 produce an overall magnetic field with a direction represented by a second arrow 542. Since the magnetic stirring bar 524 (FIG. 15) attempts to align itself with the direction of the overall magnetic field, it rotates clockwise ninety degrees from the first direction 538 to the second direction 542. At time $$t = \frac{\pi}{\omega},$$

the electromagnets 544 produce an overall magnetic field with a direction represented by a third arrow 546. Again, the magnetic stirring bar 524 aligns itself with the direction of the overall magnetic field, and rotates clockwise an additional ninety degrees. At time $$t = \frac{3\pi}{2\omega},$$

the electromagnets 548 produce an overall magnetic field with a direction represented by a fourth arrow 550, which rotates the magnetic stirring bar 524 clockwise another ninety degrees. Finally, at time $$t = \frac{2\pi}{\omega},$$

the electromagnets 530 produce an overall magnetic field with direction represented by the first arrow 538, which rotates the magnetic stirring bar 524 back to its position at time t=0.

Figure 17:
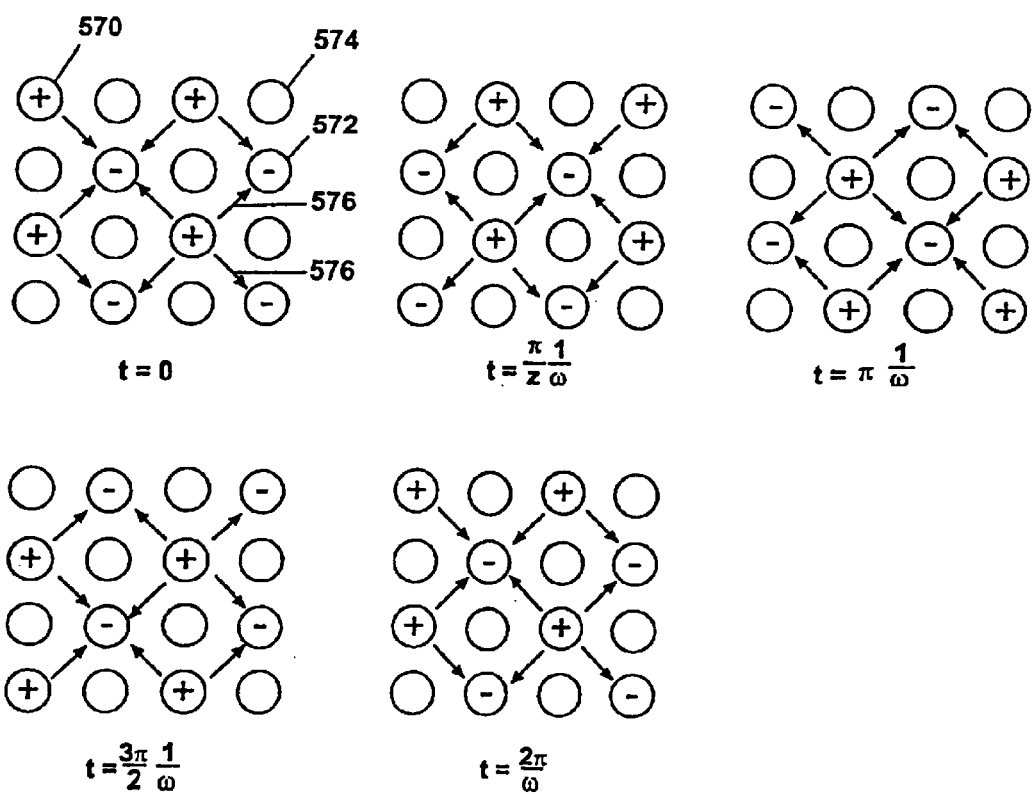
FIG. 17 illustrates the magnetic field direction of a 4×4 electromagnet array at five different times during one full rotation of a 3×3 array of magnetic stirring bars.
Figure 18:
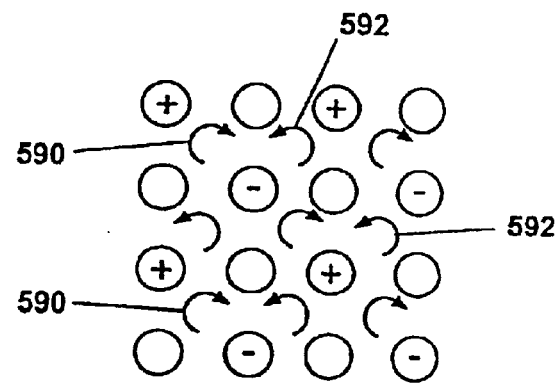
FIG. 18 illustrates the rotation direction of the 3×3 array of magnetic stirring bars shown in FIG. 17.

FIG. 17 illustrates magnetic field direction of a 4×4 electromagnetic array at five different times during one full rotation of a 3×3 array of magnetic stirring bars. As in FIG. 15, a circle with a plus sign 570, a minus sign 572, or no sign 574 represents the magnetic field direction of an individual electromagnet, while an arrow 576 represents the direction of the overall magnetic field at a vessel site. As shown, sixteen electromagnets are needed to rotate nine magnetic stirring bars. But, as indicated in FIG. 18, due to sharing of electromagnets by multiple magnetic stirring bars, the rotational direction of the magnetic fields is non-uniform. Thus, five of the fields rotate in a clockwise direction 590 while the remaining four fields rotate in a counter-clockwise direction 592.

Figure 19:
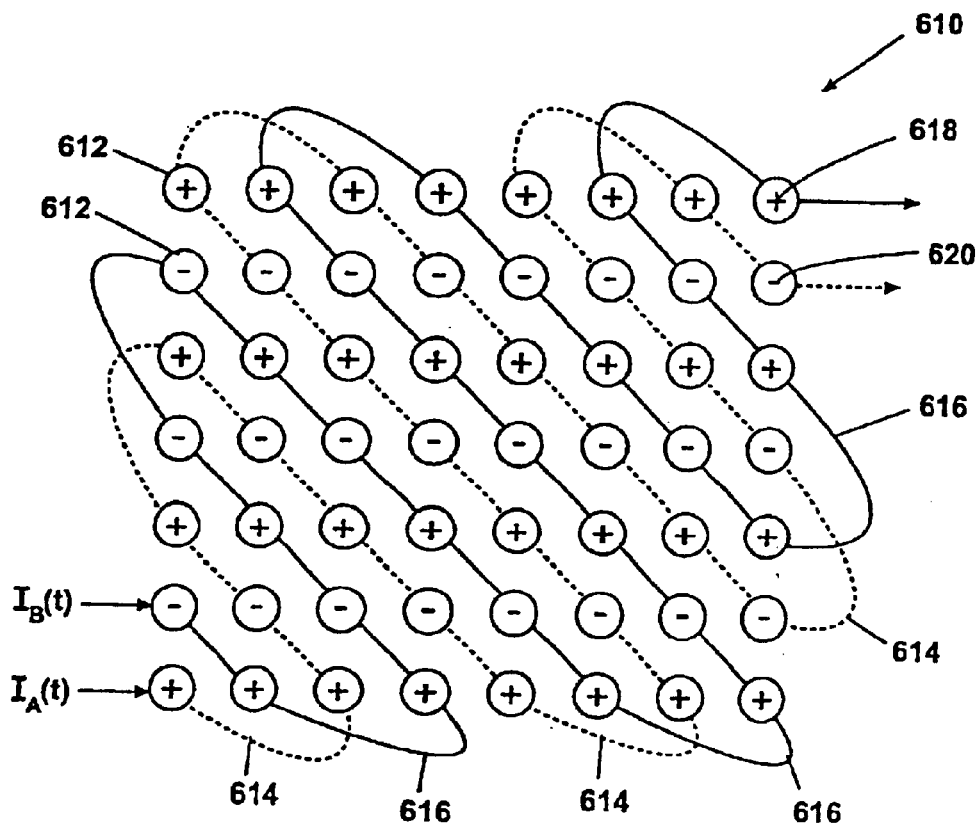
FIG. 19 shows a wiring configuration for an electromagnetic stirring system.
Figure 20:
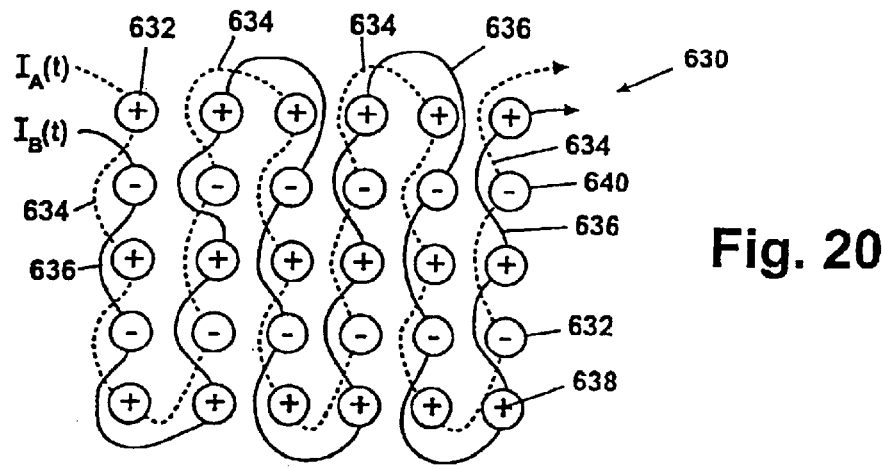
FIG. 20 shows an alternate wiring configuration for an electromagnetic stirring system.

FIG. 19 and FIG. 20 illustrate wiring configurations for electromagnet arrays in which each vessel site is located between four electromagnets defining four corners of a quadrilateral sub-array. For each vessel site, both wiring configurations result in an electrical connection between electromagnets located on the diagonals of a given sub-array. In the wiring configuration 610 shown in FIG. 19, electromagnets 612 in alternating diagonal rows are wired together to form two series of electromagnets 612. Dashed and solid lines represent electrical connections between electromagnets 612 in a first series 614 and a second series 616, respectively. Plus signs 618 and minus signs 620 indicate polarity (magnetic field direction) of individual electromagnets 612 at any time, t, when current in the first series 614 and the second series 616 of electromagnets 612 are in phase. FIG. 20 illustrates an alternate wiring configuration 630 of electromagnets 632, where again, dashed and solid lines represent electrical connections between the first 634 and second series 636 of electromagnets 632, and plus signs 638 and minus signs 640 indicate magnetic polarity.

Note that for both wiring configurations 610, 630, the polarities of the electromagnets 612, 632 of the first series 614, 634 are not the same, though amplitudes of the current passing through the connections between the electromagnets 612, 632 of the first series 614, 634 are equivalent. The same is true for the second series 616, 636 of electromagnets 612, 632. One can achieve opposite polarities within the first series 614, 634 or second series 616, 636 of electromagnets 612, 632 by reversing the direction of electrical current around the core of the electromagnet 612, 632. See, for example, FIG. 15. In the two wiring configurations 610, 630 of FIGS. 19 and 20, every quadrilateral array of four adjacent electromagnets 612, 632 defines a site for rotating a magnetic stirring bar, and the diagonal members of each of the four adjacent electromagnets 612, 632 belong to the first series 614, 634 and the second 616, 636 series of electromagnets 612, 632. Moreover, within any set of four adjacent electromagnets 612, 632, each pair of electromagnets 612, 632 belonging to the same series have opposite polarities. The two wiring configurations 610, 630 of FIGS. 19 and 20 can be used with any of the arrays 460, 470, 480 shown in FIGS. 12–14.

The complex wiring configurations 610, 630 of FIGS. 19 and 20 can be placed on a printed circuit board, which serves as both a mechanical support and alignment fixture for the electromagnets 612, 632. The use of a printed circuit board allows for rapid interconnection of the electromagnets 612, 632, greatly reducing assembly time and cost, and eliminating wiring errors associated with manual soldering of hundreds of individual connections. Switches can be used to turn stirring on and off for individual rows of vessels. A separate drive circuit may be used for each row of vessels, which allows stirring speed to be used as a variable during an experiment.

Figure 21:
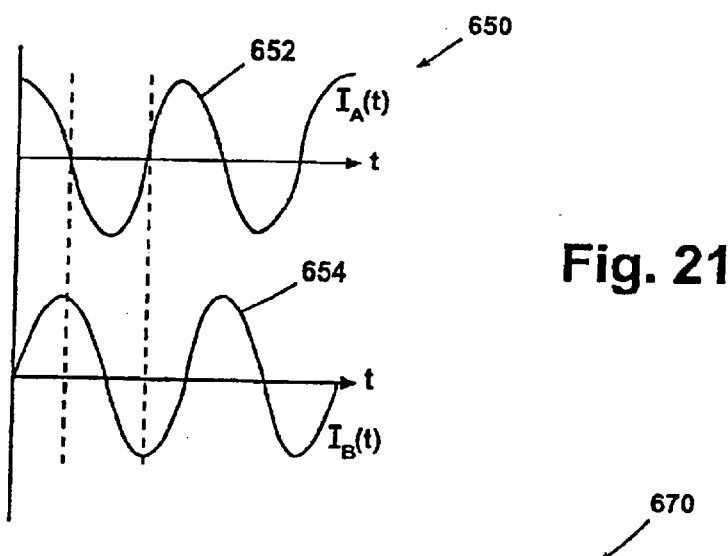
FIG. 21 shows the phase relationship between sinusoidal source currents, $I_A(t)$ and $I_B(t)$, which drive two series of electromagnets shown in FIGS. 19 and 20.

FIG. 21 is a plot 650 of current versus time and shows the phase relationship between sinusoidal source currents, $I_A(t)$ 652 and $I_B(t)$ 654, which drive, respectively, the first series 614, 634 and the second series 616, 636 of electromagnets 612, 632 shown in FIGS. 19 and 20. The two source currents 652, 654 have equivalent peak amplitude and frequency, $\omega_v$, though $I_A(t)$ 652 lags $I_B(t)$ 654 by $$\frac{\pi}{2}$$

radians. Because of this phase relationship, magnetic stirring bars placed at rotation sites defined by any four adjacent electromagnets 612, 632 of FIGS. 19 and 20 will each rotate at an angular frequency of $\omega_v$, though adjacent stirring bars will rotate in opposite directions when the electromagnet array 460 depicted in FIG. 12 is used. If, however, the arrays 470, 480 shown in FIGS. 13 and 14 are used, adjacent stirring bars will rotate in the same direction. In an alternate embodiment, a digital approximation to a sine wave can be used.

Figure 22:
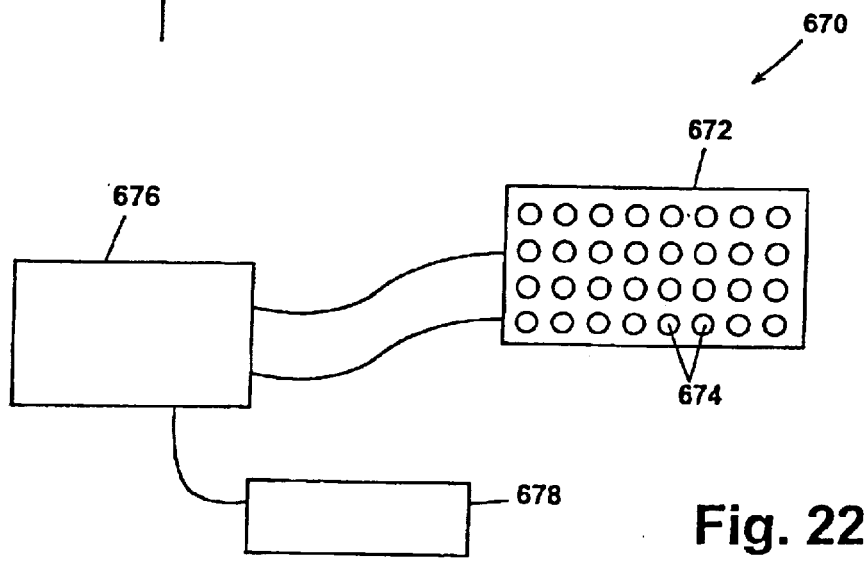
FIG. 22 is a block diagram of a power supply for an electromagnetic stirring system.

FIG. 22 is a block diagram of a power supply 670 for an electromagnet array 672. Individual electromagnets 674 are wired together in a first and second series as, for example, shown in FIG. 19 or 20. The first and second series of electromagnets 674 are connected to a power source 676, which provides the two series with sinusoidal driving currents that are $$\frac{\pi}{2}$$

radians out of phase. Normally, the amplitudes of the two driving currents are the same and do not depend on frequency. A processor 678 controls both the amplitude and the frequency of the driving currents.

Viscosity and Related Measurements

The present invention provides for in situ measurement of viscosity and related properties. As discussed below, such data can be used, for example, to monitor reactant conversion, and to rank or characterize materials based on molecular weight or particle size.

The viscosity of a polymer solution depends on the molecular weight of the polymer and its concentration in solution. For polymer concentrations well below the "semi-dilute limit"—the concentration at which the solvated polymers begin to overlap one another—the solution viscosity, $\eta$, is related to the polymer concentration, C, in the limit as C approaches zero by the expression $$\eta = (1 + C[\eta])\eta_s \qquad \text{VI}$$

where $\eta_s$ is the viscosity of the solvent. Essentially, adding polymer to a solvent increases the solvent's viscosity by an amount proportional to the polymer concentration. The proportionality constant $[\eta]$, is known as the intrinsic viscosity, and is related to the polymer molecular weight, M, through the expression $$[\eta] = [\eta_0]M^\alpha, \qquad \text{VII}$$

where $[\eta_0]$ and $\alpha$ are empirical constants. Equation VII is known as the Mark-Houwink-Sakurda (MHS) relation, and it, along with equation VI, can be used to determine molecular weight from viscosity measurements.

Equation VI requires concentration data from another source; with polymerization reactions, polymer concentration is directly related to monomer conversion. In the present invention, such data can be obtained by measuring heat evolved during reaction (see equation III and IV) or, as described below, by measuring the amount of a gaseous reactant consumed during reaction. The constants in the MHS relation are functions of temperature, polymer composition, polymer conformation, and the quality of the polymer-solvent interaction. The empirical constants, $[\eta_0]$ and $\alpha$, have been measured for a variety of polymer-solvent pairs, and are tabulated in the literature.

Although equations VI and VII can be used to approximate molecular weight, in situ measurements of viscosity in the present invention are used mainly to rank reaction products as a function of molecular weight. Under most circumstances, the amount of solvent necessary to satisfy the concentration requirement of equation VI would slow the rate of reaction to an unacceptable level. Therefore, most polymerizations are carried out at polymer concentrations above the semidilute limit, where the use of equations VI and VII to calculate molecular weight would lead to large error. Nevertheless, viscosity can be used to rank reaction products even at concentrations above the semidilute limit since a rise in viscosity during reaction generally reflects an increase in polymer concentration, molecular weight or both. If necessary, one can accurately determine molecular weight from viscosity measurements at relatively high polymer concentration by first preparing temperature-dependent calibration curves that relate viscosity to molecular weight. But the curves would have to be obtained for every polymer-solvent pair produced, which weighs against their use for screening new polymeric materials.

In addition to ranking reactions, viscosity measurements can also be used to screen or characterize dilute suspensions of insoluble particles—polymer emulsions or porous supports for heterogeneous catalysts—in which viscosity increases with particle size at a fixed number concentration. In the case of polymer emulsions, viscosity can serve as a measure of emulsion quality. For example, solution viscosity that is constant over long periods of time may indicate superior emulsion stability, or viscosity within a particular range may correlate with a desired emulsion particle size. With porous supports, viscosity measurements can be used to identify active catalysts: in many cases, the catalyst support will swell during reaction due to the formation of insoluble products within the porous support.

In accordance with the present invention, viscosity or related properties of the reactant mixtures are monitored by measuring the effect of viscous forces on stirring blade rotation. Viscosity is a measure of a fluid's resistance to a shear force. This shear force is equal to the applied torque, Γ, needed to maintain a constant angular velocity of the stirring blade. The relationship between the viscosity of the reaction mixture and the applied torque can be expressed as $$\Gamma = K_\omega(\omega_s, T)\eta, \qquad \text{VIII}$$

where $K_\omega$ is a proportionality constant that depends on the angular frequency, ω, of the stirring bar, the temperature of the reaction mixture, and the geometries of the reaction vessel and the stirring blade. $K_\omega$ can be obtained through calibration with solutions of known viscosity.

During a polymerization, the viscosity of the reaction mixture increases over time due to the increase in molecular weight of the reaction product or polymer concentration or both. This change in viscosity can be monitored by measuring the applied torque and using equation VIII to convert the measured data to viscosity. In many instances, actual values for the viscosity are unnecessary, and one can dispense with the conversion step. For example, in situ measurements of applied torque can be used to rank reaction products based on molecular weight or conversion, as long as stirring rate, temperature, vessel geometry and stirring blade geometry are about the same for each reaction mixture.

Figure 23:
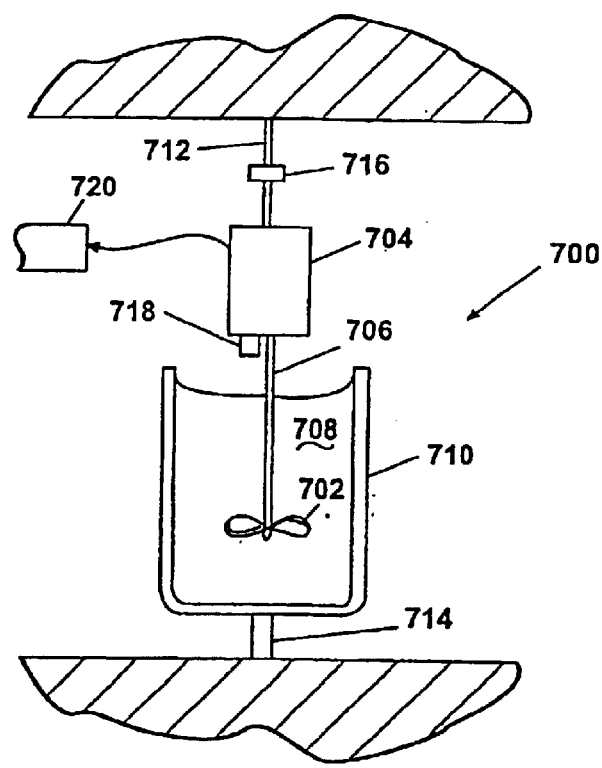
FIG. 23 illustrates an apparatus for directly measuring the applied torque of a stirring system.

FIG. 23 illustrates an apparatus 700 for directly measuring the applied torque. The apparatus 700 comprises a stirring blade 702 coupled to a drive motor 704 via a rigid drive spindle 706. The stirring blade 702 is immersed in a reaction mixture 708 contained within a reactor vessel 710. Upper 712 and lower 714 supports prevent the drive motor 704 and vessel 710 from rotating during operation of the stirring blade 702. For simplicity, the lower support 714 can be a permanent magnet. A torque or strain gauge 716 shown mounted between the upper support 712 and the drive motor 704 measures the average torque exerted by the motor 704 on the stirring blade 702. In alternate embodiments, the strain gauge 716 is inserted within the drive spindle 706 or is placed between the vessel 710 and the lower support 714. If located within the drive spindle 706, a system of brushes or commutators (not shown) are provided to allow communication with the rotating strain gauge. Often, placement of the strain gauge 716 between the vessel 710 and the lower support 714 is the best option since many stirring systems, such as the one shown in FIG. 10, use a single motor to drive multiple stirring blades.

Figure 24:
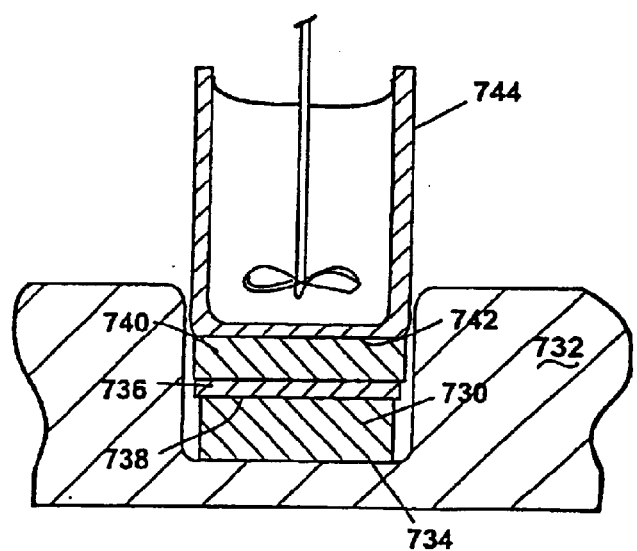
FIG. 24 shows placement of a strain gauge in a portion of a base plate that is similar to the lower plate of the reactor module shown in FIG. 10.

FIG. 24 shows placement of a strain gauge 730 in a portion of a base plate 732 that is similar to the lower plate 400 of the reactor module 390 shown in FIG. 10. The lower end 734 of the strain gauge 730 is rigidly attached to the base plate 732. A first permanent magnet 736 is mounted on the top end 738 of the strain gauge 730, and a second permanent magnet 740 is attached to the bottom 742 of a reactor vessel 744. When the vessel 744 is inserted in the base plate 732, the magnetic coupling between the first magnet 736 and the second magnet 740 prevents the vessel 744 from rotating and transmits torque to the strain gauge 730.

Besides using a strain gauge, one can also monitor drive motor power consumption, which is related to the applied torque. Referring again to FIG. 23, the method requires monitoring and control of the stirring blade 702 rotational speed, which can be accomplished by mounting a sensor 718 adjacent to the drive spindle 706. Suitable sensors 718 include optical detectors, which register the passage of a spot on the drive spindle 706 by a reflectance measurement, or which note the interruption of a light bean by an obstruction mounted on the drive spindle 706, or which discern the passage of a light beam through a slot on the drive spindle 706 or on a co-rotating obstruction. Other suitable sensors 718 include magnetic field detectors that sense the rotation of a permanent magnet affixed to the spindle 706. Operational details of magnetic field sensors are described below in the discussion of phase lag detection. Sensors such as encoders, resolvers, Hall effect sensors, and the like, are commonly integrated into the motor 704. An external processor 720 adjusts the power supplied to the drive motor 704 to maintain a constant spindle 706 rotational speed. By calibrating the required power against a series of liquids of known viscosity, the viscosity of an unknown reaction mixture can be determined.

In addition to direct measurement, torque can be determined indirectly by measuring the phase angle or phase lag between the stirring blade and the driving force or torque. Indirect measurement requires that the coupling between the driving torque and the stirring blade is "soft," so that significant and measurable phase lag occurs.

With magnetic stirring, "soft" coupling occurs automatically. The torque on the stirring bar is related to the magnetic moment of the stirring bar, μ, and the amplitude of the magnetic field that drives the rotation of the stirring bar, H, through the expression $$\Gamma = \mu H \sin\theta, \qquad \text{IX}$$

where θ is the angle between the axis of the stirring bar (magnetic moment) and the direction of the magnetic field. At a given angular frequency, and for known μ and H, the phase angle, θ, will automatically adjust itself to the value necessary to provide the amount of torque needed at that frequency. If the torque required to stir at frequency ω is proportional to the solution viscosity and the stirring frequency—an approximation useful for discussion—then the viscosity can be calculated from measurements of the phase angle using the equation $$\Gamma = \mu H \sin\theta = \alpha\eta\omega \qquad \text{X}$$

where α is a proportionality constant that depends on temperature, and the geometry of the vessel and the stirring blade. In practice, one may use equation VIII or a similar empirical expression for the right hand side of equation X if the torque does not depend linearly on the viscosity-frequency product.

Figure 25:
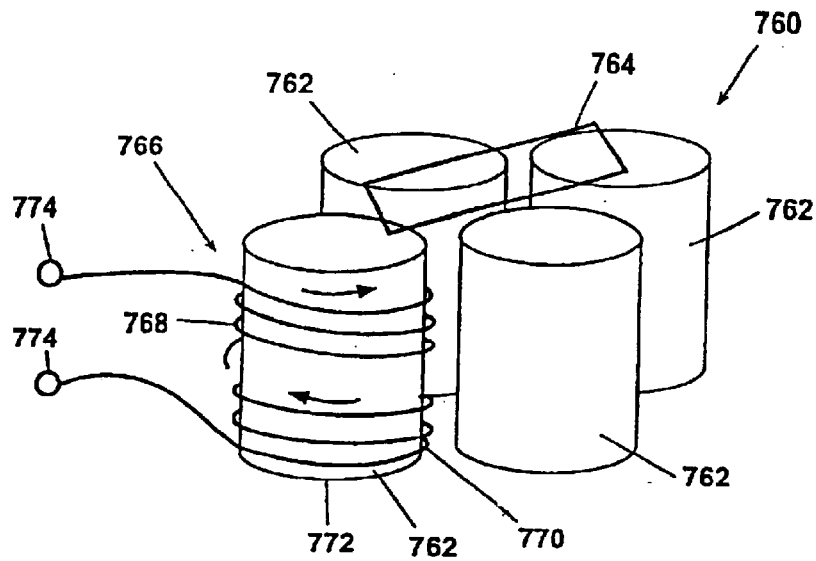
FIG. 25 shows an inductive sensing coil system for detecting rotation and measuring phase angle of a magnetic stirring blade or bar.

FIG. 25 shows an inductive sensing coil system 760 for measuring phase angle or phase lag, θ. The system 760 comprises four electromagnets 762, which drive the magnetic stirring bar 764, and a phase-sensitive detector, such as a standard lock-in amplifier (not shown). A gradient coil 766 configuration is used to sense motion of the stirring bar 764, though many other well known inductive sensing coil configurations can be used. The gradient coil 766 is comprised of a first sensing coil 768 and a second sensing coil 770 that are connected in series and are wrapped in opposite directions around a first electromagnet 772. Because of their opposite polarities, any difference in voltages induced in the two sensing coils 768, 770 will appear as a voltage difference across the terminals 774, which is detected by the lock-in amplifier. If no stirring bar 764 is present, then the alternating magnetic field of the first electromagnet 772 will induce approximately equal voltages in each of the two coils 768, 770—assuming they are mounted symmetrically with respect to the first electromagnet 772—and the net voltage across the terminals 774 will be about zero. When a magnetic stirring bar 764 is present, the motion of the rotating magnet 764 will induce a voltage in each of the two sensing coils 768, 770. But, the voltage induced in the first coil 768, which is closer to the stirring bar 764, will be much larger than the voltage induced in the second coil 770, so that the voltage across the terminals 774 will be nonzero. A periodic signal will thus be induced in the sensing coils 768, 770, which is measured by the lock-in amplifier.

Figure 26:
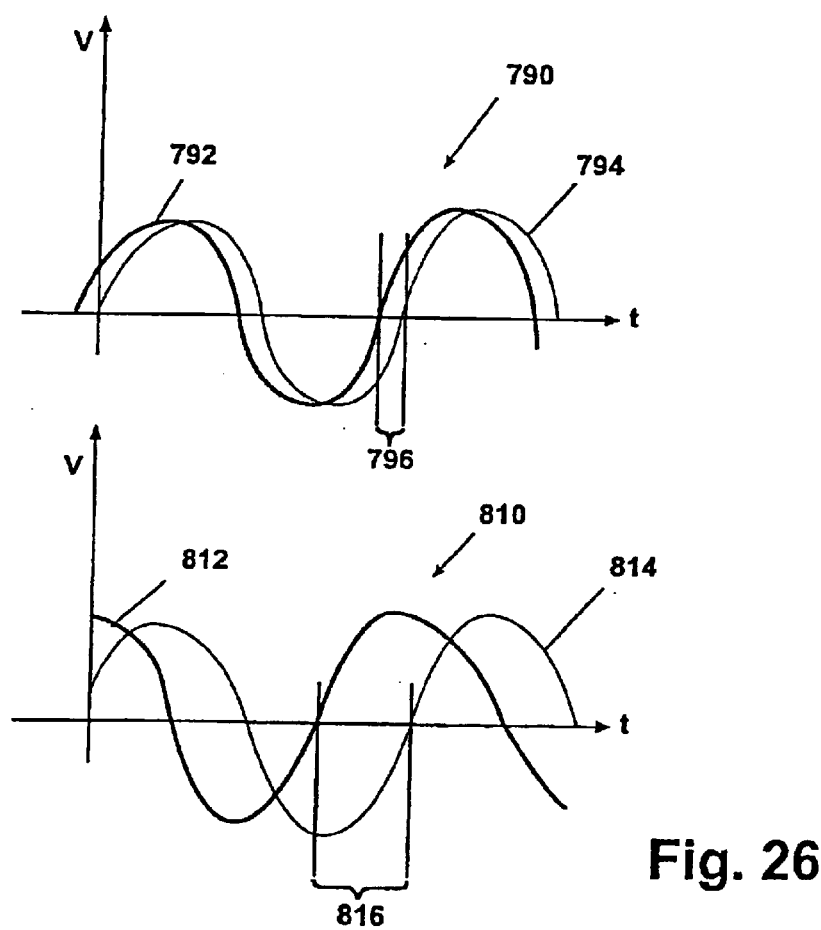
FIG. 26 shows typical outputs from inductive sensing coils, which illustrate phase lag associated with magnetic stirring for low and high viscosity solutions, respectively.
Figure 27:
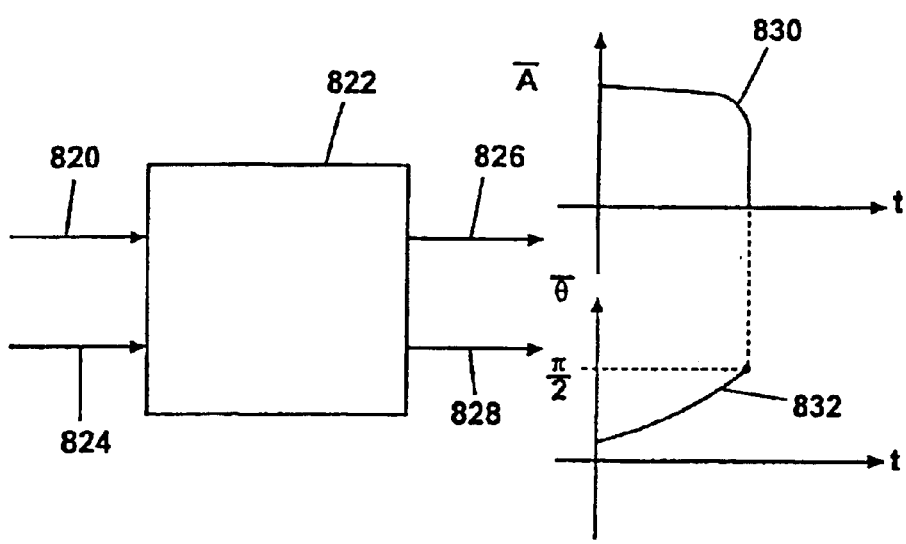
FIG. 27 illustrates how amplitude and phase angle will vary during a reaction as the viscosity increases from a low value to a value sufficient to stall the stirring bar.

FIG. 26 and FIG. 27 show typical outputs 790, 810 from the inductive sensing coil system 760 of FIG. 25, which illustrate phase lag associated with magnetic stirring for low and high viscosity solutions, respectively. Periodic signals 792, 812 from the sensing coils 768, 770 are plotted with sinusoidal reference signals 794, 814 used to drive the electromagnets. Time delay, $\Delta t$ 796, 816, between the periodic signals 792, 812 and the reference signals 794, 814 is related to the phase angle by $\theta = \omega \cdot \Delta t$. Visually comparing the two outputs 790, 810 indicates that the phase angle associated with the high viscosity solution is larger than the phase angle associated with the low viscosity solution.

FIG. 27 illustrates how amplitude and phase angle will vary during a reaction as the viscosity increases from a low value to a value sufficient to stall the stirring bar. A waveform or signal 820 from the sensing coils is input to a lock-in amplifier 822, using the drive circuit sinusoidal current as a phase and frequency reference signal 824. The lock-in amplifier 822 outputs the amplitude 826 of the sensing coil signal 820, and phase angle 828 or phase lag relative to the reference signal 824. The maximum phase angle is $$\frac{\pi}{2}$$

radians, since, as shown by equation X, torque decreases with further increases in $\theta$ leading to slip of the stirring bar 764 of FIG. 25. Thus, as viscosity increases during reaction, the phase angle 828 or phase lag also increases until the stirring bar stalls, and the amplitude 826 abruptly drops to zero. This can be seen graphically in FIG. 27, which shows plots of $\overline{A}$ 830 and $\overline{\theta}$ 832, the amplitude of the reference signal and phase angle, respectively, averaged over many stirring bar rotations. One can optimize the sensitivity of the phase angle 828 measurement by proper choice of the magnetic field amplitude and frequency.

To minimize interference from neighboring stirring bars—ideally, each set of gradient coils should sense the motion of a single stirring bar—each vessel should be provided with electromagnets that are not shared with adjacent vessels. For example, a 4:1 magnet array shown in FIG. 14 should be used instead of the 2:1 or the 1:1 magnet arrays shown in FIGS. 13 and 12, respectively. In order to take readings from all of the vessels in an array, a multiplexer can be used to sequentially route signals from each vessel to the lock-in amplifier. Normally, an accurate measurement of the phase angle can be obtained after several tens of rotations of the stirring bars. For rotation frequencies of 10–20 Hz, this time will be on the order of a few seconds per vessel. Thus, phase angle measurements for an entire array of vessels can be typically made once every few minutes, depending on the number of vessels, the stirring bar frequency, and the desired accuracy. In order to speed up the measurement process, one may employ multiple-channel signal detection to measure the phase angle of stirring bars in more than one vessel at a time. Alternate detection methods include direct digitization of the coil output waveforms using a high-speed multiplexer and/or an analog-to-digital converter, followed by analysis of stored waveforms to determine amplitude and phase angle.

Phase angle measurements can also be made with non-magnetic, mechanical stirring drives, using the inductive coil system 760 of FIG. 25. For example, one may achieve sufficient phase lag between the stirring blade and the drive motor by joining them with a torsionally soft, flexible connector. Alternatively, the drive mechanism may use a resilient belt drive rather than a rigid gear drive to produce measurable phase lag. The stirring blade must include a permanent magnet oriented such that its magnetic moment is not parallel to the axis of rotation. For maximum sensitivity, the magnetic moment of the stirring blade should lie in the plane of rotation. Note that one advantage to using a non-magnetic stirring drive is that there is no upper limit on the phase angle.

In addition to directly or indirectly measuring torque, one may sense viscosity by increasing the driving frequency, $\omega_v$ or decreasing the magnetic field strength until, in either case, the stirring bar stalls because of insufficient torque. The point at which the stirring bar stops rotating can be detected using the same setup depicted in FIG. 25 for measuring phase angle. During a ramp up (down) of the driving frequency (field strength), the magnitude of the lock-in amplifier output will abruptly fall by a large amount when the stirring bar stalls. The frequency or field strength at which the stirring bar stalls can be correlated with viscosity: the lower the frequency or the higher the field strength at which stalling occurs, the greater the viscosity of the reaction mixture.

With appropriate calibration, the method can yield absolute viscosity data, but generally the method is used to rank reactions. For example, when screening multiple reaction mixtures, one may subject all of the vessels to a series of step changes in either frequency or field strength, while noting which stirring bars stall after each of the step changes. The order in which the stirring bars stall indicates the relative viscosity of the reaction mixtures since stirring bars immersed in mixtures having higher viscosity will stall early. Note that, in addition to providing data on torque and stall frequency, the inductive sensing coil system 760 of FIG. 25 and similar devices can be used as diagnostic tools to indicate whether a magnetic stirring bar has stopped rotating during a reaction.

Mechanical Oscillators

Piezoelectric quartz resonators or mechanical oscillators can be used to evaluate the viscosity of reaction mixtures, as well as a host of other material properties, including molecular weight, specific gravity, elasticity, dielectric constant, and conductivity. In a typical application, the mechanical oscillator, which can be as small as a few mm in length, is immersed in the reaction mixture. The response of the oscillator to an excitation signal is obtained for a range of input signal frequencies, and depends on the composition and properties of the reaction mixture. By calibrating the resonator with a set of well characterized liquid standards, the properties of the reaction mixture can be determined from the response of the mechanical oscillator. Further details on the use of piezoelectric quartz oscillators to measure material properties are described in co-pending U.S. patent application Ser. No. 09/133,171 "Method and Apparatus for Characterizing Materials by Using a Mechanical Resonator," filed Aug. 12, 1998, which is herein incorporated by reference.

Although many different kinds of mechanical oscillators currently exist, some are less useful for measuring properties of liquid solutions. For example, ultrasonic transducers or oscillators cannot be used in all liquids due to diffraction effects and steady acoustic (compressive) waves generated within the reactor vessel. These effects usually occur when the size of the oscillator and the vessel are not much greater than the characteristic wavelength of the acoustic waves. Thus, for reactor vessel diameters on the order of a few centimeters, the frequency of the mechanical oscillator should be above 1 MHz. Unfortunately, complex liquids and mixtures, including polymer solutions, often behave like elastic gels at these high frequencies, which results in inaccurate resonator response.

Often, shear-mode transducers as well as various surface-wave transducers can be used to avoid some of the problems associated with typical ultrasonic transducers. Because of the manner in which they vibrate, shear mode transducers generate viscous shear waves instead of acoustic waves. Since viscous shear waves decay exponentially with distance from the sensor surface, such sensors tend to be insensitive to the geometry of the measurement volume, thus eliminating most diffraction and reflection problems. Unfortunately, the operating frequency of these sensors is also high, which, as mentioned above, restricts their use to simple fluids. Moreover, at high vibration frequencies, most of the interaction between the sensor and the fluid is confined to a thin layer of liquid near the sensor surface. Any modification of the sensor surface through adsorption of solution components will often result in dramatic changes in the resonator response.

Figure 28:
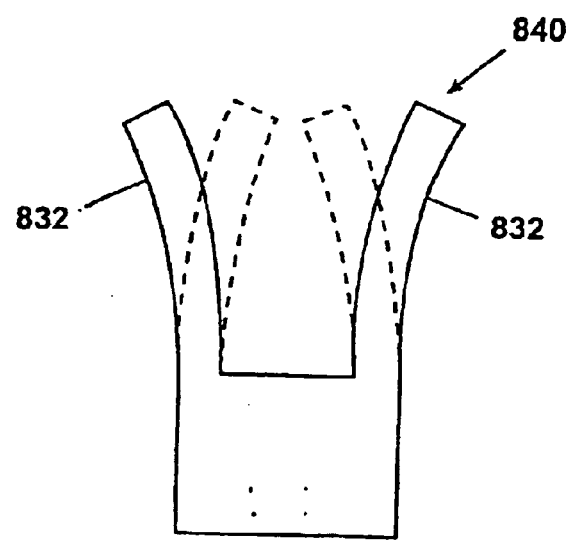
FIGS. 28–29 show bending modes of tuning forks and bimorph/unimorph resonators, respectively.
Figure 29:
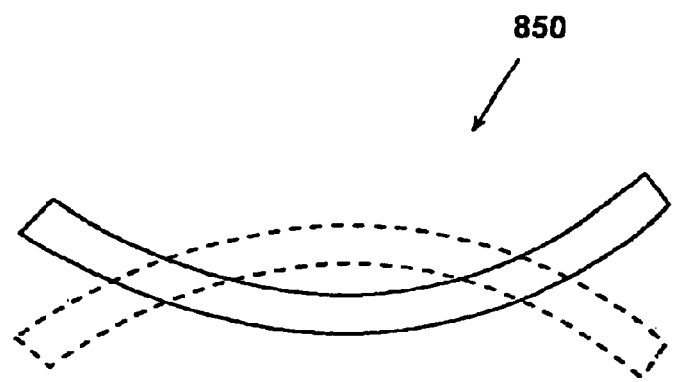

Tuning forks 840 and bimorph/unimorph resonators 850 shown in FIG. 28 and FIG. 29, respectively, overcome many of the drawbacks associated with ultrasonic transducers. Because of their small size, tuning forks 840 and bimorph/unimorph resonators 850 have difficulty exciting acoustic waves, which typically have wavelengths many times their size. Furthermore, though one might conclude otherwise based on the vibration mode shown in FIG. 28, tuning forks 840 generate virtually no acoustic waves: when excited, each of the tines 832 of the tuning fork 840 acts as a separate acoustic wave generator, but because the tines 832 oscillate in opposite directions and phases, the waves generated by each of the tines 832 cancel one another. Like the shear mode transducers described above, the bimorph/unimorph 850 resonators produce predominantly viscous waves and therefore tend to be insensitive to the geometry of the measurement volume. But unlike the shear mode transducers, bimorph/unimorph 850 resonators operate at much lower frequencies, and therefore can be used to measure properties of polymeric solutions.

Figure 30:
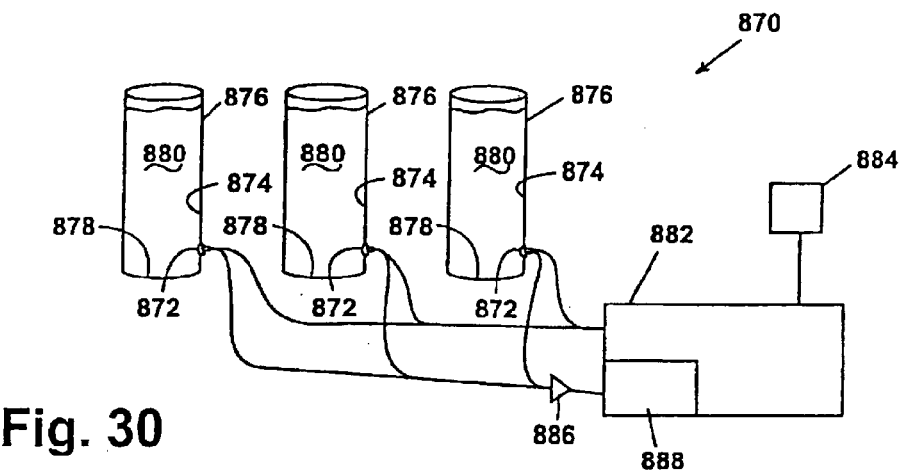
FIG. 30 schematically shows a system for measuring the properties of reaction mixtures using mechanical oscillators.

FIG. 30 schematically shows a system 870 for measuring the properties of reaction mixtures using mechanical oscillators 872. An important advantage of the system 870 is that it can be used to monitor the progress of a reaction. The oscillators 872 are mounted on the interior walls 874 of the reaction vessels 876. Alternatively, the oscillators 872 can be mounted along the bottom 878 of the vessels 876 or can be freestanding within the reaction mixtures 880. Each oscillator 872 communicates with a network analyzer 882 (for example, an HP8751A analyzer), which generates a variable frequency excitation signal. Each of the oscillators 872 also serve as receivers, transmitting their response signals back to the network analyzer 882 for processing. The network analyzer 882 records the responses of the oscillators 872 as functions of frequency, and sends the data to storage 884. The output signals of the oscillators 872 pass through a high impedance buffer amplifier 886 prior to measurement by the wide band receiver 888 of the network analyzer 882.

Other resonator designs may be used. For example, to improve the suppression of acoustic waves, a tuning fork resonator with four tines can be used. It is also possible to excite resonator oscillations through the use of voltage spikes instead of a frequency sweeping AC source. With voltage spike excitation, decaying free oscillations of the resonator are recorded instead of the frequency response. A variety of signal processing techniques well known to those of skill in the art can be used to distinguish resonator responses.

Alternate embodiments can be described with reference to the parallel reactor system 130 shown in FIG. 2. A single resonator (not shown) is attached to the 3-axis translation system 150. The translation system 150, at the direction of the processor 160, places the resonator within a reactor vessel of interest. A reading of resonator response is taken and compared to calibration curves, which relate the response to viscosity, molecular weight, specific gravity, or other properties. In another embodiment, a portion of the reaction mixture is withdrawn from a reactor vessel, using, for example, the liquid handling system 146, and is placed in a separate vessel containing a resonator. The response of the resonator is measured and compared to calibration data. Although the system 870 shown in FIG. 30 is better suited to monitor solution properties in situ, the two alternate embodiments can be used as post-characterization tools and are much simpler to implement.

In addition to mechanical oscillators, other types of sensors can be used to evaluate material properties. For example, interdigitated electrodes can be used to measure dielectric properties of the reaction mixtures.

Pressure Control System

Figure 31:
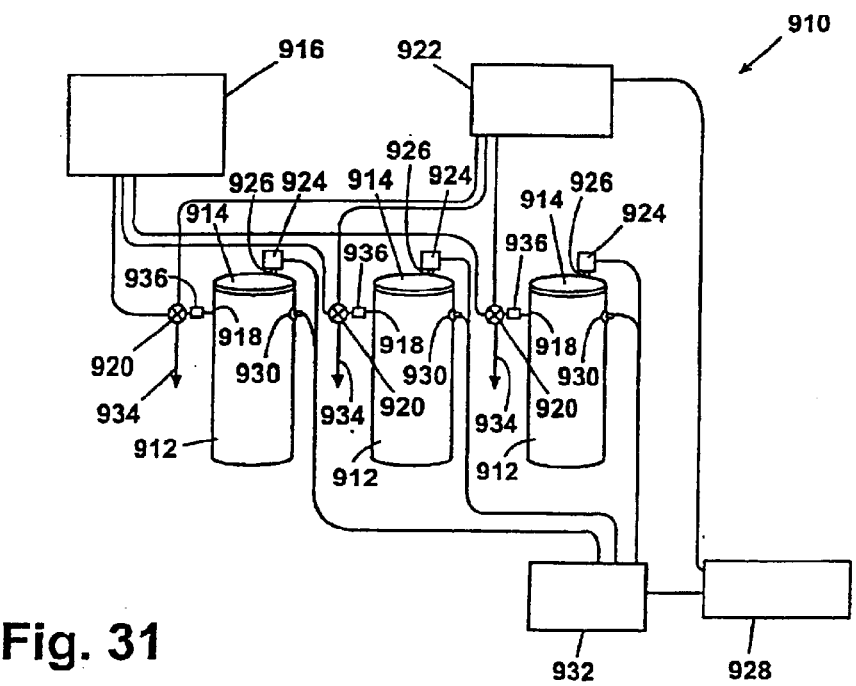
FIG. 31 shows an apparatus for assessing reaction kinetics based on monitoring pressure changes due to production or consumption various gases during reaction.

Another technique for assessing reaction kinetics is to monitor pressure changes due to production or consumption of various gases during reaction. One embodiment of this technique is shown in FIG. 31. A parallel reactor 910 comprises a group of reactor vessels 912. A gas-tight cap 914 seals each of the vessels 912 and prevents unintentional gas flow to or from the vessels 912. Prior to placement of the cap 914, each of the vessels 912 is loaded with liquid reactants, solvents, catalysts, and other condensed-phase reaction components using the liquid handling system 146 shown in FIG. 2. Gaseous reactants from source 916 are introduced into each of the vessels 912 through a gas inlet 918. Valves 920, which communicate with a controller 922, are used to fill the reaction vessels 912 with the requisite amount of gaseous reactants prior to reaction. A pressure sensor 924 communicates with the vessel head space—the volume within each of the vessels 912 that separates the cap 914 from the liquid components—through a port 926 located in the cap 914. The pressure sensors 924 are coupled to a processor 928, which manipulates and stores data. During reaction, any changes in the head space pressure, at constant temperature, reflect changes in the amount of gas present in the head space. This pressure data can be used to determine the molar production or consumption rate, $r_i$, of a gaseous component since, for an ideal gas at constant temperature, $$r_i = \frac{1}{RT}\frac{dp_i}{dt} \qquad \text{XI}$$

where R is the universal gas constant and p, is the partial pressure of the ith gaseous component. Temperature sensors 930, which communicate with the processor 928 through monitor 932, provide data that can be used to account for changes in pressure resulting from variations in head space temperature. The ideal gas law or similar equation of state can be used to calculate the pressure correction.

In an alternate embodiment, the valves 920 are used to compensate for the consumption of a gaseous reactant, in a reaction where there is a net loss in moles of gas-phase components. The valves 920 are regulated by the valve controller 922, which communicates with the processor 928. At the beginning of the reaction, the valves 920 open to allow gas from the high pressure source 916 to enter each of the vessels 912. Once the pressure within each of the vessels 912, as read by the sensor 924, reaches a predetermined value, $P_H$, the processor 928 closes the valves 920. As the reaction consumes the source 916 gas, the total pressure within each of the vessels 912 decreases. Once the pressure in a particular vessel 912 falls below a predetermined value, $P_L$, the processor 928 opens the valve 920 associated with the particular vessel 912, repressurizing it to $P_H$. This process—filling each of the vessels 912 with source 916 gas to $P_H$, allowing the head space pressure to drop below $P_L$, and then refilling the vessels 912 with source 916 gas to $P_H$—is usually repeated many times during the course of the reaction. Furthermore, the total pressure in the head space of each of the vessels 912 is continuously monitored and recorded during the gas fill-pressure decay cycle.

An analogous method can be used to investigate reactions where there is a net gain of gas-phase components. At the beginning of a reaction, all reaction materials are introduced into the vessels 912 and the valves 920 are closed. As the reaction proceeds, gas production results in a rise in head space pressure, which sensors 924 and processor 928 monitor and record. Once the pressure within a particular vessel 912 reaches $P_H$, the processor 928 directs the controller 922 to open the appropriate valve 920 to depressurize the vessel 912. The valve 920, which is a multi-port valve, vents the gas from the head space through an exhaust line 934. Once the head space pressure falls below $P_L$, the processor 928 instructs the controller 922 to close the valve 920. The total pressure is continuously monitored and recorded during the gas rise-vent cycle.

The gas consumption (production) rates can be estimated from the total pressure data by a variety of methods. For simplicity, these methods are described in terms of a single reactor vessel 912 and valve 920, but they apply equally well to a parallel reactor 910 comprising multiple vessels 912 and valves 920. One estimate of gas consumption (production) can be made from the slope of the pressure decay (growth) curves obtained when the valve is closed. These data, after converting total pressure to partial pressure based on reaction stoichiometry, can be inserted into equation XI to calculate $r_i$, the molar consumption (production) rate. A second estimate can be made by assuming that a fixed quantity of gas enters (exits) the vessel during each valve cycle. The frequency at which the reactor is repressurized (depressurized) is therefore proportional to the gas consumption (production) rate. A third, more accurate estimate can be obtained by assuming a known gas flow rate through the valve. Multiplying this value by the time during which the valve remains open yields an estimate for the quantity of gas that enters or leaves the vessel during a particular cycle. Dividing this product by the time between the next valve cycle-that is, the time it takes for the pressure in the vessel head space to fall from $P_H$ to $P_L$—yields an average value for the volumetric gas consumption (production) rate for the particular valve cycle. Summing the quantity of gas added during all of the cycles equals the total volume of gas consumed (produced) during the reaction.

The most accurate results are obtained by directly measuring the quantity of gas that flows through the valve. This can be done by noting the change in pressure that occurs during the time the valve is open—the ideal gas law can be used to convert this change to the volume of gas that enters or leaves the vessel. Dividing this quantity by the time between a particular valve cycle yields an average volumetric gas consumption (production) rate for that cycle. Summing the volume changes for each cycle yields the total volume of gas consumed (produced) in the reaction.

In an alternate embodiment shown in FIG. 31, the gas consumption rate is directly measured by inserting flow sensors 936 downstream of the valves 920 or by replacing the valves 920 with flow sensors 936. The flow sensors 936 allow continuous monitoring of the mass flow rate of gas entering each of the vessels 912 through the gas inlet 918. To ensure meaningful comparisons between experiments, the pressure of the source 916 gas should remain about constant during an experiment. Although the flow sensors 936 eliminate the need for cycling the valves 920, the minimum detectable flow rates of this embodiment are less than those employing pressure cycling. But, the use of flow sensors 936 is generally preferred for fast reactions where the reactant flow rates into the vessels 912 are greater than the threshold sensitivity of the flow sensors 936.

Illustrative Example of Calibration of Mechanical Oscillators for Measuring Molecular Weight Mechanical oscillators were used to characterize reaction mixtures comprising polystyrene and toluene. To relate resonator response to the molecular weight of polystyrene, the system 870 illustrated in FIG. 30 was calibrated using polystyrene standards of known molecular weight dissolved in toluene. Each of the standard polystyrene-toluene solutions had the same concentration, and were run in separate (identical) vessels using tuning fork piezoelectric quartz resonators similar to the one shown in FIG. 28. Frequency response curves for each resonator were recorded at intervals between about 10 and 30 seconds.

Figure 32:
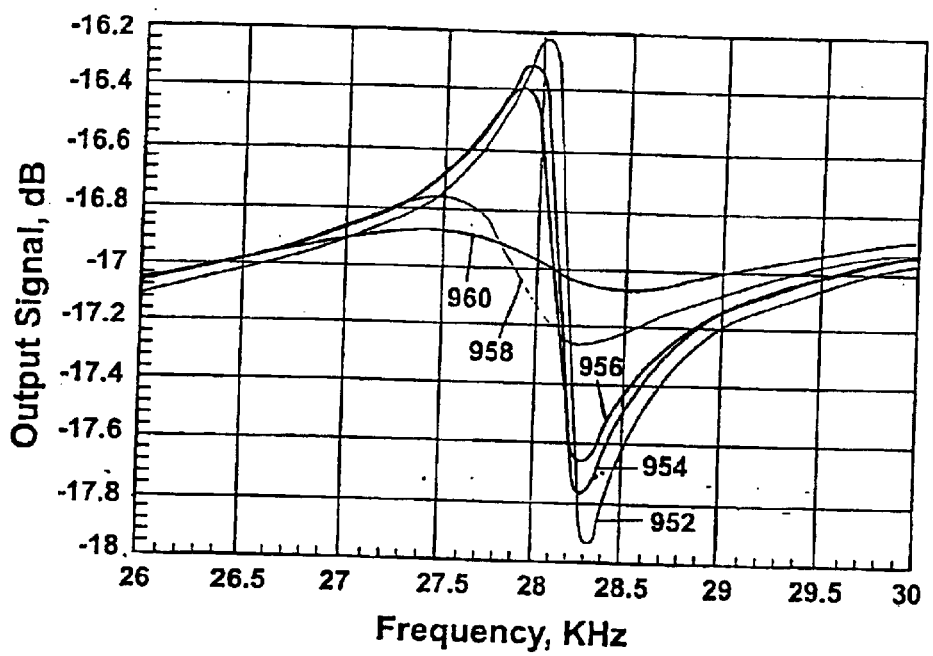
FIG. 32 shows results of calibration runs for polystyrene-toluene solutions using mechanical oscillators.

The calibration runs produced a set of resonator responses that could be used to relate the output from the oscillators 872 immersed in reaction mixtures to polystyrene molecular weight. FIG. 32 shows results of calibration runs 970 for the polystyrene-toluene solutions. The curves are plots of oscillator response for polystyrene-toluene solutions comprising no polystyrene 952, and polystyrene standards having weight average molecular weights ($M_w$) of $2.36 \times 10^3$ 954, $13.7 \times 10^3$ 956, $114.2 \times 10^3$ 958, and $1.88 \times 10^6$ 960.

Figure 33:
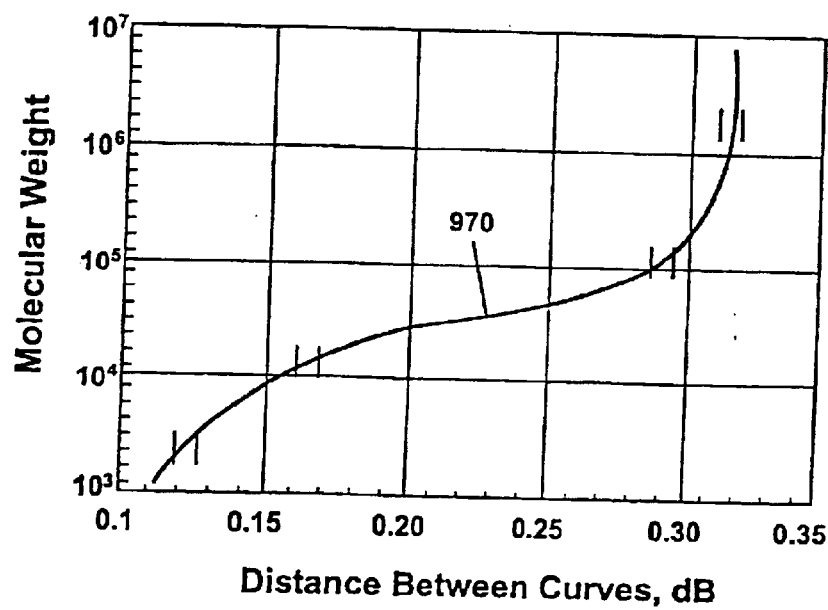
FIG. 33 shows a calibration curve obtained by correlating $M_w$ of the polystyrene standards with the distance between the frequency response curve for toluene and each of the polystyrene solutions of FIG. 32.

FIG. 33 shows a calibration curve 970 obtained by correlating $M_w$ of the polystyrene standards with the distance between the frequency response curve for toluene 952 and each of the polystyrene solutions 954, 956, 958, 960 of FIG. 32. This distance was calculated using the expression:

$$d_i = \sqrt{\frac{1}{f_1 - f_0} \int_{f_0}^{f_1} (R_0 - R_i)^2 \, df}, \quad \text{XII}$$

where $f_0$ and $f_1$ are the lower and upper frequencies of the response curve, respectively; $R_0$ is the frequency response of the resonator in toluene, and $R_1$ is the resonator response in a particular polystyrene-toluene solution. Given response curves for an unknown polystyrene-toluene mixture and pure toluene 952 (FIG. 32), the distance between the two curves can be determined from equation XII. The resulting d can be located along the calibration curve 970 of FIG. 33 to determine $M_w$ for the unknown polystyrene-toluene solution.

Figure 34:
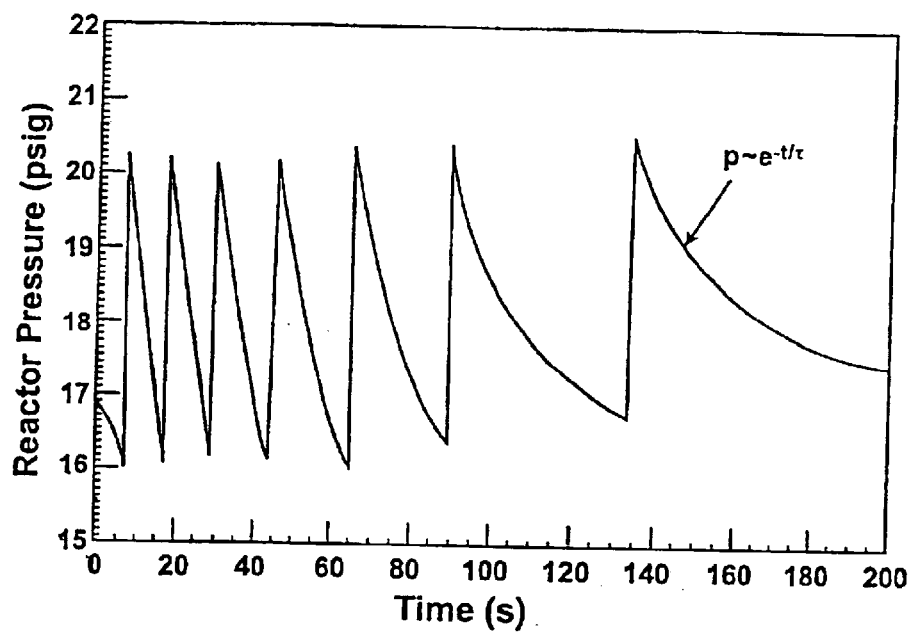
FIG. 34 depicts the pressure recorded during solution polymerization of ethylene to polyethylene.

Illustrative Example of Measurement of Gas-Phase Reactant Consumption by Pressure Monitoring and Control FIG. 34 depicts the pressure recorded during solution polymerization of ethylene to polyethylene. The reaction was carried out in an apparatus similar to that shown in FIG. 31. An ethylene gas source was used to compensate for ethylene consumed in the reaction. A valve, under control of a processor, admitted ethylene gas into the reaction vessel when the vessel head space pressure dropped below $P_L \approx 16.1$ psig due to consumption of ethylene. During the gas filling portion of the cycle, the valve remained open until the head space pressure exceeded $P_H \approx 20.3$ psig.

Figure 35:
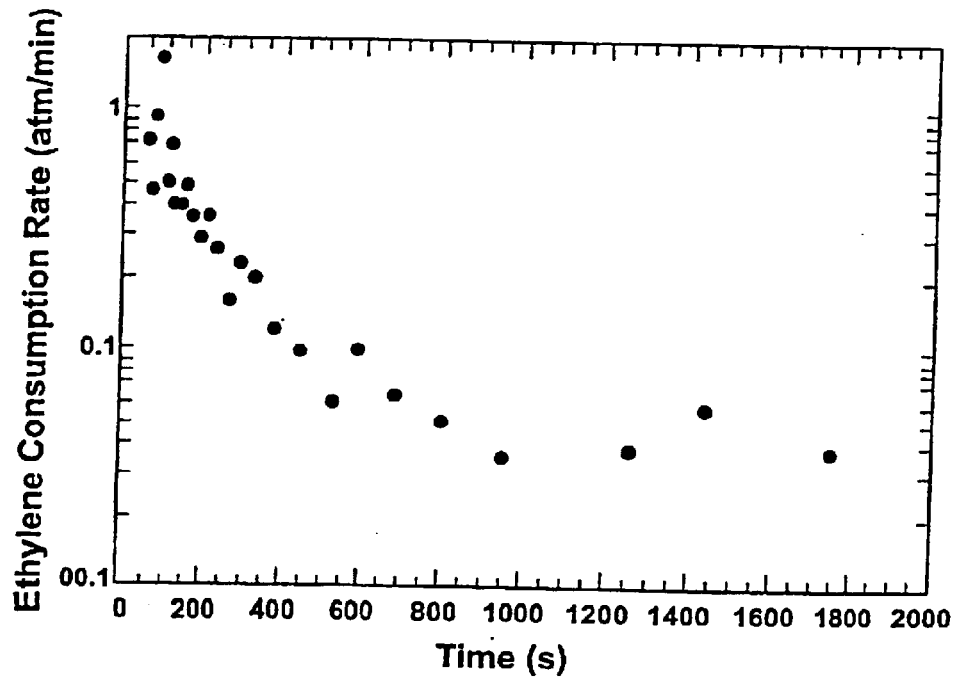
FIGS. 35–36 show ethylene consumption rate as a function of time, and the mass of polyethylene formed as a function of ethylene consumed, respectively.
Figure 36:
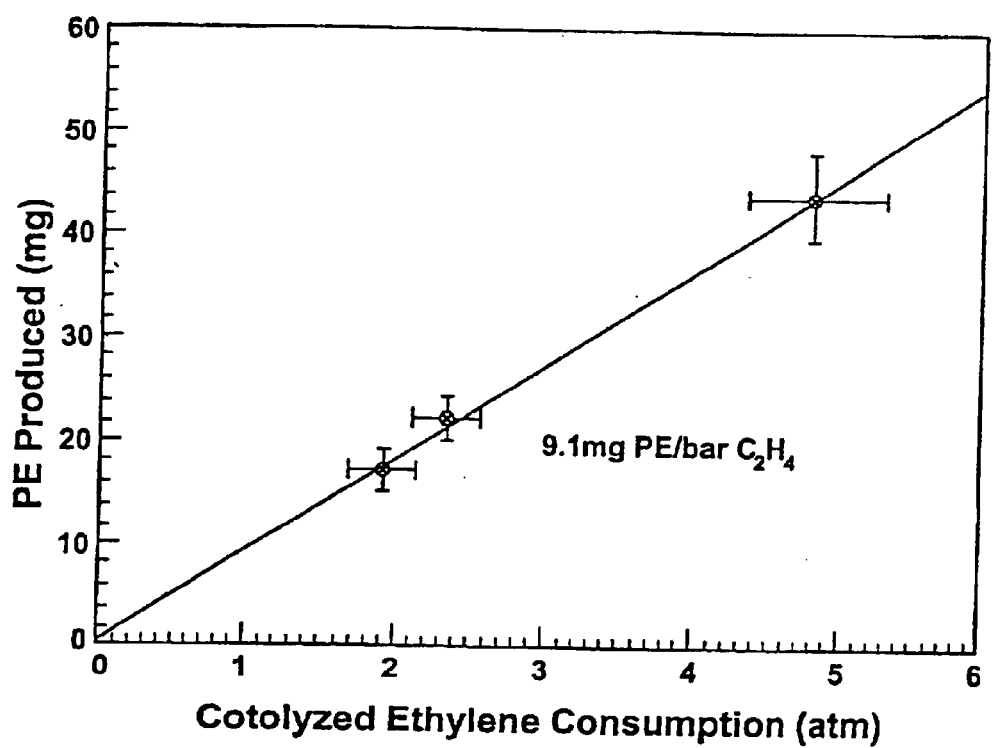

FIG. 35 and FIG. 36 show ethylene consumption rate as a function of time, and the mass of polyethylene formed as a function of ethylene consumed, respectively. The average ethylene consumption rate, $-r_{C2,k}$ (atm min$^{-1}$), was determined from the expression $$-r_{C2,k} = \frac{(P_H - P_L)_k}{\Delta t_k} \quad \text{XIII}$$

where subscript k refers to a particular valve cycle, and $\Delta t_k$ is the time interval between the valve closing during the present cycle and the valve opening at the beginning of the next cycle. As shown in FIG. 35, the constant ethylene consumption rate at later times results from catalyzed polymerization of ethylene. The high ethylene consumption rate early in the process results primarily from transport of ethylene into the catalyst solution prior to establishing an equilibrium ethylene concentration in the liquid phase. FIG. 36 shows the amount of polyethylene produced as a function of the amount of ethylene consumed by reaction. The amount of polyethylene produced was determined by weighing the reaction products, and the amount of ethylene consumed by reaction was estimated by multiplying the constant average consumption rate by the total reaction time. A linear least-squares fit to these data yields a slope which matches the value predicted from the ideal gas law and from knowledge of the reaction temperature and the total volume occupied by the gas (the product of vessel head space and number of valve cycles during the reaction).

Automated, High Pressure Injection System

Figure 37:
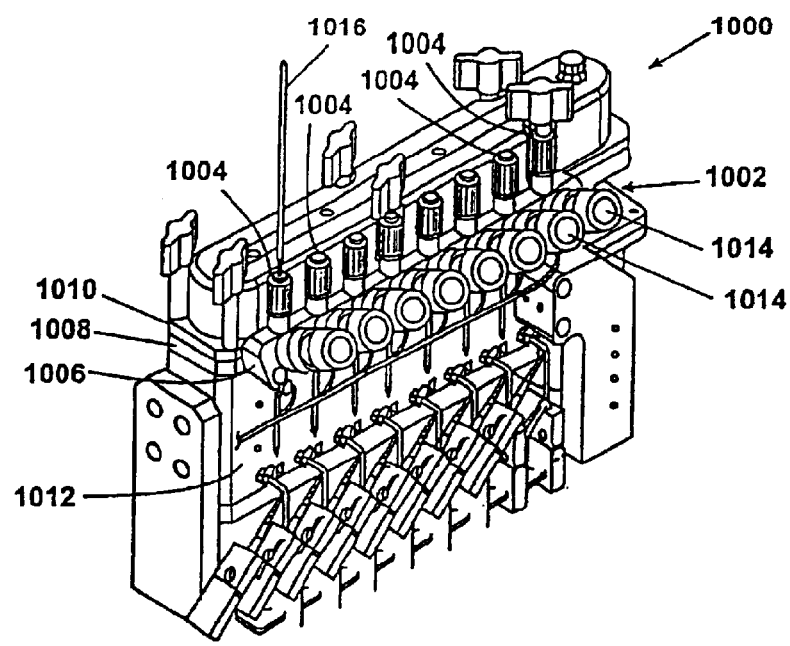
FIG. 37 shows a perspective view of an eight-vessel reactor module, of the type shown in FIG. 10, which is fitted with an optional liquid injection system.

FIG. 37 shows a perspective view of an eight-vessel reactor module 1000, of the type shown in FIG. 10, which is fitted with an optional liquid injection system 1002. The liquid injection system 1002 allows addition of liquids to pressurized vessels, which, as described below, alleviates problems associated with pre-loading vessels with catalysts. In addition, the liquid injection system 1002 improves concurrent analysis of catalysts by permitting screening reactions to be selectively quenched through the addition of a liquid-phase catalyst poison.

The liquid injection system 1002 helps solve problems concerning liquid-phase catalytic polymerization of a gaseous monomer. When using the reactor module 390 shown in FIG. 10 to screen or characterize polymerization catalysts, each vessel is normally loaded with a catalyst and a solvent prior to reaction. After sealing, gaseous monomer is introduced into each vessel at a specified pressure to initiate polymerization. As discussed in Example 1, during the early stages of reaction, the monomer concentration in the solvent increases as gaseous monomer dissolves in the solvent. Although the monomer eventually reaches an equilibrium concentration in the solvent, catalyst activity may be affected by the changing monomer concentration prior to equilibrium. Moreover, as the monomer dissolves in the solvent early in the reaction, additional gaseous monomer is added to maintain the pressure in the vessel headspace. This makes it difficult to distinguish between pressure changes in the vessels due to polymerization in the liquid phase and pressure changes due to monomer transport into the solvent to establish an equilibrium concentration. These analytical difficulties can be avoided using the liquid injection system 1002, since the catalyst can be introduced into the vessels after the monomer has attained an equilibrium concentration in the liquid phase.

The liquid injection system 1002 of FIG. 37 also helps solve problems that arise when using the reactor module 390 shown in FIG. 10 to investigate catalytic co-polymerization of gaseous and liquid co-monomers. Prior to reaction, each vessel is loaded with a catalyst and the liquid co-monomer. After sealing the vessels, gaseous co-monomer is introduced into each vessel to initiate co-polymerization. However, because appreciable time may elapse between loading of liquid components and contact with the gaseous co-monomer, the catalyst may homo-polymerize a significant fraction of the liquid co-monomer. In addition, the relative concentration of the co-monomers in the liquid-phase changes during the early stages of reaction as the gaseous co-monomer dissolves in the liquid phase. Both effects lead to analytical difficulties that can be avoided using the liquid injection system 1002, since catalysts can be introduced into the vessels after establishing an equilibrium concentration of the gaseous and liquid co-monomers in the vessels. In this way, the catalyst contacts the two co-monomers simultaneously.

The liquid injector system 1002 shown in FIG. 37 also allows users to quench reactions at different times by adding a liquid phase catalyst poison, which improves screening of materials exhibiting a broad range of catalytic activity. When using the reactor module 390 of FIG. 10 to concurrently evaluate library members for catalytic performance, the user may have little information about the relative activity of library members. If every reaction is allowed to proceed for the same amount of time, the most active catalysts may generate an excessive amount of product, which can hinder post reaction analysis and reactor clean up. Conversely, the least active catalysts may generate an amount of product insufficient for characterization. By monitoring the amount of product in each of the vessels—through the use of mechanical oscillators or phase lag measurements, for instance—the user can stop a particular reaction by injecting the catalyst poison into the vessels once a predetermined conversion is achieved. Thus, within the same reactor and in the same experiment, low and high activity catalysts may undergo reaction for relatively long and short time periods, respectively, with both sets of catalysts generating about the same amount of product.

Referring again to FIG. 37, the liquid injection system 1002 comprises fill ports 1004 attached to an injector manifold 1006. An injector adapter plate 1008, sandwiched between an upper plate 1010 and block 1012 of the reactor module 1000, provides conduits for liquid flow between the injector manifold 1006 and each of the wells or vessels (not shown) within the block 1012. Chemically inert valves 1014 attached to the injector manifold 1006 and located along flow paths connecting the fill ports 104 and the conduits within the adapter plate 1008, are used to establish or prevent fluid communication between the fill ports 1004 and the vessels or wells. Normally, the liquid injection system 1002 is accessed through the fill ports 1004 using a probe 1016, which is part of an automated liquid delivery system such as the robotic material handling system 146 shown in FIG. 2. However, liquids can be manually injected into the vessels through the fill ports 1004 using a pipette, syringe, or similar liquid delivery device. Conventional high-pressure liquid chromatography loop injectors can be used as fill ports 1004. Other useful fill ports 1004 are shown in FIG. 38 and FIG. 39.

Figure 38:
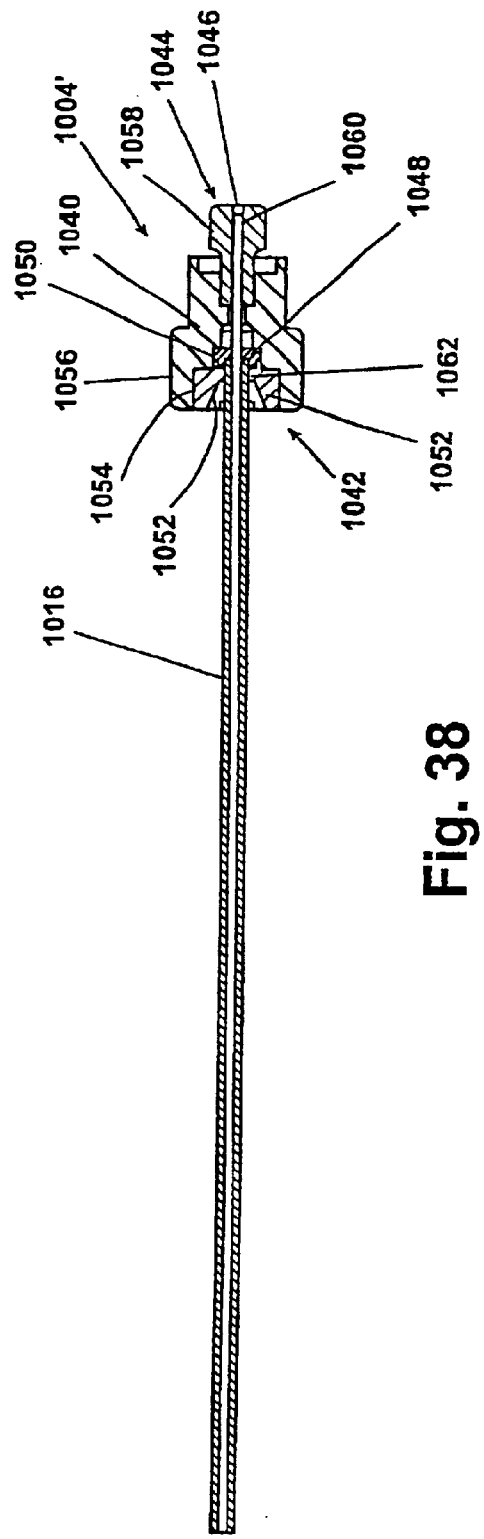
FIG. 38 shows a cross sectional view of a first embodiment of a fill port having an o-ring seal to minimize liquid leaks.

FIG. 38 shows a cross sectional view of a first embodiment of a fill port 1004' having an o-ring seal to minimize liquid leaks. The fill port 1004' comprises a generally cylindrical fill port body 1040 having a first end 1042 and a second end 1044. An axial bore 1046 runs the length of the fill port body 1040. An elastomeric o-ring 1048 is seated within the axial bore 1046 at a point where there is an abrupt narrowing 1050, and is held in place with a sleeve 1052 that is threaded into the first end 1042 of the fill port body 1040. The sleeve 1052 has a center hole 1054 that is sized to accommodate the widest part of the probe 1016. The sleeve 1052 is typically made from a chemically resistant plastic, such as polyethylethylketone (PEEK), polytetrafluoroethylene (PTFE), and the like, which minimizes damage to the probe 1016 and fill port 1004' during liquid injection. To aid in installation and removal, the fill port 1004' has a knurled first outer surface 1056 located adjacent to the first end 1042 of the fill port 1004', and a threaded second outer surface 1058, located adjacent to the second end 1044 of the fill port 1004'.

FIG. 38 also shows the position of the probe 1016 during liquid injection. Like a conventional pipette, the probe 1016 is a cylindrical tube having an outer diameter (OD) at the point of liquid delivery that is smaller than the OD over the majority of the probe 1016 length. As a result, near the probe tip 1060, there is a transition zone 1062 where the probe 1016 OD narrows. Because the inner diameter (ID) of the o-ring 1048 is about the same as the OD of the probe tip 1060, a liquid-tight seal is formed along the probe transition zone 1060 during liquid injection.

Figure 39:
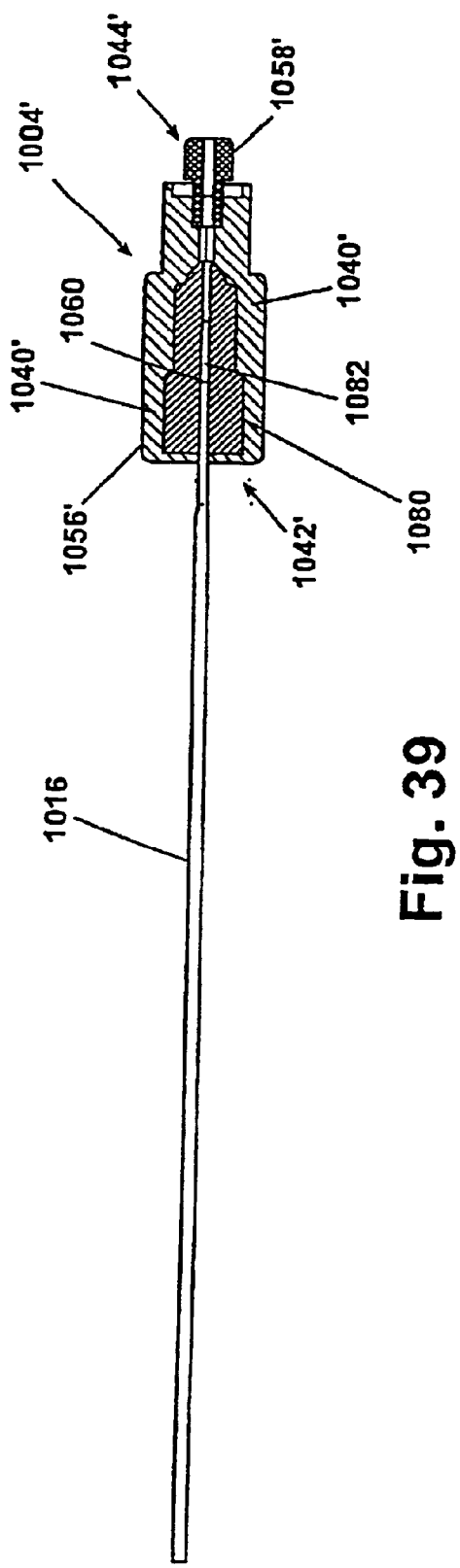
FIG. 39 shows a second embodiment of a fill port.

FIG. 39 shows a second embodiment of a fill port 1004". Like the first embodiment 1004' shown in FIG. 38, the second embodiment 1004" comprises a generally cylindrical fill port body 1040' having a first end 1042' and a second end 1044'. But instead of an o-ring, the fill port 1004" shown in FIG. 39 employs an insert 1080 having a tapered axial hole 1082 that results an interference fit, and hence a seal, between the probe tip 1060 and the ID of the tapered axial hole 1082 during liquid injection. The insert 1080 can be threaded into the first end 1042' of the fill port 1004". Typically, the insert 1080 is made from a chemically resistant plastic, such as PEEK, PTFE, and the like, which minimizes damage to the probe 1016 and fill port 1004" during liquid injection. To aid in removal and installation, the fill port' has a knurled first outer surface 1056' located adjacent to the first end 1042' of the fill port 1004", and a threaded second outer surface 1058' located adjacent to the second end 1044' of the fill port 1004".

Figure 40:
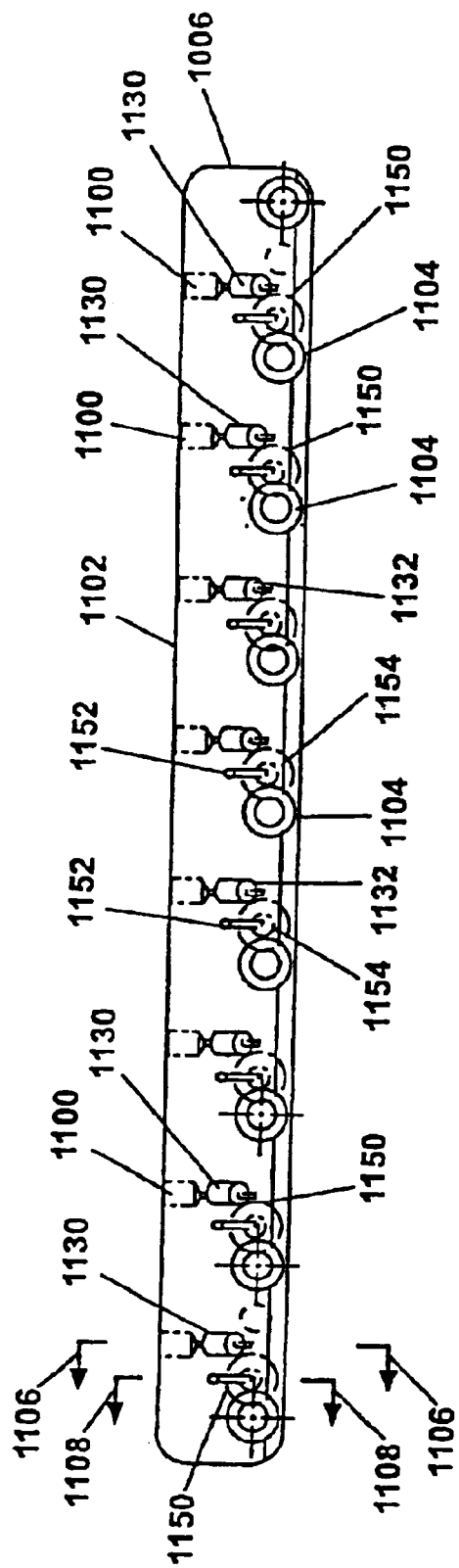
FIG. 40 shows a phantom front view of an injector manifold.

FIG. 40 shows a phantom front view of the injector manifold 1006. The injector manifold 1006 includes a series of fill port seats 1100 located along a top surface 1102 of the injector manifold 1006. The fill port seats 1100 are dimensioned to receive the second ends 1044, 1044' of the fill ports 1004', 1004" shown in FIG. 38 and FIG. 39. Locating holes 1104, which extend through the injector manifold 1006, locate the valves 1014 of FIG. 37 along the front of the injector manifold 1006.

Figure 40A:
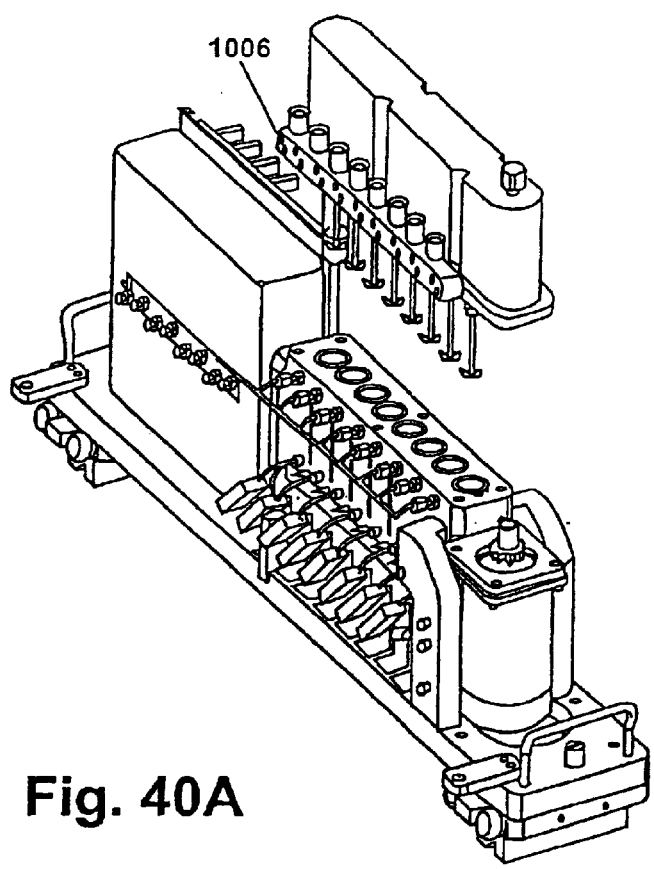
FIG. 40A shows a perspective view of an injector manifold 1006.
Figure 40B:
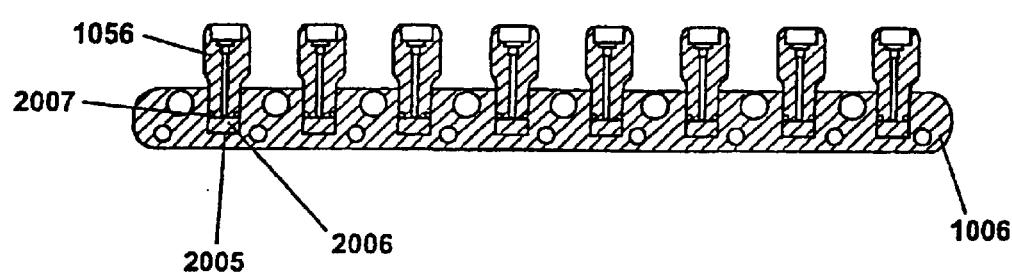
FIG. 40B shows a cross sectional view of the injector manifold shown in FIG. 40A.

An alternative design for the valve 1014, which is used with the injection ports is shown is FIG. 40A and FIG. 40B. FIG. 40A shows the injector manifold 1006, which is shown in a cross sectional view in FIG. 40B. The alternative valve design is essentially a check valve that has a spring 2005 under a poppet 2006. When not injecting, the spring 2005 assisted by the pressure of the reaction vessel pushes the poppet 2006 against a seal 2007 to seal the reaction vessel. The seal may be of a type known to those of skill in the art, such as an o-ring seal. When injecting, a pump associated with the probe 1016 forces the material to be injected against the poppet 2006 overcoming the pressure in the chamber and the spring 2005 force to allow the material being injected to flow past the poppet into the reaction vessel via the channel in the module.

Figure 41:
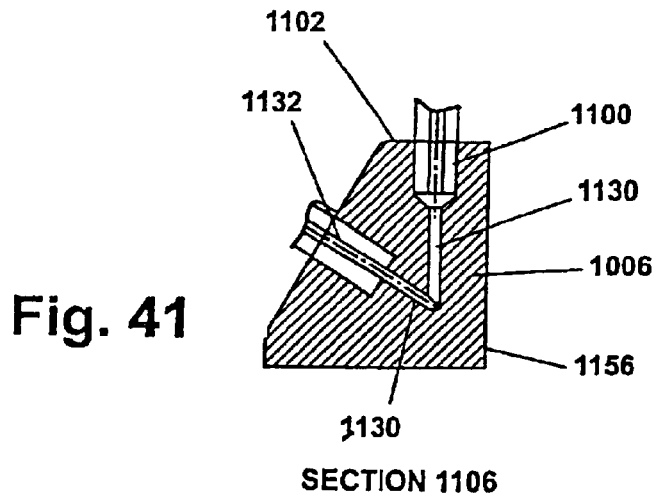
FIGS. 41–42 show a cross sectional view of an injector manifold along first and second section lines shown in FIG. 40, respectively.

FIG. 41 shows a cross sectional view of the injector manifold 1006 along a first section line 1106 of FIG. 40. The cross section illustrates one of a group of first flow paths 1130. The first flow paths 1130 extend from the fill port seats 1100, through the injector manifold 1006, to valve inlet seats 1132. Each of the valve inlet seats 1132 is dimensioned to receive an inlet port (not shown) of one of the valves 1014 depicted in FIG. 37. The first flow paths 1130 thus provide fluid communication between the fill ports 1004 and the valves 1014 of FIG. 37.

Figure 42:
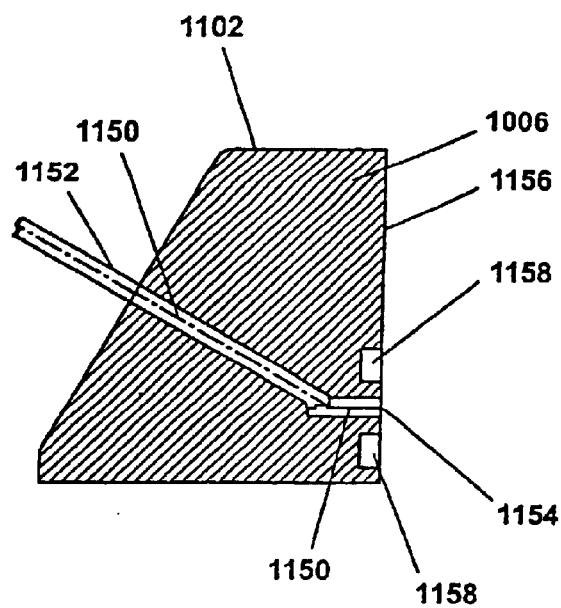

FIG. 42 shows a cross sectional view of the injector manifold 1006 along a second section line 1108 of FIG. 40. The cross section illustrates one of a group of second flow paths 1150. The second flow paths 1150 extend from valve outlet seats 1152, through the injector manifold 1006, to manifold outlets 1154 located along a back surface 1156 of the injector manifold 1006. Each of the valve outlet seats 1152 is dimensioned to receive an outlet port (not shown) of one of the valves 1014 depicted in FIG. 37. The manifold outlets 1154 mate with fluid conduits on the injector adapter plate 1008. Annular grooves 1158, which surround the manifold outlets 1154, are sized to receive o-rings (not shown) that seal the fluid connection between the manifold outlets 1154 and the fluid conduits on the injector adapter plate 1008. The second flow paths 1150 thus provide fluid communication between the valves 1014 and the injector adapter plate 1008.

Figure 43:
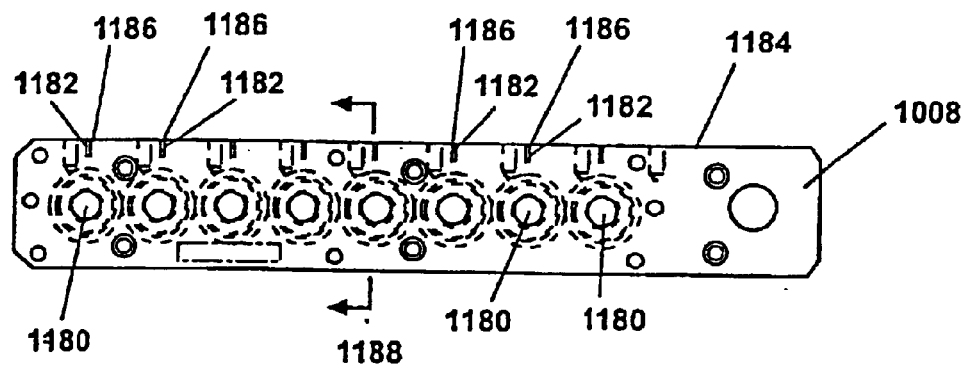
FIG. 43 shows a phantom top view of an injector adapter plate, which serves as an interface between an injector manifold and a block of a reactor module shown in FIG. 37.

FIG. 43 shows a phantom top view of the injector adapter plate 1008, which serves as an interface between the injector manifold 1006 and the block 1012 of the reactor module 1000 shown in FIG. 37. The injector adapter plate 1008 comprises holes 1180 that provide access to the vessels and wells within the block 1012. The injector adapter plate 1008 also comprises conduits 1182 extending from a front edge 1184 to the bottom surface of the adapter plate 1008. When the adapter plate 1008 is assembled in the reactor module 1000, inlets 1186 of the conduits 1182 make fluid connection with the manifold outlets 1154 shown in FIG. 42.

Figure 44:
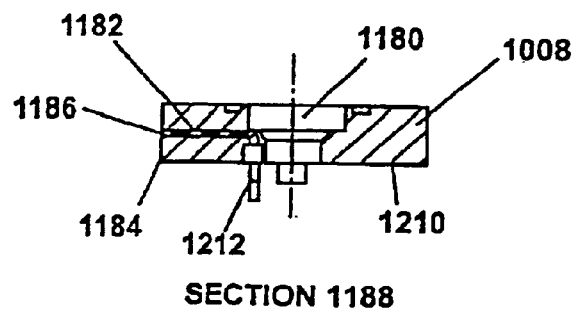
FIG. 44 shows a cross sectional side view of an injector adapter plate along a section line shown in FIG. 43.

As shown in FIG. 44, which is a cross sectional side view of the injector adapter plate 1008 along a section line 1188 of FIG. 43, the conduits 1182 terminate on a bottom surface

1210 of the injector plate 1008 at conduit outlets 1212. The bottom surface 1210 of the adapter plate 1008 forms an upper surface of each of the wells in the reactor module 1000 block 1012 of FIG. 37. To ensure that liquid is properly delivered into the reaction vessels, elongated well injectors, as shown in FIG. 45 and FIG. 48 below, are connected to the conduit outlets 1212.

Figure 45:
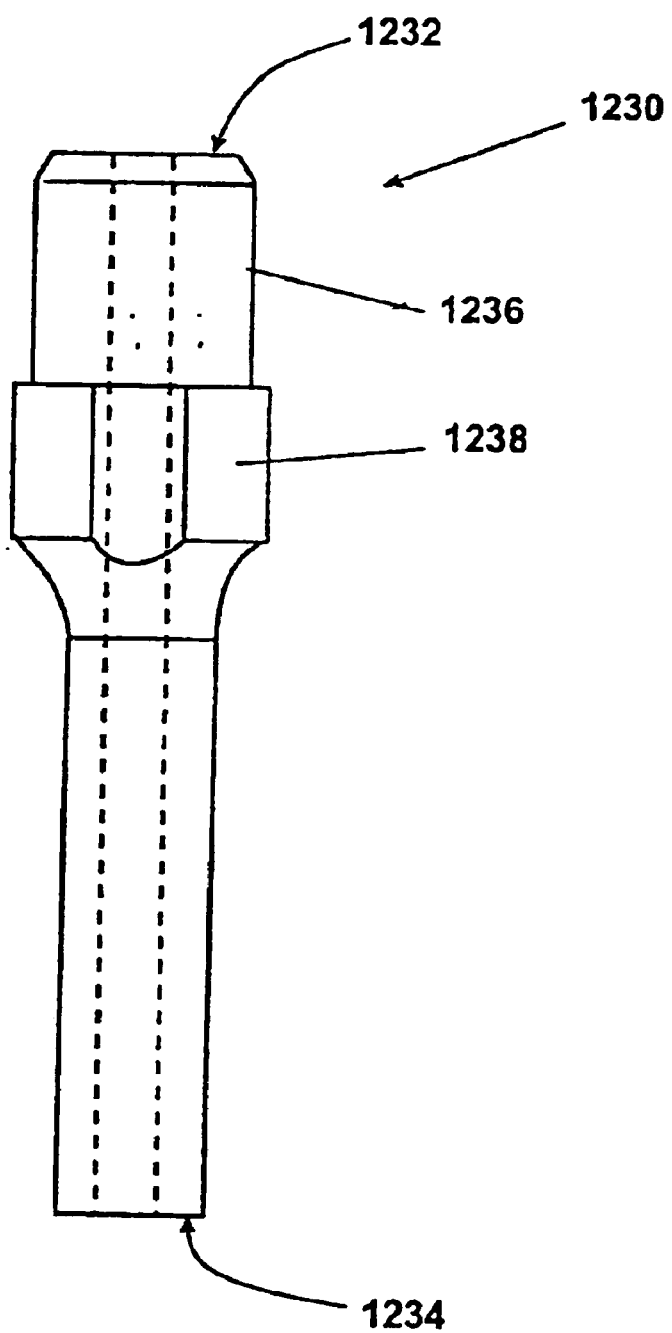
FIG. 45 shows an embodiment of a well injector.

FIG. 45 shows an embodiment of a well injector 1230. The well injector 1230 is a generally cylindrical tube having a first end 1232 and a second end 1234. The well injector 1230 has a threaded outer surface 1236 near the first end 1232 so that it can be attached to threaded conduit outlets 1212 shown in FIG. 44. Flats 1238 located adjacent to the threaded outer surface 1236 assist in twisting the first end 1232 of the well injector 1230 into the conduit outlets 1212. The length of the well injector 1230 can be varied. For example, the second end 1234 of the well injector 1230 may extend into the liquid mixture; alternatively, the second end 1234 of the injector 1230 may extend a portion of the way into the vessel headspace. Typically, the well injector 1230 is made from a chemically resistant plastic, such PEEK, PTFE, and the like.

Figure 46:
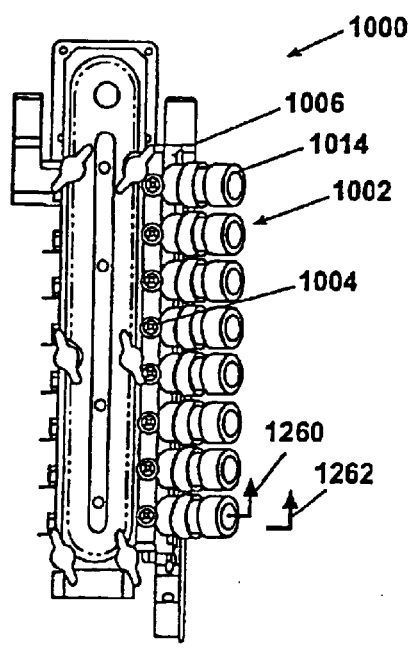
FIG. 46 shows a top view of a reactor module.
Figure 48:
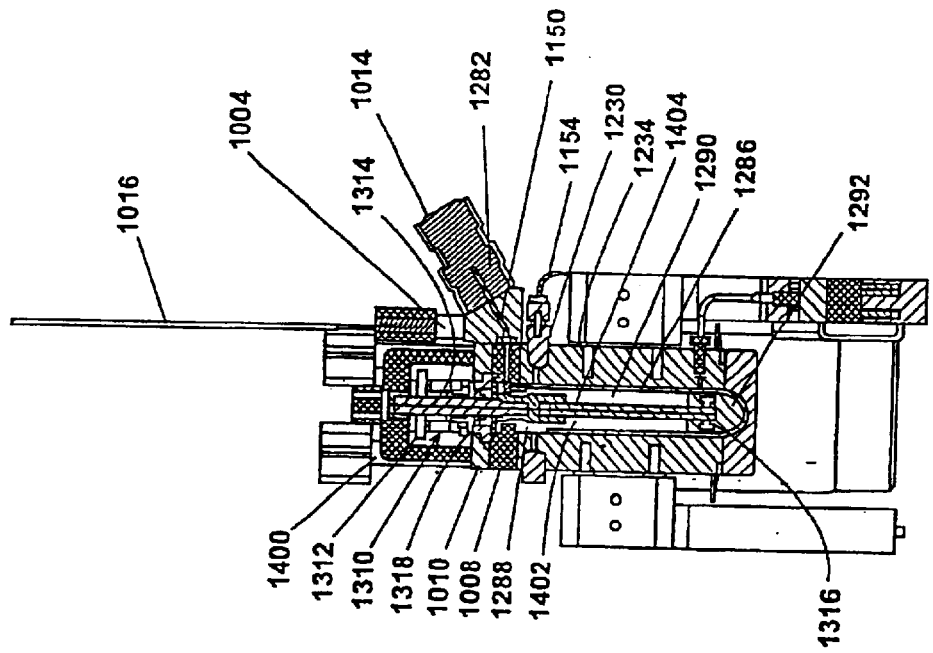
FIG. 48 shows an "open" state of an injector system valve prior during fluid injection, and shows a stirring mechanism and associated seals for maintaining above-ambient pressure in reactor vessels.
Figure 47:
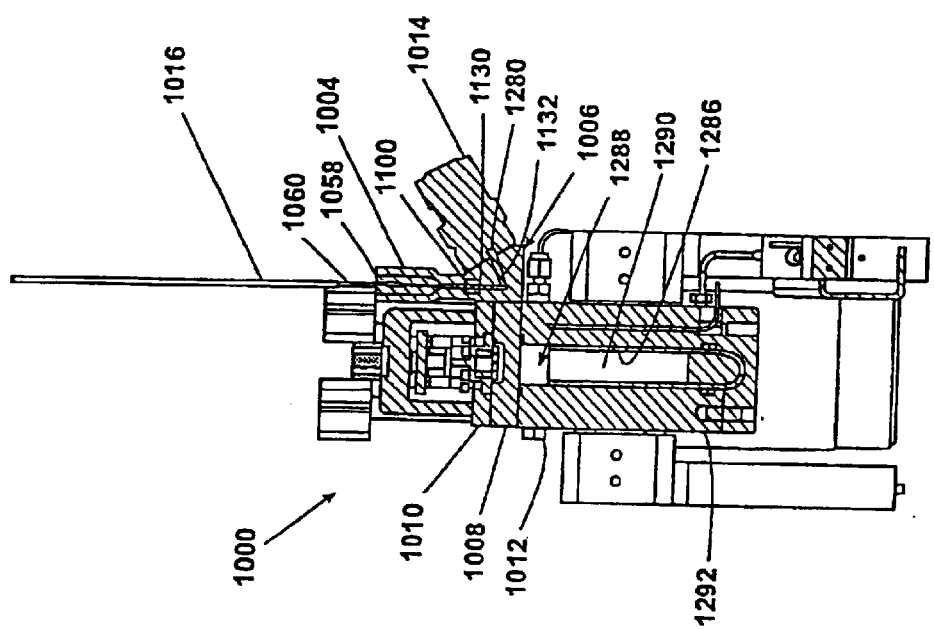
FIG. 47 shows a "closed" state of an injector system valve prior to fluid injection.

Liquid injection can be understood by referring to FIGS. 46–48. FIG. 46 shows a top view of the reactor module 1000, and FIG. 47 and FIG. 48 show, respectively, cross sectional side views of the reactor module 1000 along first and second section lines 1260, 1262 shown in FIG. 46. Prior to injection of a catalyst or other liquid reagent, the probe 1016, which initially contains a first solvent, withdraws a predetermined amount of the liquid reagent from a reagent source. Next, the probe 1016 withdraws a predetermined amount of a second solvent from a second solvent source, resulting in a slug of liquid reagent suspended between the first and second solvents within the probe 1016. Generally, probe manipulations are carried out using a robotic material handling system of the type shown in FIG. 2, and the second solvent is the same as the first solvent.

FIGS. 47 and 48 show the inlet and outlet paths of the valve 1014 prior to, and during, liquid injection, respectively. Once the probe 1016 contains the requisite amount of liquid reagent and solvents, the probe tip 1058 is inserted in the fill port 1004, creating a seal as shown, for example, in FIG. 38 and FIG. 39. The valve 1014 is then opened, and the second solvent, liquid reagent, and a portion of the first solvent are injected into the reactor module 1000 under pressure. From the fill port 1004, the liquid flows into the injector manifold 1006 through one of the first flow paths 1130 that extend from the fill port seats 1100 to the valve inlet seats 1132. The liquid enters the valve 1014 through an inlet port 1280, flows through a valve flow path 1282, and exits the valve 1014 through an outlet port 1284. After leaving the valve 1014, the liquid flows through one of the second flow paths 1150 to a manifold outlet 1154. From the manifold outlet 1154, the liquid flows through the injector adapter plate 1008 within one of the fluid conduits 1182, and is injected into a reactor vessel 1286 or well 1288 through the well injector 1230. In the embodiment shown in FIG. 48, the second end 1234 of the well injector 1230 extends only a fraction of the way into the vessel headspace 1290. In other cases, the second end 1234 may extend into the reaction mixture 1292.

Liquid injection continues until the slug of liquid reagent is injected into the reactor vessel 1286 and the flow path from the fill port 1004 to the second end 1234 of the well injector 1230 is filled with the first solvent. At that point, the valve 1014 is closed, and the probe 1016 is withdrawn from the fill port 1004.

Reactor Vessel Pressure Seal and Magnetic Feed-Through Stirring Mechanism

FIG. 48 shows a stirring mechanism and associated seals for maintaining above-ambient pressure in the reactor vessels 1286. The direct-drive stirring mechanism 1310 is similar to the one shown in FIG. 10, and comprises a gear 1312 attached to a spindle 1314 that rotates a blade or paddle 1316. A dynamic lip seal 1318, which is secured to the upper plate 1010 prevents gas leaks between the rotating spindle 1314 and the upper plate 1010. When newly installed, the lip seal is capable of maintaining pressures of about 100 psig. However, with use, the lip seal 1318, like o-rings and other dynamic seals, will leak due to frictional wear. High service temperatures, pressures, and stirring speeds hasten dynamic seal wear.

Figure 49:
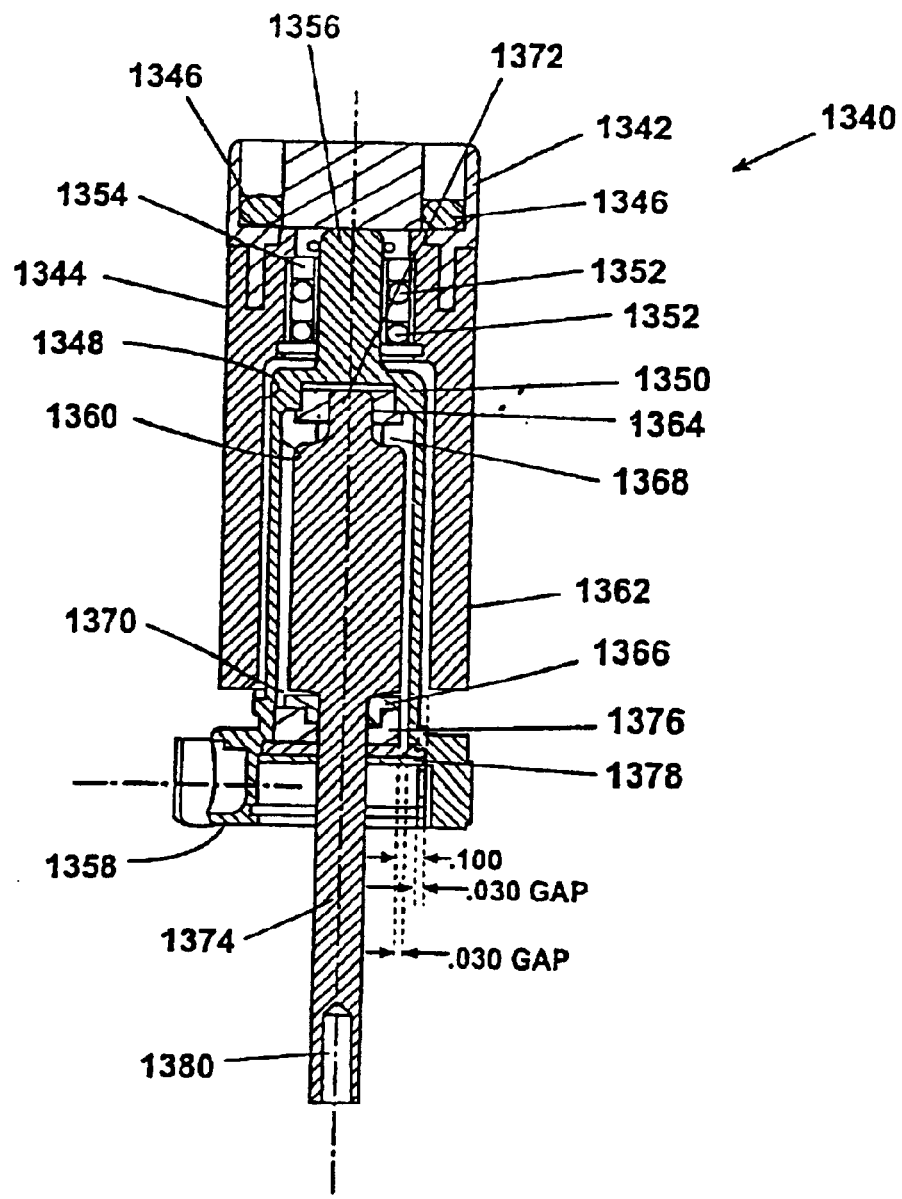
FIG. 49 shows a cross sectional view of a magnetic feed through stirring mechanism that helps minimize gas leaks associated with dynamic seals.

FIG. 49 shows a cross sectional view of a magnetic feed through 1340 stirring mechanism that helps minimize gas leaks associated with dynamic seals. The magnetic feed-through 1340 comprises a gear 1342 that is attached to a magnetic driver assembly 1344 using cap screws 1346 or similar fasteners. The magnetic driver assembly 1344 has a cylindrical inner wall 1348 and is rotatably mounted on a rigid cylindrical pressure barrier 1350 using one or more bearings 1352. The bearings 1352 are located within an annular gap to 1354 between a narrow head portion 1356 of the pressure barrier 1350 and the inner wall 1348 of the magnetic driver assembly 1344. A base portion 1358 of the pressure barrier 1350 is affixed to the upper plate 1010 of the reactor module 1000 shown in FIG. 48 so that the axis of the pressure barrier 1350 is about coincident with the centerline of the reactor vessel 1286 or well 1288. The pressure barrier 1350 has a cylindrical interior surface 1360 that is open only along the base portion 1358 of the pressure barrier 1350. Thus, the interior surface 1360 of the pressure barrier 1350 and the reactor vessel 1286 or well 1288 define a closed chamber.

As can be seen in FIG. 49, the magnetic feed through 1340 further comprises a cylindrical magnetic follower 1362 rotatably mounted within the pressure barrier 1350 using first 1364 and second 1366 flanged bearings. The first 1364 and second 1366 flanged bearings are located in first 1368 and second 1370 annular regions 1368 delimited by the interior surface 1360 of the pressure barrier 1350 and relatively narrow head 1372 and leg 1374 portions of the magnetic follower 1362, respectively. A keeper 1376 and retaining clip 1378 located within the second annular region 1370 adjacent to the second flanged bearing 1366 help minimize axial motion of the magnetic follower 1362. A spindle (not shown) attached to the free end 1380 of the leg 1374 of the magnetic follower 1362, transmits torque to the paddle 1316 immersed in the reaction mixture 1292 shown in FIG. 48.

During operation, the rotating gear 1342 and magnetic driver assembly 1344 transmit torque through the rigid pressure barrier 1350 to the cylindrical magnetic follower 1362. Permanent magnets (not shown) embedded in the magnetic driver assembly 1344 have force vectors lying in planes about perpendicular to the axis of rotation 1382 of the magnetic driver assembly 1344 and follower 1362. These magnets are coupled to permanent magnets (not shown) that are similarly aligned and embedded in the magnetic follower 1362. Because of the magnetic coupling, rotation of the driver assembly 1344 induces rotation of the follower 1362 and stirring blade or paddle 1316 of FIG. 48. The follower 1362 and paddle 1316 rotate at the same frequency as the magnetic driver assembly, though, perhaps, with a measurable phase lag.

Removable and Disposable Stirrer

The stirring mechanism 1310 shown in FIG. 48 includes a multi-piece spindle 1314 comprising an upper spindle portion 1400, a coupler 1402, and a removable stirrer 1404. The multi-piece spindle 1314 offers certain advantages over a one-piece spindle. Typically, only the upper drive shaft 1400 and the coupler 1402 are made of a high modulus material such as stainless steel: the removable stirrer 1404 is made of a chemically resistant and inexpensive plastic, such as PEEK, PTFE, and the like. In contrast, one-piece spindles, though perhaps coated with PTFE, are generally made entirely of a relatively expensive high modulus material, and are therefore normally reused. However, one-piece spindles are often difficult to clean after use, especially following a polymerization reaction. Furthermore, reaction product may be lost during cleaning, which leads to errors in calculating reaction yield. With the multi-piece spindle 1314, one discards the removable stirrer 1404 after a single use, eliminating the cleaning step. Because the removable stirrer 1404 is less bulky than the one-piece spindle, it can be included in certain post-reaction characterizations, including product weighing to determine reaction yield.

Figure 50:
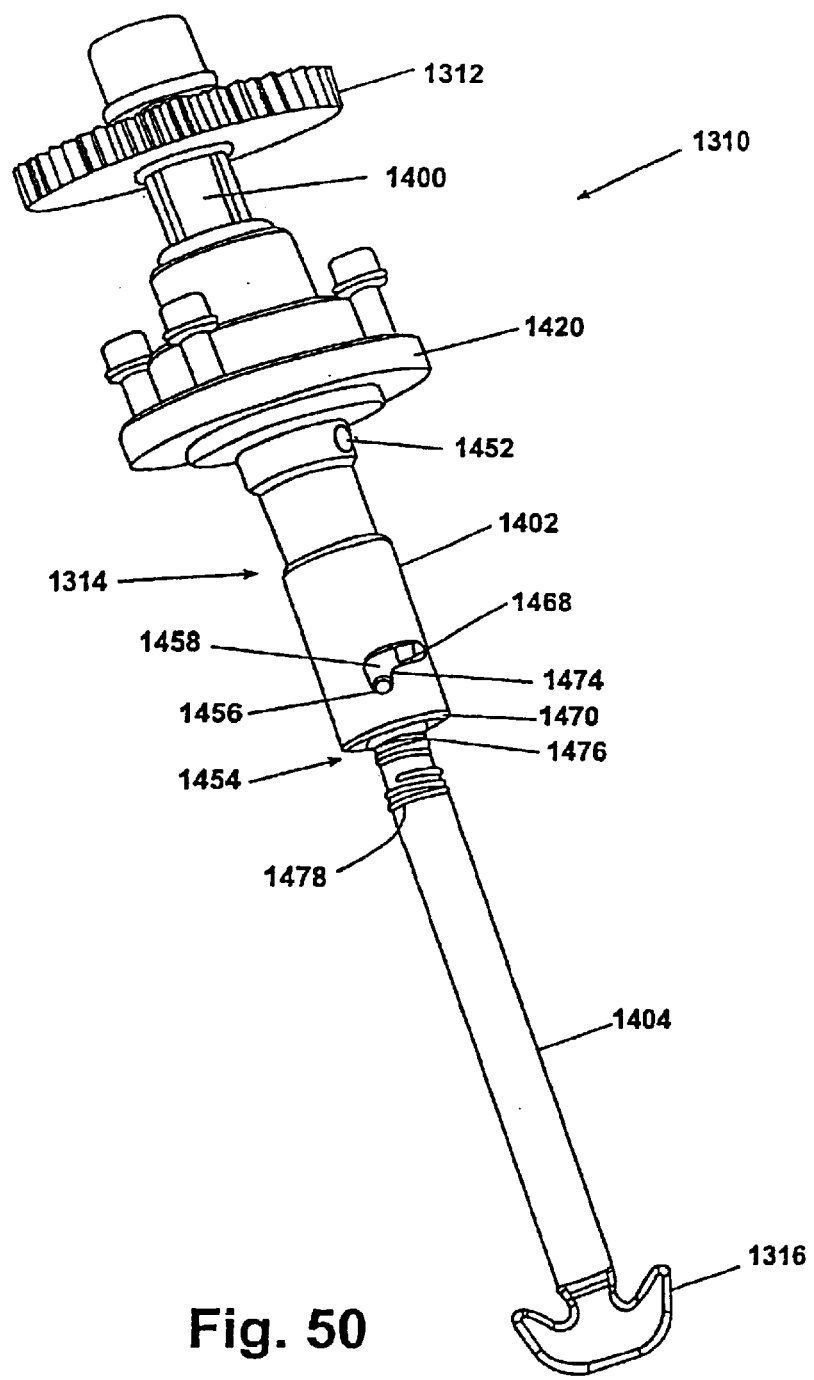
FIG. 50 shows a perspective view of a stirring mechanism shown in FIG. 48, and provides details of a multi-piece spindle.

FIG. 50 shows a perspective view of the stirring mechanism 1310 of FIG. 48, and provides details of the multi-piece spindle 1314. A gear 1312 is attached to the upper spindle portion 1400 of the multi-piece spindle 1314. The upper spindle 1400 passes through a pressure seal assembly 1420 containing a dynamic lip seal, and is attached to the removable stirrer 1404 using the coupler 1402. Note that the removable stirrer 1404 can also be used with the magnetic feed through stirring mechanism 1340 illustrated in FIG. 49. In such cases, the upper spindle 1400 is eliminated and the leg 1374 of the cylindrical magnetic follower 1362 or the coupler 1402 or both are modified to attach the magnetic follower 1362 to the removable stirrer 1404.

Figure 51:
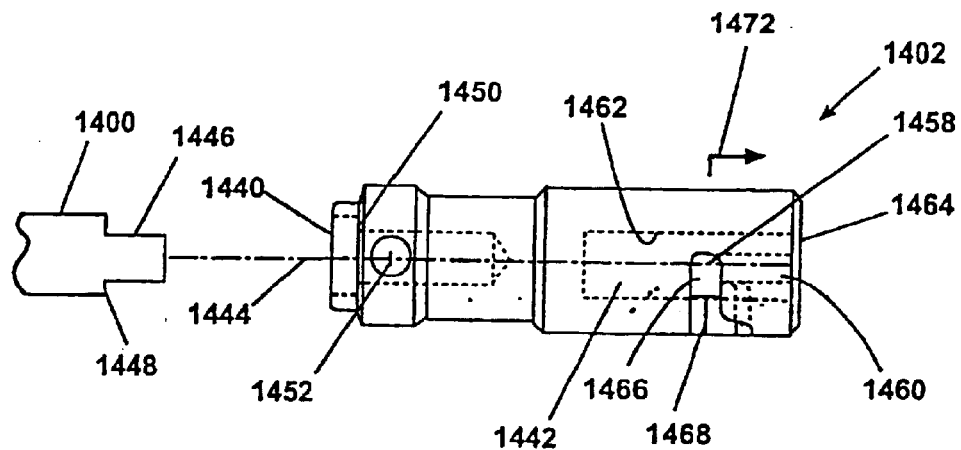
FIG. 51 shows details of a coupler portion of a multi-piece spindle.

FIG. 51 shows details of the coupler 1402, which comprises a cylindrical body having first 1440 and second 1442 holes centered along an axis of rotation 1444 of the coupler 1402. The first hole 1440 is dimensioned to receive a cylindrical end 1446 of the upper spindle 1400. A shoulder 1448 formed along the periphery of the upper spindle 1400 rests against an annular seat 1450 located within the first hole 1440. A set screw (not shown) threaded into a locating hole 1452 prevents relative axial and rotational motion of the upper spindle 1400 and the coupler 1402.

Referring to FIGS. 50 and 51, the second hole 1442 of the coupler 1402 is dimensioned to receive a first end 1454 of the removable stirrer 1404. A pin 1456, which is embedded in the first end 1454 of the removable stirrer, cooperates with a locking mechanism 1458 located on the coupler 1402, to prevent relative rotation of the coupler 1402 and the removable stirrer 1404. The locking mechanism 1458 comprises an axial groove 1460 formed in an inner surface 1462 of the coupler. The groove 1460 extends from an entrance 1464 of the second hole 1442 to a lateral portion 1466 of a slot 1468 cut through a wall 1470 of the coupler 1402.

Figure 52:
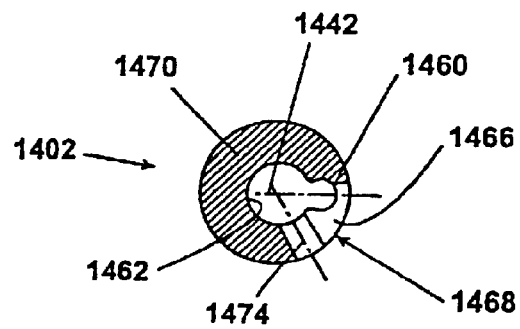
FIG. 52 shows a cross sectional view of the coupler shown in FIG. 51.

As shown in FIG. 52, which is a cross sectional view of the coupler 1402 along a section line 1472, the lateral portion 1466 of the slot 1468 extends about 60 degrees around the circumference of the coupler 1402 to an axial portion 1474 of the slot 1468. To connect the removable stirrer 1404 to the coupler 1402, the first end 1454 of the removable stirrer 1404 is inserted into the second hole 1442 and then rotated so that the pin 1456 travels in the axial groove 1460 and lateral portion 1466 of the slot 1468. A spring 1476, mounted between the coupler 1402 and a shoulder 1478 formed on the periphery of the removable stirrer 1404, forces the pin 1456 into the axial portion 1474 of the slot 1468.

Figures 50A, 50B:
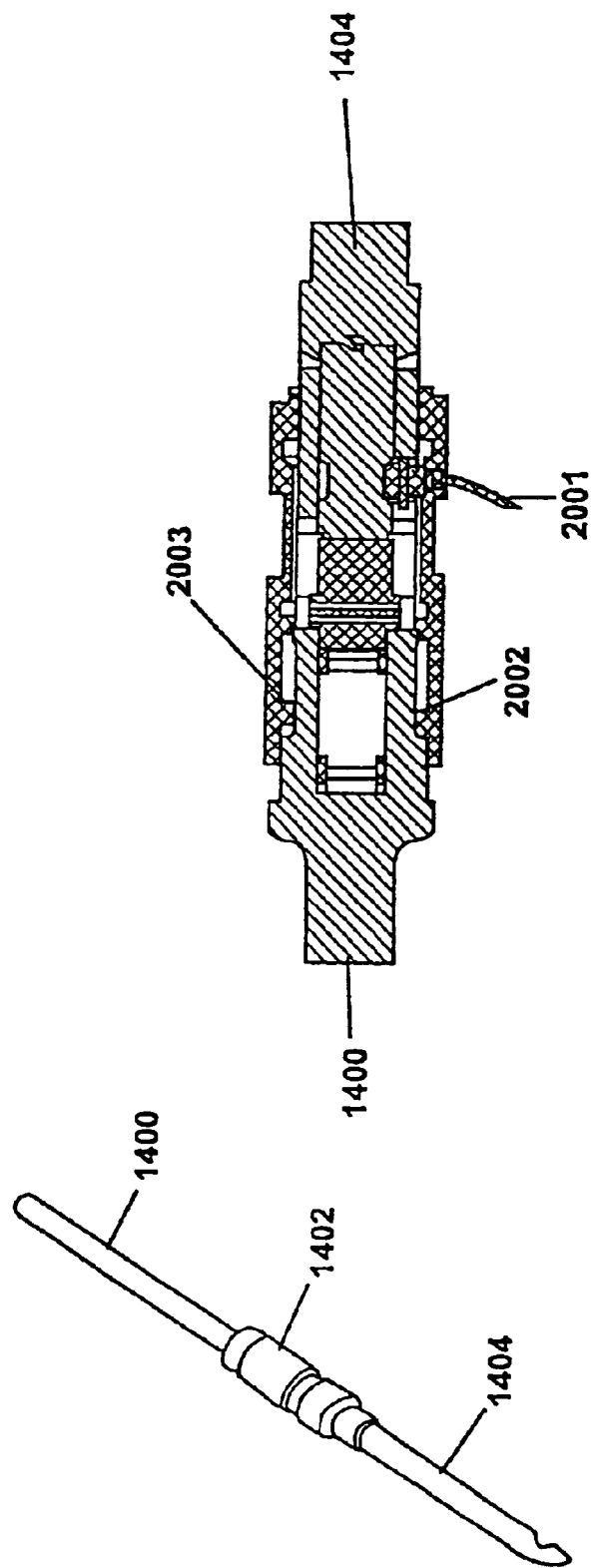
FIG. 50A shows an alternative design for a multi-piece spindle.
FIG. 50B shows details of the alternative design for a multi-piece spindle shown in FIG. 50B.

An alternative design for the multi-piece spindle 1314 is shown in FIG. 50A, which has an upper spindle portion 1400, a coupler 1402 and a removable stirrer 1404. The details of this alternative design are shown in FIG. 50B. This alternative design is essentially a spring lock mechanism that allows for quick removal of the removable stirrer 1404. The removable stirrer 1404 is locked in to the coupling mechanism by a series of balls 2001 that are held into a groove in the removable stirrer 1404 by a collar 2002, which is part of the coupler 1402. The removable stirrer 1404 is released by pulling the collar 2002 back against a spring 2003 and allowing the balls 2001 to fall into a pocket in the collar 2002 and releasing the removable stirrer.

Parallel Pressure Reactor Control and Analysis

Figure 53:
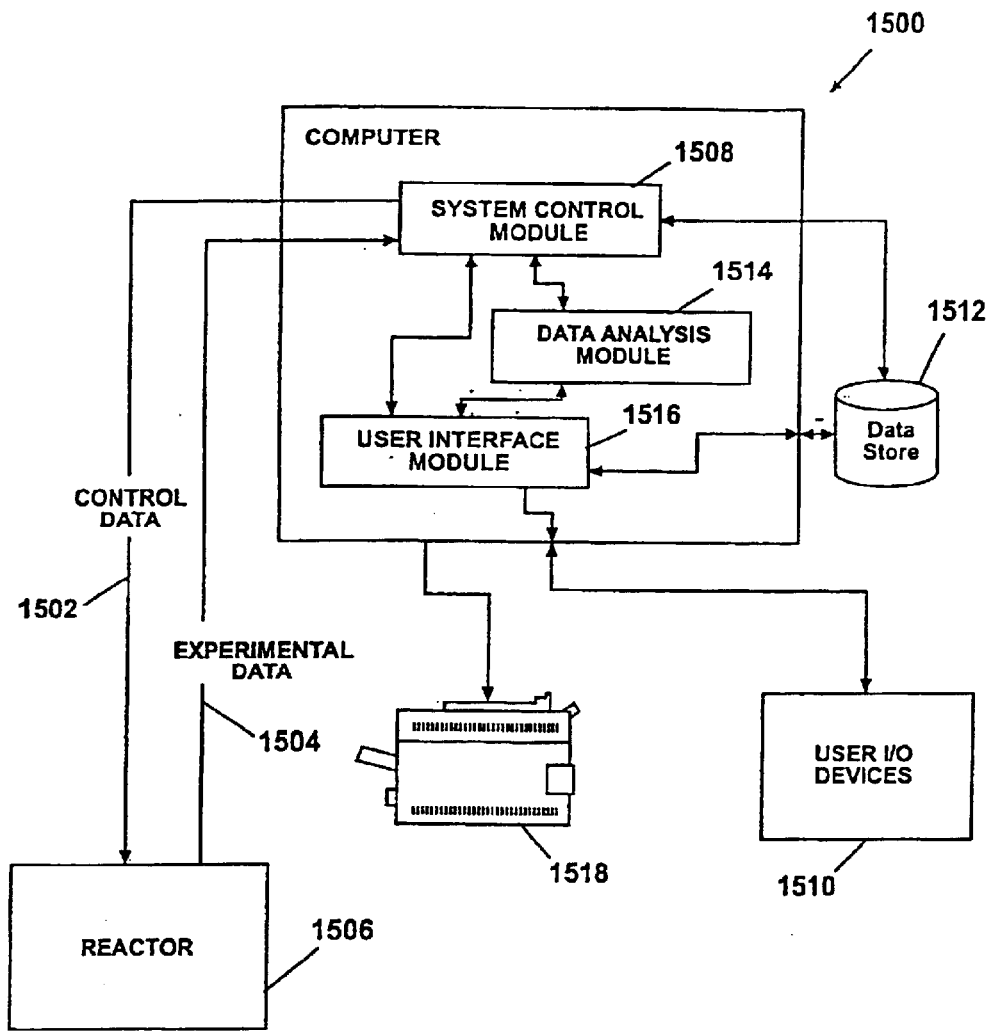
FIG. 53 is a block diagram of a data processing system showing an implementation of the invention.

FIG. 53 shows one implementation of a computer-based system for monitoring the progress and properties of multiple reactions in situ. Reactor control system 1500 sends control data 1502 to and receives experimental data 1504 from reactor 1506. As will be described in more detail below, in one embodiment reactor 1506 is a parallel polymerization reactor and the control and experimental data 1502 and 1504 include set point values for temperature, pressure, time and stirring speed as well as measured experimental values for temperature and pressure. Alternatively, in other embodiments reactor 1506 can be any other type of parallel reactor or conventional reactor, and data 1502, 1504 can include other control or experimental data. System control module 1508 provides reactor 1506 with control data 1502 based on system parameters obtained from the user through user I/O devices 1510, such as a display monitor, keyboard or mouse. Alternatively, system control module 1508 can retrieve control data 1502 from storage 1512.

Reactor control system 1500 acquires experimental data 1504 from reactor 1506 and processes the experimental data in system control module 1508 and data analysis module 1514 under user control through user interface module 1516. Reactor control system 1500 displays the processed data both numerically and graphically through user interface module 1516 and user I/O devices 1510, and optionally through printer 1518.

Figure 54:
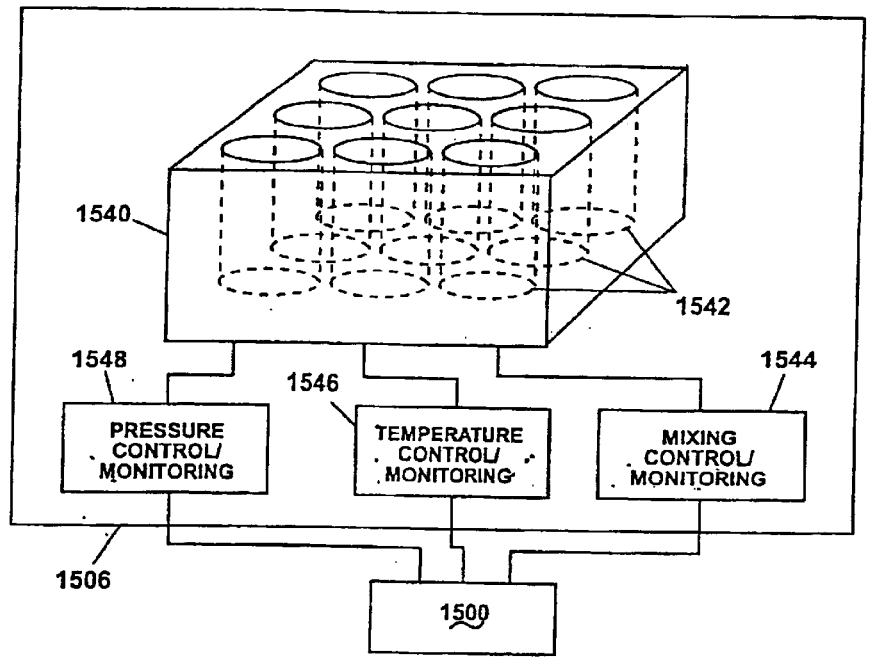
FIGS. 54–57 are schematic diagrams of a parallel reactor suitable for use with the invention.

FIG. 54 illustrates an embodiment of reactor 1506 in which pressure, temperature, and l=mixing intensity are automatically controlled and monitored. Reactor 1506 includes reactor block 1540, which contains sealed reactor vessels 1542 for receiving reagents. In one embodiment, reactor block 1540 is a single unit containing each of reactor vessels 1542. Alternatively, reactor block 1540 can include a number of reactor block modules, each of which contains a number of reactor vessels 1542. Reactor 1506 includes a mixing control and monitoring system 1544, a temperature control and monitoring system 1546 and a pressure control and monitoring system 1548. These systems communicate with reactor control system 1500.

Figure 55:
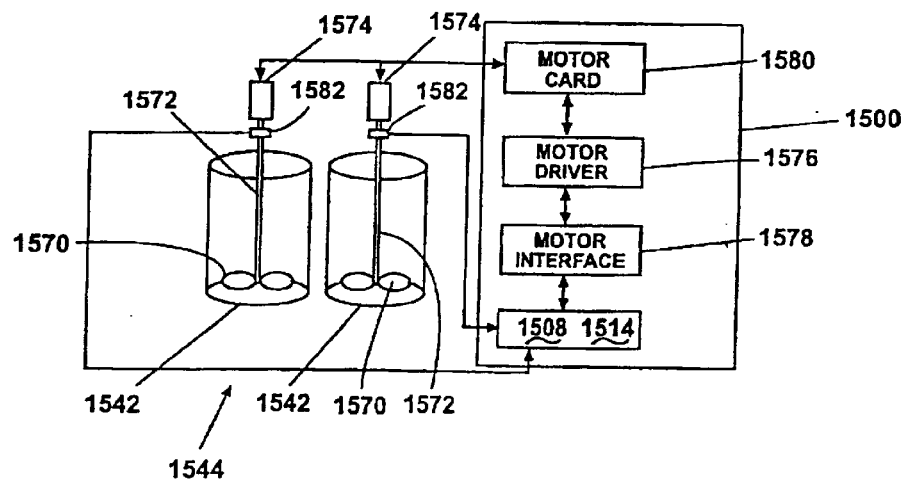

The details of mixing control and monitoring system 1544 are illustrated in FIG. 55. Each of reactor vessels 1542 contains a stirrer 1570 for mixing the vessel contents. In one embodiment, stirrers 1570 are stirring blades mounted on spindles 1572 and driven by motors 1574. Separate motors 1574 can control each individual stirrer 1570; alternatively, motors 1574 can control groups of stirrers 1570 associated with reactor vessels 1542 in separate reactor blocks. In another embodiment, magnetic stirring bars or other known stirring mechanisms can be used. System control module 1508 provides mixing control signals to stirrers 1570 through interface 1576, 1578, and one or more motor cards

1580. Interface 1576, 1578 can include a commercial motor driver 1576 and motor interface software 1578 that provides additional high level motor control, such as the ability to initialize motor cards 1580, to control specific motors or motor axes (where each motor 1580 controls a separate reactor block), to set motor speed and acceleration, and to change or stop a specified motor or motor axis.

Mixing control and monitoring system 1544 can also include torque monitors 1582, which monitor the applied torque in each of reactor vessels 1542. Suitable torque monitors 1582 can include optical sensors and magnetic field sensors mounted on spindles 1572, or strain gauges (not shown), which directly measure the applied torque and transmit torque data to system control module 1508 and data analysis module 1514. Monitors 1582 can also include encoders, resolvers, Hall effect sensors and the like, which may be integrated into motors 1574. These monitors measure the power required to maintain a constant spindle 1572 rotational speed, which is related to applied torque.

Figure 56:
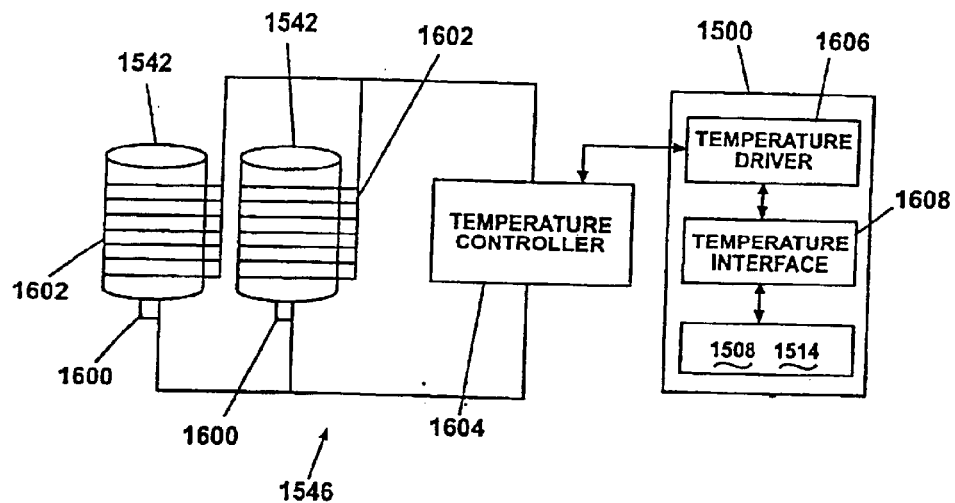

Referring to FIG. 56, temperature control and monitoring system 1546 includes a temperature sensor 1600 and a heating element 1602 associated with each reactor vessel 1542 and controlled by temperature controller 1604. Suitable heating elements 1602 can include thin filament resistance heaters, thermoelectric devices, thermistors, or other devices for regulating vessel temperature. Heating elements can include devices for cooling, as well as heating, reactor vessels 1542. System control unit 1508 transmits temperature control signals to heating elements 1602 through interface 1606, 1608 and temperature controller 1604. Interface 1606, 1608 can include a commercial temperature device driver 1606 implemented to use hardware such as an RS232 interface, and temperature interface software 1608 that provides additional high level communication with temperature controller 1604, such as the ability to control the appropriate communication port, to send temperature set points to temperature controller 1604, and to receive temperature data from temperature controller 1604.

Suitable temperature sensors 1600 can include thermocouples, resistance thermoelectric devices, thermistors, or other temperature sensing devices. Temperature controller 1604 receives signals from temperature sensors 1600 and transmits temperature data to reactor control system 1500. Upon determining that an increase or decrease in reactor vessel temperature is appropriate, system control module 1508 transmits temperature control signals to heating elements 1602 through heater controller 1604. This determination can be based on temperature parameters entered by the user through user interface module 1516, or on parameters retrieved by system control module 1508 from storage. System control module 1508 can also use information received from temperature sensors 1600 to determine whether an increase or decrease in reactor vessel temperature is necessary.

Figure 57:
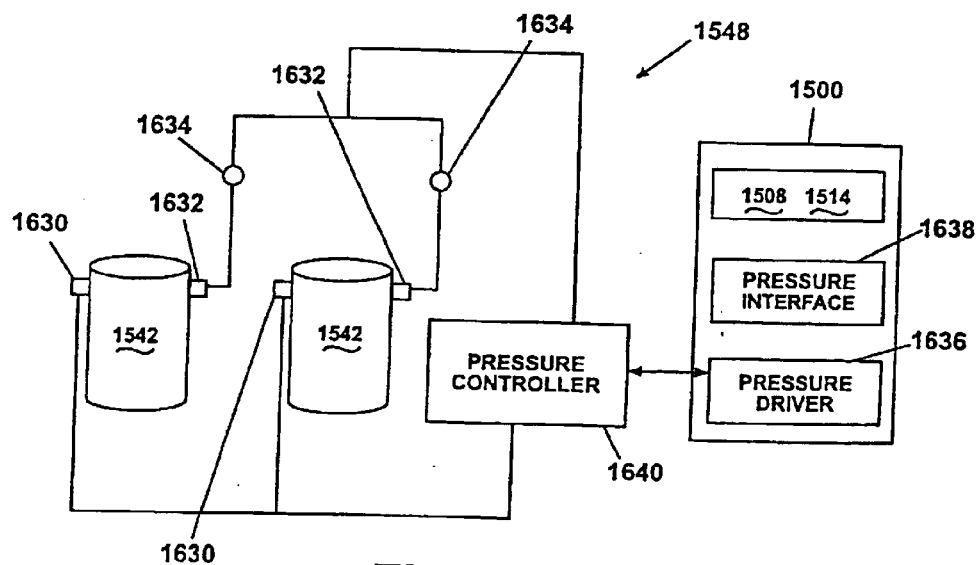

As shown in FIG. 57, pressure control and monitoring system 1548 includes a pressure sensor 1630 associated with each reactor vessel 1542. Each reactor vessel 1542 is furnished with a gas inlet/outlet 1632 that is controlled by valves 1634. System control module 1508 controls reactor vessel pressure through pressure interface 1636, 1638 and pressure controller 1640. Pressure interface 1636, 1638 can be implemented in hardware, software or a combination of both. Pressure controller 1640 transmits pressure control signals to valves 1634 allowing gases to enter or exit reactor vessels 1542 through inlet/outlet 1632 as required to maintain reactor vessel pressure at a level set by the user through user interface 1516.

Pressure sensors 1630 obtain pressure readings from reactor vessels 1542 and transmit pressure data to system control module 1508 and data analysis module 1514 through pressure controller 1640 and interface 1636, 1638. Data analysis module 1514 uses the pressure data in calculations such as the determination of the rate of production of gaseous reaction products or the rate of consumption of gaseous reactants, discussed in more detail below. System control module 1508 uses the pressure data to determine when adjustments to reactor vessel pressure are required, as discussed above.

Figure 58:
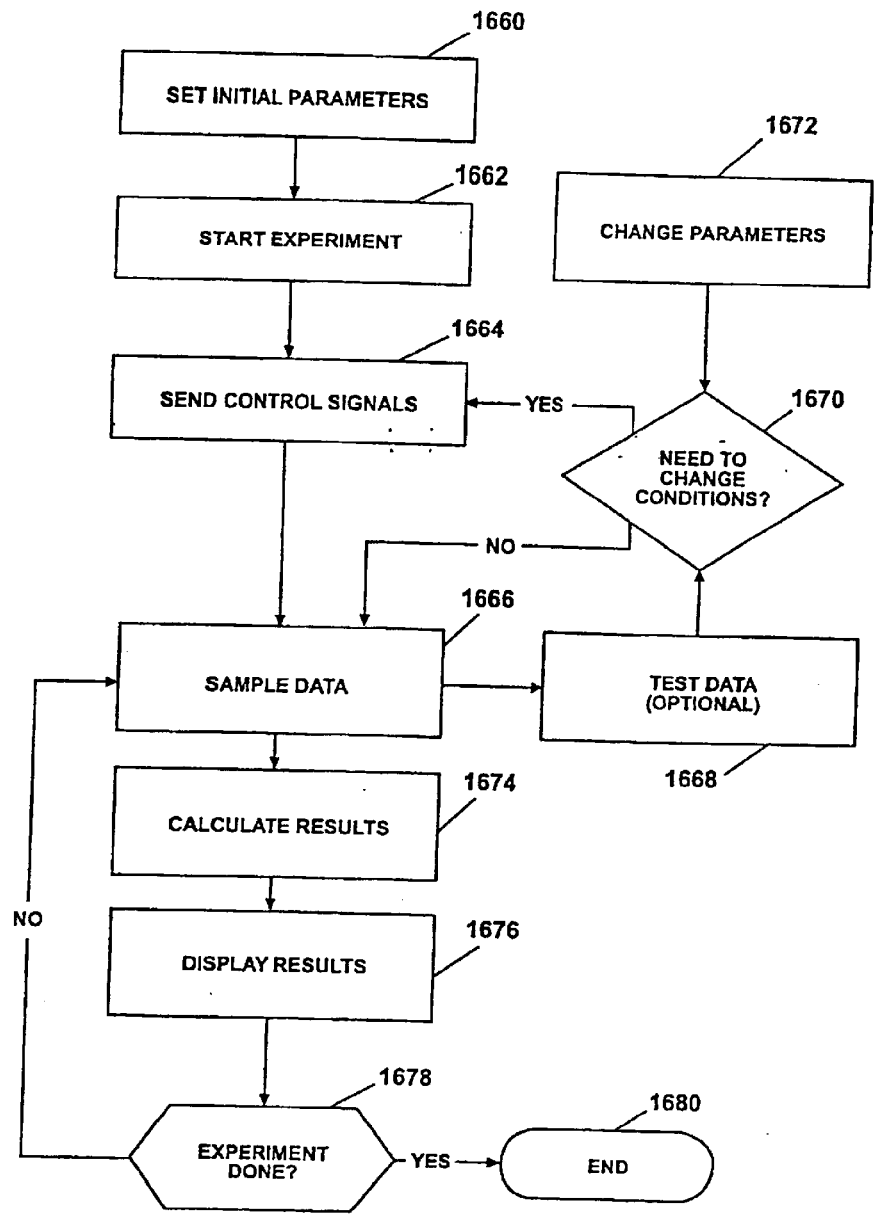
FIG. 58 is a flow diagram of a method of controlling and analyzing a parallel chemical reaction.

FIG. 58 is a flow diagram illustrating the operation of a reactor control system 1500. The user initializes reactor control system 1500 by setting the initial reaction parameters, such as set points for temperature, pressure and stirring speed and the duration of the experiment, as well as selecting the appropriate hardware configuration for the experiment (step 1660). The user can also set other reaction parameters that can include, for example, a time at which additional reagents, such as a liquid co-monomer in a co-polymerization experiment, should be added to reaction vessels 1542, or a target conversion percentage at which a quenching agent should be added to terminate a catalytic polymerization experiment. Alternatively, reactor control system 1500 can load initial parameters from storage 1512. The user starts the experiment (step 1662). Reactor control system 1500 sends control signals to reactor 110, causing motor, temperature and pressure control systems 1544, 1546 and 1548 to bring reactor vessels 1542 to set point levels (step 1664).

Reactor control system 1500 samples data through mixing monitoring system 1544, temperature monitoring system 1546 and pressure monitoring system 1548 at sampling rates, which may be entered by the user (step 1666). Reactor control system 1500 can provide process control by testing the experimental data, including sampled temperature, pressure or torque values as well as elapsed time, against initial parameters (step 1668). Based on these inputs, reactor control system 1500 sends new control signals to the mixing, temperature and/or pressure control and monitoring systems of reactor 1506 (steps 1670, 1664). These control signals can also include instructions to a material handling robot to add material, such as a reagent or a catalyst quenching agent, to one or more reactor vessels based upon experimental data such as elapsed time or percent conversion calculated as discussed below. The user can also enter new parameters during the course of the experiment, such as changes in motor speed, set points for temperature or pressure, or termination controlling parameters such as experiment time or percent conversion target (step 1672), which may also cause reactor control system 1500 to send new control signals to reactor 1506 (steps 1672, 1670, 1664).

Data analysis module 1514 performs appropriate calculations on the sampled data (step 1674), as will be discussed below, and the results are displayed on monitor 1510 (step 1676). Calculated results and/or sampled data can be stored in data storage 1512 for later display and analysis. Reactor control system 1500 determines whether the experiment is complete—for example, by determining whether the time for the experiment has elapsed (step 1678). Reactor control system 1500 can also determine whether the reaction occurring in one or more of reactor vessels 1542 has reached a specified conversion target based on results calculated in step 1674; in that case, reactor control system 1500 causes the addition of a quenching agent to the relevant reactor vessel or vessels as discussed above, terminating the reaction in that vessel. For any remaining reactor vessels, reactor control system 1150 samples additional data (step 1666) and the cycle begins anew. When all reactor vessels 1542 in reactor block 1540 have reached a specified termination condition, the experiment is complete (step 1680). The user can also cause the reaction to terminate by aborting the experiment at any time. It should be recognized that the steps illustrated in FIG. 58 are not necessarily performed in the order shown; instead, the operation of reactor control system 1500 can be event driven, responding, for example, to user events, such as changes in reaction parameters, or system generated periodic events.

Analysis of Experimental Data

The type of calculation performed by data analysis module 1514 (step 1674) depends on the nature of the experiment. As discussed above, while an experiment is in progress, reactor control system 1500 periodically receives temperature, pressure and/or torque data from reactor 1506 at sampling rates set by the user (step 1666). System control module 1508 and data analysis module 1514 process the data for use in screening materials or for performing quantitative calculations and for display by user interface module 1516 in formats such as those shown in FIGS. 63–64 and 65.

Reactor control system 1500 uses temperature measurements from temperature sensors 1600 as a screening criteria or to calculate useful process and product variables. For instance, in one implementation, catalysts of exothermic reactions are ranked based on peak reaction temperature reached within each reactor vessel, rates of change of temperature with respect to time, or total heat released over the course of reaction. Typically, the best catalysts of an exothermic reaction are those that, when combined with a set of reactants, result in the greatest heat production in the shortest amount of time. In other implementations, reactor control system 1500 uses temperature measurements to compute rates of reaction and conversion.

In addition to processing temperature data as a screening tool, in another implementation, reactor control system 1500 uses temperature measurement combined with proper thermal management and design of the reactor system—to obtain quantitative calorimetric data. From such data, reactor control system 1500 can, for example, compute instantaneous conversion and reaction rate, locate phase transitions (e.g., melting point, glass transition temperature) of reaction products, or measure latent heats to deduce structural information of polymeric materials, including degree of crystallinity and branching. For details of calorimetric data measurement and use, see description accompanying FIG. 9 and equations I–V.

Reactor control system 1500 can also monitor mixing variables such as applied stirring blade torque in order to determine the viscosity of the reaction mixture and related properties. Reactor control system 1500 can use such data to monitor reactant conversion and to rank or characterize materials based on molecular weight or particle size. See, for example, the description of equations VI–VIII above.

Reactor control system 1500 can also assess reaction kinetics by monitoring pressure changes due to production or consumption of various gases during reaction. Reactor control system 1500 uses pressure sensors 1630 to measure changes in pressure in each reactor vessel headspace—the volume within each vessel that separates the liquid reagents from the vessel's sealed cap. During reaction, any changes in the head space pressure, at constant temperature, reflect changes in the amount of gas present in the head space. As described above (equation XI), reactor system 1500 uses this pressure data to determine the molar production or consumption rate, $r_i$, of a gaseous component.

Operation of a Reactor Control System

Figure 59:
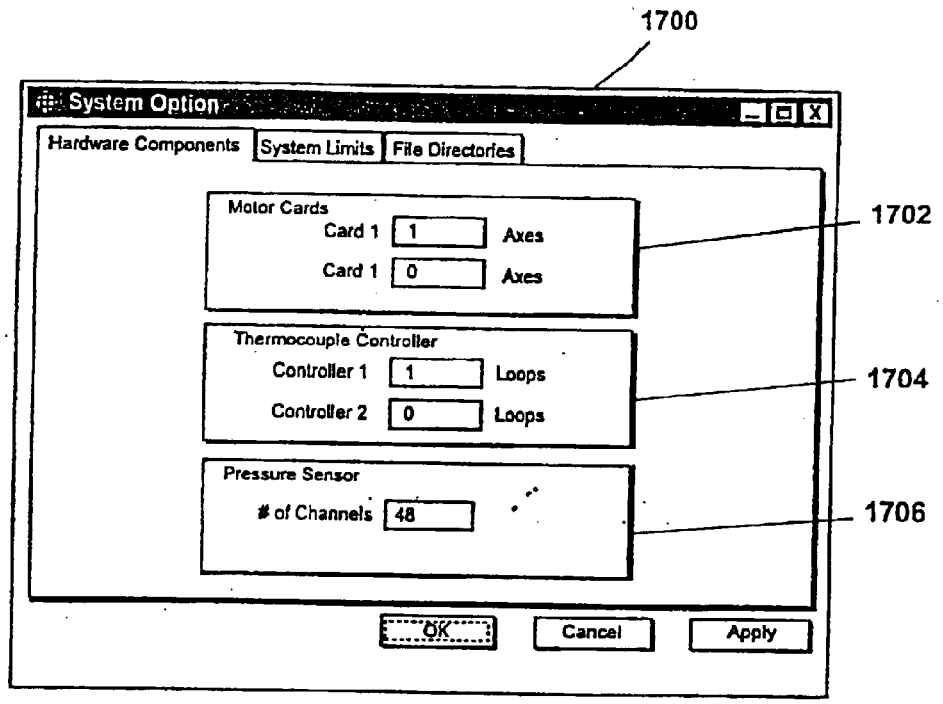
FIG. 59 is an illustration of a dialog window for user input of system configuration information.

Referring to FIG. 59, reactor control system 1500 receives system configuration information from the user through system configuration window 1700, displayed on monitor 1510. System configuration window 1700 allows the user to specify the appropriate hardware components for an experiment. For example, the user can choose the number of motor cards 1580 and the set a number of motor axes per card in motor pane 1702. Temperature controller pane 1704 allows the user to select the number of separate temperature controllers 1604 and the number of reactor vessels (the number of feedback control loops) per controller. In pressure sensor pane 1706, the user can set the number of pressure channels corresponding to the number of reactor vessels in reactor 1506. The user can also view the preset safety limits for motor speed, temperature and pressure through system configuration window 1700.

Figure 60:
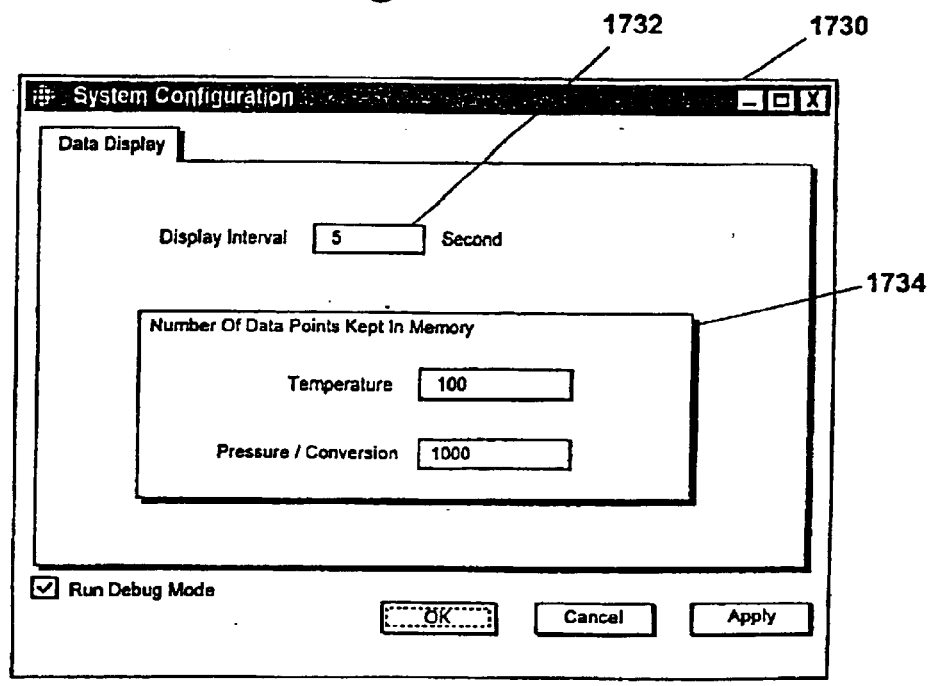
FIG. 60 is an illustration of a dialog window for user input of data display information.

As shown in FIG. 60, reactor control system 1500 receives data display information from the user through system option window 1730. Display interval dialog 1732 lets the user set the refresh interval for data display. The user can set the number of temperature and pressure data points kept in memory in data point pane 1734.

Figure 61:
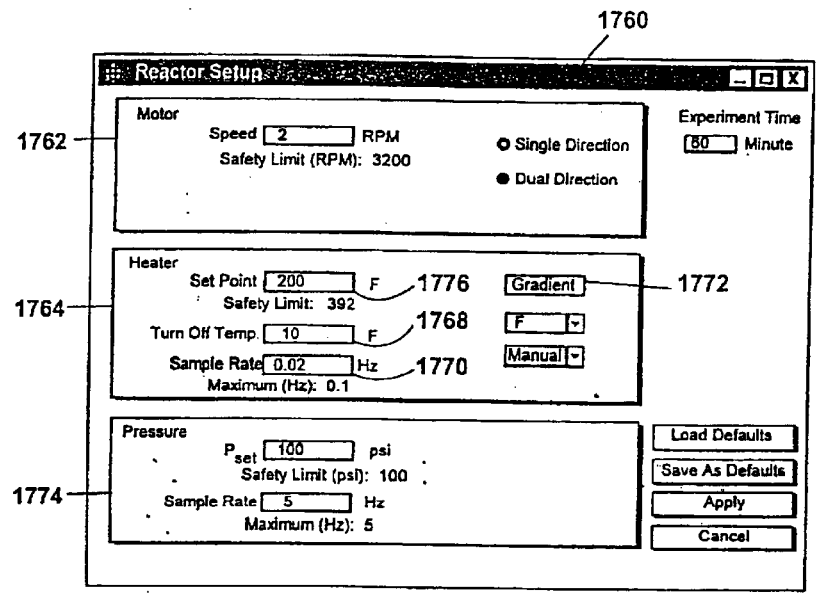
FIG. 61 is an illustration of a dialog window for user input of parallel reactor parameters.

At any time before or during an experiment, the user can enter or modify reaction parameters for each reactor vessel 1542 in reactor block 1540 using reactor setup window 1760, shown in FIG. 61. In motor setup pane 1762, the user can set a motor speed (subject to any preset safety limits), and can also select single or dual direction motor operation. The user can specify temperature parameters in temperature setup pane 1764. These parameters include temperature set point 1766, turn off temperature 1768, sampling rate 1770, as well as the units for temperature measurement and temperature controller operation modes. By selecting gradient button 1772, the user can also set a temperature gradient, as will be discussed below. Pressure parameters, including a pressure set point and sampling rate, can be set in pressure setup pane 1774. Panes 1762, 1764 and 1774 can also display safety limits for motor speed, temperature and pressure, respectively. The values illustrated in FIG. 61 are not intended to limit this invention and are illustrative only. Reactor setup window 1760 also lets the user set a time for the duration of the experiment. Reactor setup window 1760 lets the user save any settings as defaults for future use, and load previously saved settings.

Figure 62:
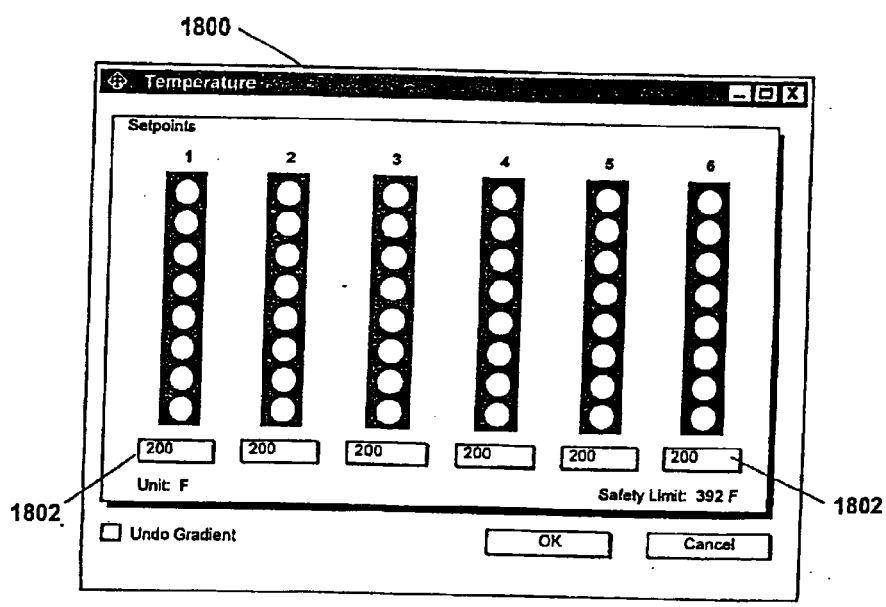
FIG. 62 is an illustration of a dialog window for user input of a temperature gradient for reactor blocks in a parallel reactor.

FIG. 62 illustrates the setting of a temperature gradient initiated by selecting gradient button 1772. In gradient setup window 1800, the user can set a temperature gradient across reactor 1506 by entering different temperature set points 1802 for each reactor block module of a multi-block reactor 1506. As with other setup parameters, such temperature gradients can be saved in reactor setup window 1760.

Figure 63:
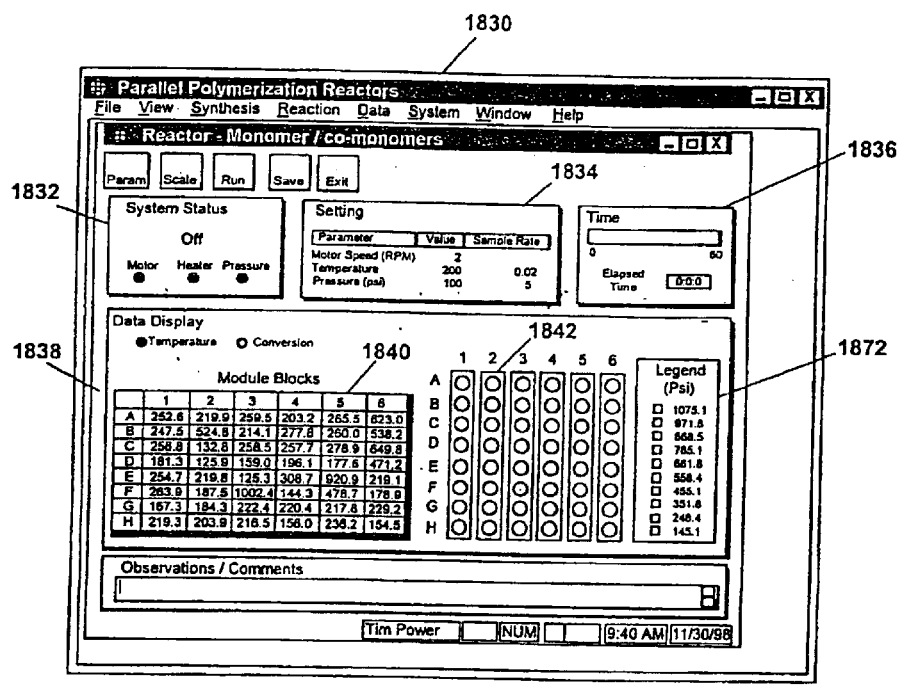
FIGS. 63–64 are illustrations of windows displaying system status and experimental results for a parallel reactor.
Figure 64:
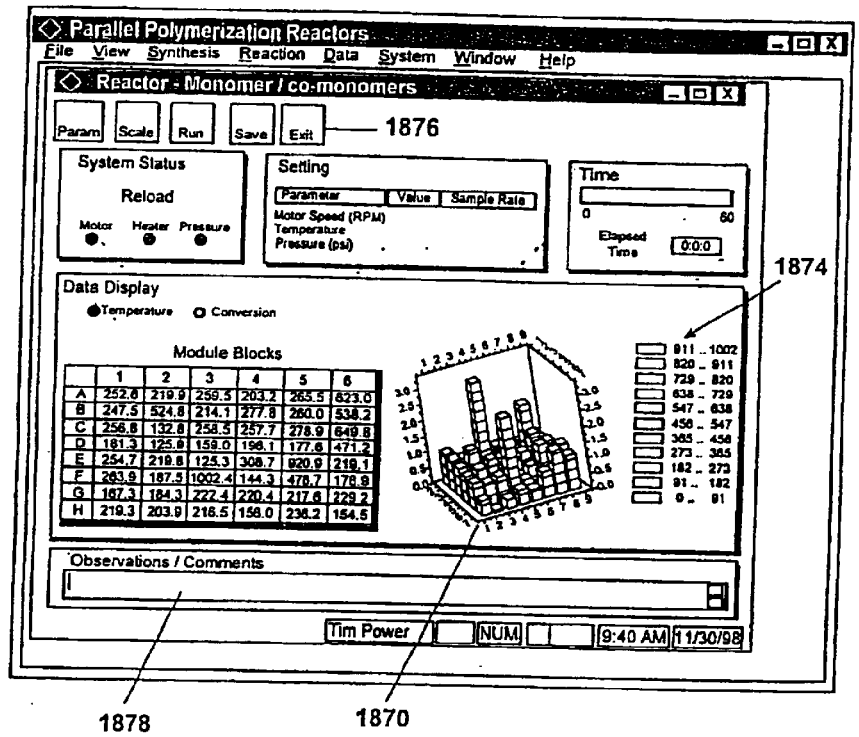

Referring to FIG. 63, the user can monitor an experiment in reaction window 1830. System status pane 1832 displays the current system status, as well as the status of the hardware components selected in system configuration window 1700. Setting pane 1834 and time pane 1836 display the current parameter settings and time selected in reactor setup window 1760, as well as the elapsed time in the experiment. Experimental results are displayed in data display pane 1838, which includes two dimensional array 1840 for numerical display of data points corresponding to each reactor vessel 1542 in reactor 1506, and graphical display 1842 for color display of the data points displayed in array 1840. Color display 1842 can take the form of a two dimensional array of reactor vessels or three dimensional color histogram 1870, shown in FIG. 64. The color range for graphical display 1842 and histogram 1870 is displayed in legends 1872 and 1874, respectively. Data display pane 1838 can display either temperature data or conversion data calculated from pressure measurements as described above. In either case, the displayed data is refreshed at the rate set in the system options window 1730.

Figure 65:
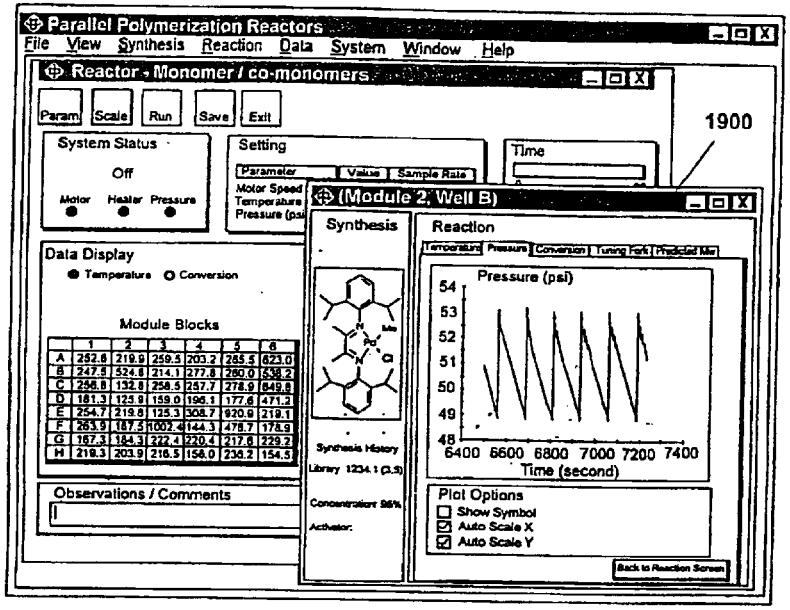
FIG. 65 is an illustration of a window displaying experimental results for a single reactor vessel.

By selecting an individual reactor vessel 1542 in data display pane 1838, the user can view a detailed data window 1900 for that vessel, as shown in FIG. 65. Data window 1900 provides a graphical display of experimental results, including, for example, temperature, pressure, conversion and molecular weight data for that vessel for the duration of the experiment.

Referring again to FIG. 64, toolbar 1876 lets the user set reactor parameters (by entering reactor setup window 1760) and color scaling for color displays 1842 and 1870. The user can also begin or end an experiment, save results and exit system 1500 using toolbar 1876. The user can enter any observations or comments in comment box 1878. User comments and observations can be saved with experimental results.

Figure 66:
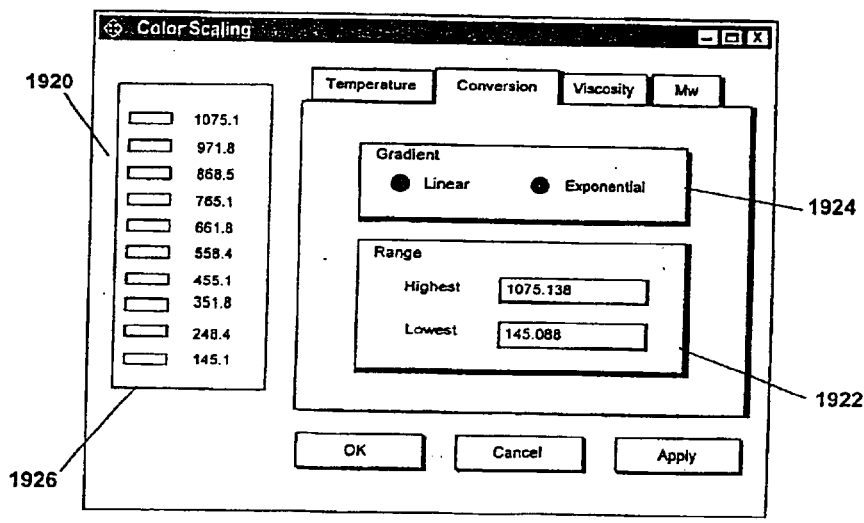
FIG. 66 is an illustration of a dialog window for user input of color scaling parameters.

Referring to FIG. 66, the user can set the color scaling for color displays 1842 and 1870 through color scaling window 1920. Color scaling window 1920 lets the user select a color range corresponding to temperature or conversion in color range pane 1922. The user can also set a color gradient, either linear or exponential, through color gradient pane 1924. Color scaling window 1920 displays the selected scale in color legend 1926.

The invention can be implemented in digital electronic circuitry, or in computer hardware, firmware, software, or in combinations of them. Apparatus of the invention can be implemented in a computer program product tangibly embodied in a machine-readable storage device for execution by a programmable processor, and method steps of the invention can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language.

Suitable computer programs in modules 1508 and 1514 can be implemented in classes as set forth in the following tables. (The prefix "o" in a name indicates that the corresponding property is a user-defined object; the prefix "c" in a name indicates that the corresponding property is a collection.)

1. Application Class

Property Table:

| Category | Name | Access | Description/Comments |
|---|---|---|---|
| General | ClsName | Get | Class name |
| | AppName | Get | Application name |
| | sRootDir | Get/Let | Root directory of all system files |
| | bDebugMode | Get/Let | System running mode. If TRUE, display message boxes for errors in addition to error logging. If FALSE, log the error to the log file |
| | DBIsConnected | Get/Let | Whether database is connected |

-continued

| Category | Name | Access | Description/Comments |
|---|---|---|---|
| System Registry | SectionGeneral | Get | General section |
| | SectionSystem Limits | Get | Section for System Limit Values |
| | SectionDefault Param | Get | Section for system default parameters |
| ColorScaling | oTempScale | Get | Color Scale object for temperature data |
| | oViscosity Scale | Get | Color Scale object for viscosity data |
| | oConversion Scale | Get | Color Scale object for conversion data |
| | oMWScale | Get | Color Scale object for molecule weight data |

Method Table:

| Name | Argument List | Return Type | Description/Comments |
|---|---|---|---|
| SaveCnfg | | Boolean | Save application configurations to the system registry |

2. Color Scale Class

Parent Class: Application

Property Table:

| Name | Access | Description/Comments |
|---|---|---|
| ClsName | Get | Class name |
| Highest | Get/Let | Highest value |
| GradientType | Get/Let | Type of the gradient between the lowest and highest to the log file |
| LegendValues | Get | A collection of legend values |

Method Table:

| Name | Argument List | Return Type | Description/Comments |
|---|---|---|---|
| SetLegendValues | | | Recalculate the legend values according to the current property values |
| GetLegendColor | fValue | long | Get color of the specified data value |

3. Color Legend Class

Parent Class: Color Scale

Property Table:

| Name | Access | Description/Comments |
|---|---|---|
| ClsName | Get | Class Name |
| ColorCount | Get | Number of colors used in the legend |

Method Table:

| Name | Argument List | Return Type | Description/Comments |
|---|---|---|---|
| GetColorValue | fValue | long | Get color for the specified data value |

4. System Class

Property Table:

| Category | Name | Access | Description/Comments |
|---|---|---|---|
| General | ClsName | Get | |
| | ExpID | | |
| System Status | Status | Get/Let | Status variable |
| | STATUS_OFF | Get | constant |
| | STATUS_RUN | Get | constant |
| | STATUS_IDLE | Get | constant |
| | STATUS_ERROR | Get | constant |
| System Timing | oExpTiming | Get | Control and record the experiment time |
| | oDisplayTiming | Get | Control the data display updating rate |
| System Alarming | oAlarm | Get | Provide alarm when system error occurs |
| System Components | oMotors | Get | |
| | oHeaters | Get | |
| | oPressures | Get | |

Method Table:

| Name | Argument List | Return Type | Description/Comments |
|---|---|---|---|
| Run | | | |
| StopRunning | | | |
| Archive | | | |

5. ExpTiming Class

Parent Class: System

Property Table:

| Name | Access | Description/Comments |
|---|---|---|
| ClsName | Get | Class Name |
| TimingByTime | Get/Let | Boolean type |
| TimingByPressure | Get/Let | Boolean type |
| TimingByTemperature | Get/Let | Boolean type |
| TargetTime | Get/Let | System will stop if specified target value is achieved |
| TargetPressure | Get/Let | System will stop if specified target value is achieved |
| TargetTemperature | Get/Let | System will stop if specified target value if achieved |
| ExpDate | Get/Let | Date when experiment starts to run |
| ExpStartTime | Get/Let | Time when experiment starts to fun |
| ExpEndTime | Get/Let | Time when experiment stop running |
| ExpElapsedTime | Get/Set | The time passed during the experiment |
| TimerInterval | Let | Timer used to update the elapsed time |

Method Table:

| Name | Argument List | Return Type | Description |
|---|---|---|---|
| LoadDefaultExpTiming | | Boolean | |
| SaveDefaultExpTiming | | Boolean | |

6. DisplayTiming Class

Parent Class: System

Property Table:

| Name | Access | Description/Comments |
|---|---|---|
| ClsName | Get | Class Name |
| DisplayTimer | Get/Set | Timer used to update the data |
| TimerIntercal | Get/Let | |

Method Table:

| Name | Argument List | Return Type | Description |
|---|---|---|---|
| SaveDefaultParam | | Boolean | |

7. Alarm class

Parent Class: System

Property Table:

| Name | Access | Description/Comments |
|---|---|---|
| ClsName | Get | Class Name |
| BeepTimer | Set | Timer used to control beep |
| PauseTimer | Set | Timer used to pause the beep |
| BeepStatus | Get | A boolean value: FALSE if paused, otherwise TRUE |
| BeepPauseTime | Let | Time duration for beep to pause |

Method Table:

| Name | Argument List | Return Type | Description |
|---|---|---|---|
| TurnOnBeep | | | Start to beep |
| TurnOffBeep | | | Stop beeping |
| BeepPause | | | Disable beep |
| BeepResume | | | Enable beep |

8. Motors Class

Parent Class: System

Property Table:

| Name | Access | Description/Comments |
|---|---|---|
| ClsName | Get | Class Name |
| SpeedLimit | Get/Let | Safety Limit |
| MotorIsOn | Get/Let | Status variable |
| Card1AxesCount | Get/Let | Axes count in card1 |
| Card2AcesCount | Get/Let | Axes count in card2 |
| oMotorCard1 | Get | Motor card object |
| oMotorCard2 | Get | Motor card object |
| oSpinTimer | Get/Set | Timer for dual spin |
| FoundDLL | Get | Motion DLL |
| ErrCode | Get | Error code |

Method Table:

| Category | Name | Argument List | Return Type | Description |
|---|---|---|---|---|
| To/From system Registry | LoadDefaultParam SaveDefaultParam SaveCardAxesCount SaveSystemLimit | | Boolean Boolean Boolean Boolean | |
| Create/ Delete Card Objects | CreateCard1 CreateCard2 DeleteCard1 DeleteCard2 | iAxesCount iAxesCount | | |
| Motor Control | Init Spin run StopRunning | iAxis, dSpeed | Boolean Boolean Boolean Boolean | For all axes For all axes For all axes |
| Archive | ArchiveParam | iFileNo | Boolean | |

9. MotorAxis Class

Parent Class: Motors

Property Table:

| Name | Access | Description/Comments |
|---|---|---|
| ClsName | Get | Class Name |
| Parent | Set | Reference to the parent object |
| MotorID | Get/Let | Motor Axis ID |
| oCurParam | Get | Reference to current parameter setting |

Method Table:

| Name | Argument List | Return Type | Description |
|---|---|---|---|
| GetParamSetting | [index] | MotorParam | Return the last in the parameter collection |
| Run | | Boolean | Add oCurParam to the Param collection, and run this motor axis |

10. Motor Param Class

Parent Class: Motors

Property Table:

| Name | Access | Description/Comments |
|---|---|---|
| clsName | Get | Class Name |
| Parent | Set | Reference to the parent object |
| MotionType | Get/Let | Dual or single direction spin |
| DeltaT | Get/Let | Time duration before changing spin direction |
| SpinRate | Get/Let | Spin rate in RPM |
| EffectiveTime | Get/Let | Time the parameters take effect |

Method Table:

| Name | Argument List | Return Type | Description |
|---|---|---|---|
| PrintParam | iFileNo | Boolean | Print the parameters to file |

11. Heaters Class

Parent Class: System

Property Table:

| Name | Access | Description/Comments |
|---|---|---|
| ClsName | Get | Class Name |
| oParent | Get | Reference to the parent object |
| TempLimit | Get/Let | Temperature Safety Limit |
| SplRateLimit | Get/Let | Sample Rate Limit |
| CtlrLoopCount | Get/Let | Loop count in controller1 |
| CtlrLoopCount | Get/Let | Loop count in controller2 |
| HeaterIsOn | Get/Let | Status variable |
| oHeaterCtlr1 | Get | Heater controller object as clsHeaterCtlr |
| oHeaterCtlr2 | Get | Heater controller object as clsHeaterCtlr |
| oData | Get | Data object as clsHeaterData |
| lDataPointsInMem | Get/Let | Number of data points kept in memory |
| FoundDLL | Get | RS232 DLL. If found, 1, otherwise −1 |
| ErrCode | Get | Error Code |

Method Table:

| Category | Name | Argument List | Return Type | Descriptions |
|---|---|---|---|---|
| To/From system Registry | LoadDefaultParam SaveDefaultParam SaveCtlrLoopCount SaveSystemLimit | | Boolean Boolean Boolean Boolean | |
| Create/ Delete Ctlr Objects | Create Ctlr 1 Create Ctlr 2 Delete Ctlr 1 Delete Ctlr 2 | iLoopCount iLoopCount | | |
| Heater Control | Init | | Boolean | Open COM1, COM2 |
| | OutputHeat | | Boolean | For all loops |
| | TurnOff | | Boolean | For all loops |
| | GetTemp | | Boolean | For all loops |
| | SafetyMonitor | Icount, vData | | Check Temperature |
| | SafetyHandler | | | |
| Archive | ArchiveParam | iFileNo | Boolean | |

12. HeaterCtlr Class

Parent Class: Heaters

Property Table:

| Name | Access | Description/Comments |
|---|---|---|
| ClsName | Get | Class Name |
| Parent | Set | Reference to the parent object |
| oCurParam | Get | Reference to current parameter setting |

Method Table:

| Name | Argument List | Return Type | Description |
|---|---|---|---|
| AddParamSetting | oParam | Boolean | Add the parameter object to the parameter collection |
| GetParamSetting | [index] | HeaterParam | Return the last in the parameter collection |

13. HeaterParam Class
Parent Class: HeaterCtlr
Property Table:

| Name | Access | Description/Comments |
|---|---|---|
| clsName | Get | Class Name |
| Parent | Set | Reference to the parent object |
| Setpoint | Get/Let | Setpoint for temperature |
| SplRate | Get/Let | Sampling Rate (Hz) |
| EffectiveTime | Get/Let | Time the parameters take effect |

Method Table:

| Name | Argument List | Return Type | Description |
|---|---|---|---|
| PrintParam | iFileNo | Boolean | Print the parameters to file |

14. HeaterData Class
Parent Class: Heaters
Property Table:

| Name | Access | Description/Comments |
|---|---|---|
| clsName | Get | Class Name |
| Parent | Set | Reference to the parent object |
| DataPointsInMem | Let | |
| LoopCount | Let | Total loop count |
| DataCount | Get | Data point count |
| cTime | Get | Get time data collection |
| cTemp | Get | Get temperature data collection |

Method Table:

| Name | Argument List | Return Type | Description |
|---|---|---|---|
| GetData | ByRef fTime, ByRef vTemp [,index] | Boolean | Get current data set, or the data set with specified index |
| AddData | fTime, vTemp | | Add the data set to the data collections |
| ClearData | | | Clear the data collection |
| WriteToDisk | | | Write the current data to disk file |

15. Pressures Class
Parent Class: System
Property Table:

| Name | Access | Description/Comments |
|---|---|---|
| ClsName | Get | Class Name |
| oParent | Get | Reference to the parent object |
| PressureLimit | Get/Let | Pressure Safety Limit |
| SplRateLimit | Get/Let | Sample Rate Limit |
| ChannelCount | Get/Let | Analog Input channel count |
| PressureIsOn | Get/Let | Status variable |
| oData | Get | Data object as clsPressureData |
| 1DataPointsInMem | Get/Let | Number of data points kept in memory |
| oCWAOP | Get | Object of analog output ActiveX control |
| oCWAIP | Get | Object of analog input ActiveX control |
| ErrCode | Get | Error code |

Method Table:

| Category | Name | Argument List | Return Type | Description |
|---|---|---|---|---|
| To/From System Registry | LoadDefaultParam | | Boolean | |
| | SaveDefaultParam | | Boolean | |
| | SaveChannelCount | | Boolean | |
| | SaveDataPointsInMem | | | |
| | SaveSystemLimit | | Boolean | |
| Pressure System Control | AnalogOutput | | Boolean | Output Pset |
| | GetAIData | | Boolean | Analog Input |
| Archive | ArchiveParam | iFileNo | Boolean | |

16. PressureParam Class
Parent Class: Pressures
Property Table:

| Name | Access | Description/Comments |
|---|---|---|
| clsName | Get | Class Name |
| Parent | Set | Reference to the parent object |
| Setpoint | Get/Let | Setpoint for pressure (psi) |
| SplRate | Get/Let | Sampling Rate (Hz) |
| EffectiveTime | Get/Let | Time the parameters take effect |

Method Table:

| Name | Argument List | Return Type | Description |
|---|---|---|---|
| PrintParam | iFileNo | Boolean | Print the parameters to the file |

17. PressureData Class
Parent Class: Pressures
Property Table:

| Name | Argument | Access | Description/Comments |
|---|---|---|---|
| clsName | | Get | Class Name |
| Parent | | Set | Reference to the parent object |
| DataPointsInMem | | Let | |
| ChannelCount | | Let | Total AI channel count |
| PresCount | | Get | Pressure data point count |
| ConvCount | | Get | Conversion data point count |
| cPresTime | | Get | Get time collection for pressure data |
| cPressure | | Get | Get pressure data collection |
| cConvTime | iChannelNo | Get | Get time collection for conversion data |
| cConversion | iChannelNo | Get | Get conversion data collection |

Method Table:

| Name | Argument List | Return Type | Description |
|---|---|---|---|
| GetCurPres | ByRef vPres | Boolean | Get current pressure data set |
| GetCurConv | ByRef vConv | Boolean | Get current conversion data set |

-continued

| Name | Argument List | Return Type | Description |
|---|---|---|---|
| AddPres | fTime, vPres | | Add the pressure data set to the pressure data collections, then calculate conversions |
| ClearData | | | Clear all the data collections |
| WritePresToDisk | | Boolean | Write the current pressure data to disk file |
| WriteConvToDisk | | Boolean | Write the current conversion data to disk file |

18. ErrorHandler Class
    Property Table:

| Name | Access | Description/Comments |
|---|---|---|
| ClsName | Get | Class Name |
| LogFile | Get/Let | Log file for error messages |

Method Table:

| Name | Argument List | Return Type | Description |
|---|---|---|---|
| SaveConfg | | Boolean | |
| OpenLogFile | iFileNo | Boolean | Open log file with specified file number for APPEND, lock WRITE |
| OpenLogfile | iFileNo | Boolean | Open log file with specified file number for APPEND, lock WRITE |
| CloseLogFile | | | |
| LogError | sModName, sFuncName, iErrNo, sErrText | | Write error messages to the log file, also call DisplayError in debug mode |
| DisplayError | sModName, sFuncName, iErrNo, sErrText | | Show message Box to display the error |

Suitable processors include, by way of example, both general and special purpose microprocessors. Generally, a processor will receive instructions and data from a read-only memory and/or a random access memory. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

To provide for interaction with a user, the invention can be implemented on a computer system having a display device such as a monitor or LCD screen for displaying information to the user and a keyboard and a pointing device such as a mouse or a trackball by which the user can provide input to the computer system. The computer system can be programmed to provide a graphical user interface through which computer programs interact with users.

Figure 67:
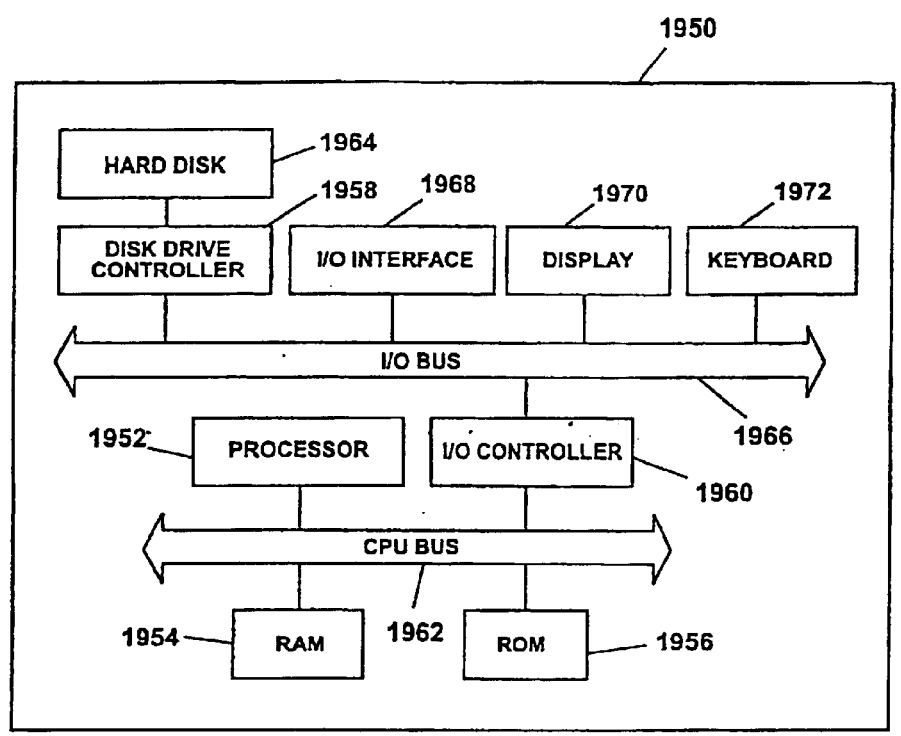
FIG. 67 is a schematic diagram of a computer platform suitable for implementing the data processing system of the invention.

An example of one such type of computer is shown in FIG. 67, which shows a block diagram of a programmable processing system 1950 suitable for implementing or performing the apparatus or methods of the invention. The system 1950 includes a processor 1952, a random access memory (RAM) 1954, a program memory 1956 (for example, a writable read-only memory (ROM) such as a flash ROM), a hard drive controller 1958, and an input/output (I/O) controller 1960 coupled by a processor (CPU) bus 1962. The system 1950 can be preprogrammed, in ROM, for example, or it can be programmed (and reprogrammed) by loading a program from another source (for example, from a floppy disk, a CD-ROM, or another computer).

The hard drive controller 1958 is coupled to a hard disk 1964 suitable for storing executable computer programs, including programs embodying the present invention, and data including the images, masks, reduced data values and calculated results used in and generated by the invention. The I/O controller 1960 is coupled by means of an I/O bus 1966 to an I/O interface 1968. The I/O interface 1968 receives and transmits data in analog or digital form over communication links such as a serial link, local area network, wireless link, and parallel link. Also coupled to the I/O bus 1966 is a display 1970 and a keyboard 1972. Alternatively, separate connections (separate buses) can be used for the I/O interface 1966, display 1970 and keyboard 1972.

The invention has been described in terms of particular embodiments. Other embodiments are within the scope of the following claims. Although elements of the invention are described in terms of a software implementation, the invention may be implemented in software or hardware or firmware, or any combination of the three. In addition, the steps of the invention can be performed in a different order and still achieve desirable results.

Moreover, the above description is intended to be illustrative and not restrictive. Many embodiments and many applications besides the examples provided will be apparent to those of skill in the art upon reading the above description. The scope of the invention should therefore be determined, not with reference to the above description, but should instead be determined with reference to the appended claims, along with the full scope of equivalents to which such claims are entitled. The disclosures of all articles and references, including patent applications and publications, are incorporated by reference for all purposes.

What is claimed is:

1. Apparatus for the parallel processing of reaction mixtures, comprising a reactor block having a series of wells therein extending down from an upper surface of the block for containing the reaction mixtures, an upper plate removably secured to said reactor block over said upper surface thereof, said upper plate having openings therein in registry with the wells in the reactor block, stirring mechanisms attached to said upper plate and removable with the upper plate for stirring said reaction mixtures, said stirring mechanisms extending down through the openings in the upper plate and into respective wells, and seals for sealing against leakage through said upper plate openings when the upper plate is secured to the reactor block, each stirring mechanism comprising a drive mounted on said upper plate and a multi-piece spindle rotatable by said drive, said multi-piece spindle having a metal upper spindle portion, a plastic stirrer, and a coupling for releasably coupling the plastic stirrer to the metal upper spindle portion in a position wherein the stirrer extends down into a respective well, said plastic stirrer being removable from said coupling after a mixing operation to permit discard and replacement of the stirrer.

2. An apparatus for parallel processing of reaction mixtures comprising:

a reactor block having a series of wells therein extending from an exterior surface of the block for containing the reaction mixtures, a removable plate removably secured to the reactor block, the removable plate having openings therein in registry with the wells in the reactor block, a temperature control system for regulating the temperature of the reaction mixtures, and a stirring system attached to the removable plate and removable with the removable plate for agitating the reaction mixtures, the stirring system comprising:

spindles extending into respective wells, each of the spindles having a first end portion and a second end portion, a stirring blade attached to the first end portion of each of the spindles, and a drive mechanism located external to the wells that is adapted to rotate the spindles.

3. The apparatus of claim 2 wherein said spindle and stirring blade are formed of a chemically resistant plastic material.

4. The apparatus of claim 3 wherein said spindle and stirring blade comprise polyethylethylketone (PEEK).

5. The apparatus of claim 3 wherein said spindle and stirring blade comprise polytetrafluoroethylene (PTFE).

6. The apparatus of claim 2 further comprising magnetic feed through devices for magnetically coupling the drive mechanism to the spindles.

7. The apparatus as set forth in claim 6 wherein said drive mechanism comprises a gear train for rotating each magnetic feed through device, and a motor for rotating gears of the gear train to effect conjoint rotation of the spindles at speeds from about 0 to about 3000 rpm.

8. The apparatus of claim 2 further comprising removable liners in the wells.

9. The apparatus as set forth in claim 8, wherein each liner has as volume of less than about 500 ml.

10. The apparatus of claim 2 wherein said removable plate is removably secured face-to-face with said exterior surface of the reactor block.

11. The apparatus of claim 10, wherein said exterior surface of the reactor block is an upper surface, and wherein said removable plate is an upper plate overlying said upper surface.

12. The apparatus of claim 2, wherein each of said wells is sealed against fluid communication with the other wells.

13. A combinatorial chemistry reactor system for parallel processing of reaction mixtures, said system comprising a reactor block having a series of wells therein for holding said reaction mixtures, a removable plate removably secured to the reactor block, the removable plate having openings therein in registry with the wells in the reactor block, seals for sealing the wells of the reactor block to allow said reaction mixtures to react under pressure when the removable plate is secured to the reactor block, and a stirring system supported by the removable plate and removable with the removable plate for agitating the reaction mixtures, the stirring system comprising stirrers extending into respective wells, and a drive mechanism located external to the wells for moving the stirrers to agitate reaction mixtures in the wells.

14. A system as set forth in claim 13 wherein said drive mechanism comprises a drive train for driving said stirrers, and a motor for driving the drive train.

15. A system as set forth in claim 14 wherein said drive train comprises a plurality of drive gears in mesh with one another and a motor for driving said drive gears.

16. A system as set forth in claim 13 wherein said drive mechanism comprises a plurality of drive gears on the stirrers, and one or more motors for driving said drive gears.

17. A system as set forth in claim 16 wherein said drive gears are in mesh and driven by a single motor.

18. A system as set forth in claim 13 wherein said stirrers are removably attached to said drive mechanism.

19. A system as set forth in claim 13 wherein said stirrers are of a non-metal chemically resistant material.

20. A system as set forth in claim 19 wherein said stirrers are of a polymer material.

21. A system as set forth in claim 20 wherein said stirrers comprise polyethylethylketone (PEEK).

22. A system as set forth in claim 20 wherein said stirrers comprise polytetrafluoroethylene (PTFE).

23. A system as set forth in claim 13 further comprising fasteners for removably fastening said removable plate in face-to-face relation with an upper surface of said reactor block.

24. A combinatorial chemistry reactor system for parallel processing of reaction mixtures, said system comprising a reactor block having a series of wells therein extending down from an upper surface of the block, said wells holding said reaction mixtures, an upper plate removably secured to the reactor block in face-to-face relation with said upper surface, the removable plate having openings therein in registry with the wells in the reactor block, seals for sealing the wells of the reactor block to allow said reaction mixtures to react under pressure when the removable plate is secured to the reactor block, and a stirring system supported by the removable plate and removable with the removable plate for agitating the reaction mixtures, the stirring system comprising stirrers extending into respective wells, and a drive mechanism located external to the wells for moving the stirrers to agitate reaction mixtures in the wells, said drive mechanism comprising a drive train for driving said stirrers and one or more motors for driving said drive train, said stirrers being removably attached to said drive mechanism.

25. The reactor system as set forth in claim 24 wherein each stirrer comprises a shaft having a plastic core and a plastic mixing blade on the shaft.

26. The reactor system as set forth in claim 25 wherein each stirrer is sized for reception in a well having a volume of less than 500 ml.

27. The reactor system as set forth in claim 26, wherein each stirrer is sized for reception a well having a volume of less than about 20 ml.

28. The reactor system as set forth in claim 25, wherein said plastic core comprises polyethylethylketone (PEEK).

29. The reactor system as set forth in claim 25 wherein said plastic core comprises polytetrafluoroethylene (PTFE).

* * * * *

UNITED STATES PATENT AND TRADEMARK OFFICE
CERTIFICATE OF CORRECTION

PATENT NO. : 6,890,492 B1
DATED : May 10, 2005
INVENTOR(S) : Howard Turner et al.

It is certified that error appears in the above-identified patent and that said Letters Patent is hereby corrected as shown below:

Column 54,
Line 60, "reception a well" should read -- reception in a well --.

Signed and Sealed this

Eleventh Day of October, 2005

JON W. DUDAS
*Director of the United States Patent and Trademark Office*